US011634411B2

(12) United States Patent
Holmes et al.

(10) Patent No.: US 11,634,411 B2
(45) Date of Patent: *Apr. 25, 2023

(54) COMPOUNDS AND METHODS FOR THE TREATMENT OF OCULAR DISORDERS

(71) Applicant: Azura Ophthalmics Ltd., Tel Aviv (IL)

(72) Inventors: Ian Holmes, Victoria (AU); Yair Alster, Tel Aviv (IL); Hila Barash, Shoham (IL); Charles Bosworth, Las Vegas, NV (US); Omer Rafaeli, Udim (IL); Marc Gleeson, Longueville (AU); Mark Richard Stewart, Cambridge (GB); Robert M. Burk, Laguna Beach, CA (US); Jonathan Dunn, Cambridge (GB); Nicholas Chapman, Cambridge (GB)

(73) Assignee: AZURA OPHTHALMICS LTD., Tel Aviv (IL)

( * ) Notice: Subject to any disclaimer, the term of this patent is extended or adjusted under 35 U.S.C. 154(b) by 217 days.

This patent is subject to a terminal disclaimer.

(21) Appl. No.: 17/112,371

(22) Filed: Dec. 4, 2020

(65) Prior Publication Data
US 2021/0107899 A1    Apr. 15, 2021

Related U.S. Application Data

(63) Continuation of application No. 16/904,036, filed on Jun. 17, 2020, now Pat. No. 10,875,845, which is a continuation of application No. PCT/IB2020/000288, filed on Apr. 16, 2020.

(60) Provisional application No. 62/835,963, filed on Apr. 18, 2019.

(51) Int. Cl.
C07D 405/06 (2006.01)
C07D 409/14 (2006.01)
C07D 405/14 (2006.01)
A61P 27/02 (2006.01)

(52) U.S. Cl.
CPC ............ *C07D 405/06* (2013.01); *A61P 27/02* (2018.01); *C07D 405/14* (2013.01); *C07D 409/14* (2013.01)

(58) Field of Classification Search
CPC ................ C07D 405/06; C07D 405/14; C07D 409/14; C07D 211/62; C07D 211/34; A61P 27/02; A61P 43/00; A61P 17/00; A61K 47/545; A61K 9/0048; A61K 31/445; A61K 31/4725
See application file for complete search history.

(56) References Cited

U.S. PATENT DOCUMENTS

| | | |
|---|---|---|
| 5,846,514 A | 12/1998 | Foster et al. |
| 6,239,113 B1 | 5/2001 | Dawson et al. |
| 6,334,997 B1 | 1/2002 | Foster et al. |
| 6,569,443 B1 | 5/2003 | Dawson et al. |
| 7,056,893 B2 | 6/2006 | Roy et al. |
| 7,314,938 B2 | 1/2008 | Shen et al. |
| 7,745,460 B2 | 6/2010 | Shen et al. |
| 7,790,743 B2 | 9/2010 | Shen et al. |
| 7,928,122 B2 | 4/2011 | Shen et al. |
| 8,084,047 B2 | 12/2011 | Shen et al. |
| 8,168,655 B2 | 5/2012 | Gadek et al. |
| 8,357,506 B2 | 1/2013 | Burnet et al. |
| 8,367,701 B2 | 2/2013 | Burnier et al. |
| 8,592,450 B2 | 11/2013 | Gadek et al. |
| 8,927,574 B2 | 1/2015 | Burnier |
| 9,085,553 B2 | 7/2015 | Zeller et al. |
| 9,216,174 B2 | 12/2015 | Shen et al. |
| 9,353,088 B2 | 5/2016 | Burnier |
| 9,447,077 B2 | 9/2016 | Burnier et al. |
| 9,463,201 B2 | 10/2016 | Alster et al. |
| 9,890,141 B2 | 2/2018 | Burnier |
| 10,124,000 B2 | 11/2018 | Shen et al. |
| 10,875,845 B2 | 12/2020 | Holmes et al. |
| 11,459,351 B1 | 10/2022 | Holmes et al. |
| 2006/0099660 A1 | 5/2006 | Burnet et al. |
| 2009/0075978 A1 | 3/2009 | Haurand et al. |
| 2014/0031387 A1 | 1/2014 | Zeller et al. |

(Continued)

FOREIGN PATENT DOCUMENTS

| | | |
|---|---|---|
| WO | WO-2014100135 A1 | 6/2014 |
| WO | WO-2017182885 A2 | 10/2017 |

(Continued)

OTHER PUBLICATIONS

Tilley, J.W. "Identification of N-acyl 4-(3-pyridonyl) phenylalanine derivatives and their orally active prodrug esters as dual acting α4β1 and α4β7 receptor antagonists." Bioorganic & medicinal chemistry letters 23.4 (2013): 1036-1040.*
Cholkar, K., "Novel strategies for anterior segment ocular drug delivery." Journal of ocular pharmacology and therapeutics 29.2 (2013): 106-123.*
Barabino et al. Animal Models of Dry Eye: A Critical Assessment of Opportunities and Limitations. Invest. Ophthalmol. Vis. Sci. 45:1641-1646 (2004).
Barabino et al. The Controlled-Environment Chamber: A New Mouse Model of Dry Eye. Invest. Ophthalmol. Vis. Sci. 46:2766-2771 (2005).

(Continued)

*Primary Examiner* — John M Mauro
(74) *Attorney, Agent, or Firm* — Wilson Sonsini Goodrich & Rosati

(57) ABSTRACT

Described herein are compositions and methods for the treatment of ocular surface disorders including meibomian gland dysfunction, blepharitis, dry eye disease and other inflammatory and/or infectious disease of the anterior surface of the eye. Said compositions and methods comprise keratolytic conjugates which demonstrate keratolytic activity, and anti-inflammatory or other desirable activities. Topical administration of said compositions to the eyelid margin or surrounding areas provides therapeutic benefit to patients suffering from ocular surface disorders.

1 Claim, No Drawings

(56) References Cited

U.S. PATENT DOCUMENTS

| | | | |
|---|---|---|---|
| 2016/0074381 | A1 | 3/2016 | Shen et al. |
| 2020/0030268 | A1 | 1/2020 | Amselem et al. |
| 2022/0332749 | A1 | 10/2022 | Holmes et al. |

FOREIGN PATENT DOCUMENTS

| | | |
|---|---|---|
| WO | WO-2018161039 A1 | 9/2018 |
| WO | WO-2020212755 A1 | 10/2020 |
| WO | WO-2020212760 A2 | 10/2020 |
| WO | WO-2022084738 A2 | 4/2022 |

OTHER PUBLICATIONS

Berge et al. Pharmaceutical Salts. Journal of Pharmaceutical Sciences 66(1):1-19 (Jan. 1977).

Dursun et al. A Mouse Model of Keratoconjunctivitis Sicca. Invest. Ophthalmol. Vis. Sci. 43:632-638 (2002).

Evans. Synthesis of radiolabeled compounds. J Radioanal Chem 64(1-2):9-32 (1981).

Kabalka et al. The Synthesis of Radiolabeled Compounds via Organometallic Intermediates. Tetrahedron 45(21):6601-6621 (1989).

Krauss et al. Improvement of Outcome Measures of Dry Eye by a Novel Integrin Antagonist in the Murine Desiccating Stress Model. Invest. Ophthalmol. Vis. Sci. 56(10):5888-5895 (2015).

Maag. Prodrugs of carboxylic acids. Prodrugs. Springer, New York, NY (pp. 703-729) (2007):.

Nichols et al. The International Workshop on Meibomian Gland Dysfunction: Executive Summary. Invest. Ophthalmol. Vis. Sci. 52(4):1922-1929 (2011).

Niederkorn et al. Desiccating Stress Induces T Cell-Mediated Sjögren's Syndrome-like Lacrimal Keratoconjunctivitis. J. Immunol. 176:3950-3957 (2006).

PCT/IB2020/000288 International Search Report and Written Opinion dated Sep. 10, 2020.

PCT/IB2020/000288 Invitation to Pay Additional Fees dated Jul. 16, 2020.

Pflugfelder et al. A Randomized, Double-Masked, Placebo-Controlled, Multicenter Comparison of Loteprednol Etabonate Ophthalmic Suspension, 0.5%, and Placebo for Treatment of Keratoconjunctivitis Sicca in Patients With Delayed Tear Clearance. Am J Ophthalmol 138:444-57 (2004).

Pflugfelder et al. International Dry Eye Workshop, 2007. Management and Therapy of Dry Eye Disease: Report of the Management and Therapy Subcommittee of the International Dry Eye WorkShop. Ocul Surf 5:163-178 (2007).

Rautio et al. Prodrugs: design and clinical applications. Nat Rev Drug Discov 7(3):255-270 (2008).

Ravensberg et al. The Effect of a Single Inhaled Dose of a VLA-4 Antagonist on Allergen-Induced Airway Responses and Airway Inflammation in Patients With Asthma. Allergy 61:1097-1103 (2006).

Schaumberg et al. The International Workshop on Meibomian Gland Dysfunction: Report of the Subcommittee on the Epidemiology Of, and Associated Risk Factors For, MGD. Invest. Ophthalmol. Vis. Sci. 52(4):1994-2005 (2011).

PCT/IB2021/000707 International Search Report and Written Opinion dated May 16, 2022.

PCT/IB2021/000707 Invitation to Pay Additional Fees dated Feb. 23, 2022.

Pub Chem SID 244662985 (Mar. 17, 2015).

Pub Chem SID 244881306 (Mar. 17, 2015).

Blackie et al. Treatment for meibomian gland dysfunction and dry eye symptoms with a single-dose vectored thermal pulsation. Curr Opin Ophthalmol 26(4):306-13 (2015).

Knop et al. The International Workshop on Meibomian Gland Dysfunction: Report of the Subcommittee on Anatomy, Physiology, and Pathophysiology of the Meibomian Gland. IOVS 52(4):1938-1978 (2011).

Lane et al. A New System, the LipiFlow, for the Treatment of Meibomian Gland Dysfunction. Cornea 31(4):396-404 (2012).

U.S. Appl. No. 17/222,802 dated Aug. 25, 2021.

U.S. Appl. No. 17/222,802 dated Dec. 13, 2021.

Semba et al. A Phase 2 Randomized, Double-Masked, Placebo-Controlled Study of a Novel Integrin Antagonist (SAR 1118) for the Treatment of Dry Eye. American Journal Of Ophthalmology 153(6):1050-1060 (2012).

Zhong et al. Discovery and Development of Potent LFA-1/ICAM-1 Antagonist SAR 1118 as an Ophthalmic Solution for Treating Dry Eye. ACS medicinal chemistry letters 3(3):203-206 (2012) (Including Supporting Information).

* cited by examiner

COMPOUNDS AND METHODS FOR THE TREATMENT OF OCULAR DISORDERS

CROSS-REFERENCE TO RELATED APPLICATIONS

This application is a continuation of U.S. application Ser. No. 16/904,036, filed Jun. 17, 2020, which is a continuation application of International Application No. PCT/IB2020/000288, filed Apr. 16, 2020, and claims the benefit of U.S. Provisional Application No. 62/835,963, filed Apr. 18, 2019, all of which are incorporated herein by reference in their entirety.

BACKGROUND OF THE INVENTION

Restasis (0.05% cyclosporine A, Allergan) was approved by the Food and Drug Administration (FDA) to increase tear production in patients whose tear production is presumed to be suppressed due to ocular inflammation associated with keratoconjunctivitis sicca. Xiidra® (lifitegrast ophthalmic solution) 5% is indicated for the treatment of signs and symptoms of dry eye disease (DED).

SUMMARY OF THE INVENTION

Provided in certain embodiments herein are compounds, pharmaceutical (e.g., ophthalmic) compositions, and methods of treatment. In specific embodiments, methods of treatment provided herein include the treatment of ocular and/or periocular indications or abnormalities. In some embodiments, the ocular and/or periocular indications or abnormalities treated by or with a composition or compound provided herein are indications or abnormalities that have multifactorial etiologies and/or interactions. In certain embodiments provided herein are compounds (and compositions comprising such compounds) that have multifunctional efficacies, such as when administered in or around the eye (e.g., to the ocular surface, the eyelid, such as the eyelid margin or the inner surface of the eyelid, or the like).

In certain embodiments, methods provided herein involve the method of treating meibomian gland dysfunction (MGD).

Currently there are no approved pharmacological agents useful for the treatment of MGD. The recognition that terminal duct obstruction from hyperkeratinization of the ductal epithelium on meibomian glands is a core mechanism behind meibomian gland dysfunction (MGD) is consistent with clinical experience demonstrating that effective treatments for MGD require resolution of ductal obstruction and evacuation of glandular contents (Nichols et al, 2011; Lane et al, 2012; Blackie et al, 2015). Warm compresses and thermal/mechanical devises (e.g., LipiFlow) are used in an attempt to raise the internal temperature of the meibomian glands over the normal melting point for meibum (i.e., 32° C. to 40° C.) in an attempt to resolve terminal duct obstruction (Lane et al, 2012). Unfortunately, warm compresses are unable to achieve this benefit for severely obstructed glands which can having a melting point >40° C. Current technology for removing keratinized obstruction of the meibomian gland also includes physical removal methods (e.g., debridement and gland probing), which are quite painful to patients.

Subsequent to a period of MGD, various stages of inflammatory or bacterial disease at the ocular surface are frequently observed because meibomian gland obstruction can cause a cascade of events that include further deterioration of the glands (Knop, IOVS, 2011) from stasis of the meibum in the secretory glands, mechanical pressure and stress from glandular obstruction, and increased bacterial growth that is associated with the downstream release of bacterial lipases, toxic mediators, and/or inflammatory mediators. All these factors reduce the quality and/or quantity of meibum the glands can release which in turn can cause chronic mechanical traumatization of the conjunctival, corneal and eyelid tissues which will lead to further tissue damage and the release of inflammatory mediators. Thus, many patients suffering from MGD also have inflammatory disease affecting their conjunctiva, cornea, larcrimal gland, lids or goblet cells causing comorbid conditions such as dry eye syndrome or blepharitis for which there is an unmet medical need.

For example, literature has used the terms posterior blepharitis and MGD as if they were synonymous, but these terms are not interchangeable. Posterior blepharitis describes inflammatory conditions of the posterior lid margin, of which MGD is only one possible cause. In its earliest stages, MGD may not be associated with clinical signs characteristic of posterior blepharitis. At this stage, affected individuals may be symptomatic, but alternatively, they may be asymptomatic and the condition regarded as subclinical. As MGD progresses, symptoms develop and lid margin signs, such as changes in meibum expressibility and quality and lid margin redness, may become more visible. At this point, an MGD-related posterior blepharitis is said to be present.

In certain embodiments, provided herein are methods of treating ocular (or dermatological) disorders associated with keratosis (e.g., lid keratosis, surface ocular keratosis, and/or gland blockage—such as in MGD), microbial infiltration/infection (e.g., bacterial infiltration/infection), and/or inflammation (such as inflammation associated keratosis or not associated with keratosis). In certain instances, disorders of the skin and/or eye (and/or surround tissue/skin) are difficult to differentially diagnose and/or have multiple etiologies. For example, in some instances, it can be difficult to distinguish between ocular disorders that involve (1) inflammation only, (2) inflammation associated with keratolytic activity, (3) inflammation associated with both keratolytic activity (e.g., inducing keratosis) and microbial infiltration, (4) keratolytic activity, but not inflammation and/or microbial infiltration, or various other combinations. In some instances, compounds and compositions provided herein can be used in such ocular and/or dermatological indications without the need for differential diagnosis (which can be difficult, e.g., because of similar symptom scores, etc.). Further, many ocular and/or dermatological disorders involve multiple etiologies, such inflammation, microbial infiltration, keratolytic activity, or various combinations thereof. As a result, therapeutic agents, such as those described herein, that target multiple etiologies are beneficial in providing therapeutic efficacy, such as by targeting both an underlying condition (e.g., keratolytic activity and/or microbial infiltration) and a symptom, such as inflammation or dry eye.

As such, provided herein are compounds, compositions, methods, and formulations for the treatment of ocular (e.g., periocular) or dermatological disorders, such as those having abnormalities having multifactorial etiologies. In specific embodiments, ocular disorders include, by way of non-limiting example, surface disorders, such as MGD, dry eye and associated inflammatory and bacterial disease.

In certain embodiments, provided herein are compounds having the structure of Formula (Ia):

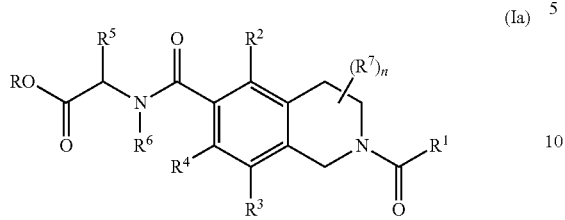

wherein

R$^1$ is aryl, cycloalkyl, heterocyclyl, or heteroaryl, wherein the aryl, cycloalkyl, heterocyclyl, or heteroaryl is optionally substituted;

R$^2$, R$^3$, and R$^4$ are each independently H, cyano, halo, ester, alkoxy, alkyl, heteroalkyl, cycloalkyl or heterocyclyl, wherein the alkoxy, alkyl, heteroalkyl, cycloalkyl or heterocyclyl is optionally substituted;

R$^5$ is -L-R$^{5a}$, wherein L is a bond, alkyl, or heteroalkyl, and R$^{5a}$ is absent, a cycloalkyl, a heterocycloalkyl, an aryl, or a heteroaryl, wherein the cycloalkyl, heterocycloalkyl, aryl or heteroaryl is optionally substituted;

R$^6$ is H, alkyl, or heteroalkyl;

each R$^7$ is independently H, cyano, halo, alkoxy, alkyl, heteroalkyl, cycloalkyl or haloalkyl;

n is 0-6;

R is -L'-D, wherein:

D is a keratolytic agent (e.g., radical thereof); and

L' is a linker, or a pharmaceutically acceptable salt or solvate thereof.

In some embodiments, L' comprises one or more linker groups, each linker group being selected from the group consisting of a bond, —O—, —S—, halo, alkyl (alkylenyl), heteroalkyl (heteroalkylenyl), disulfide, ester, and carbonyl (>C=O). In some embodiments, each linker group is selected from the group consisting of a bond, —O—, —S—, halo, alkyl (alkylenyl), heteroalkyl (heteroalkylenyl), and ester. In some embodiments, each linker group is selected from alkyl (alkylene) and heteroalkyl (heteroalkylene), the alkyl (alkylene) or heteroalkyl (heteroalkylene) being optionally substituted. In some embodiments, L' is alkyl (alkylene) substituted with oxo and one or more of alkyl and heteroalkyl. In some embodiments, the alkyl or heteroalkyl is substituted with one or more halo, alkyl, or haloalkyl. In some embodiments, the alkyl or heteroalkyl is substituted with one or more alkyl or haloalkyl. In some embodiments, L' is a bond, —O—, —S—, halo, (C=O), —(C=O)alkyl-, —(C=O)heteroalkyl-, —(C=O)O—, —(C=O)Oalkyl-, —(C=O)Oheteroalkyl-, —(C=O)S—, —(C=O)Salkyl-, —(C=O)Sheteroalkyl-, alkylene, or heteroalkylene, where each alkyl, heteroalkyl, alkylene, or heteroalkyl is optionally substituted. In some embodiments, L' is (C=O), —(C=O) alkyl-, —(C=O)heteroalkyl-, —(C=O)O—, —(C=O) Oalkyl-, —(C=O)Oheteroalkyl-, —(C=O)S—, —(C=O) Salkyl-, —(C=O)Sheteroalkyl-, alkylene, or heteroalkylene.

In some embodiments, the linker comprises the structure of Formula (A):

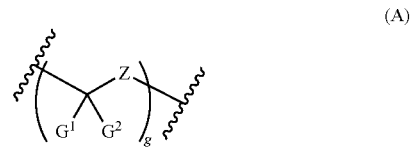

wherein:

Z is a bond, —O—, —S—, or optionally substituted amino;

G$^1$ and G$^2$ are each independently hydrogen, halo, alkyl, heteroalkyl, or cycloalkyl, wherein the alkyl or cycloalkyl is optionally substituted; and g is 1-20.

In some embodiments, the compound comprises more than one linker of Formula (A). In some embodiments, Z is a bond or —O—. In some embodiments, Z is a bond and G$^1$ and G$^2$ are each independently hydrogen, alkyl, or cycloalkyl, wherein the alkyl or cycloalkyl are optionally substituted. In some embodiments, Z is —O— and G$^1$ and G$^2$ are each independently hydrogen, alkyl, or cycloalkyl, wherein the alkyl or cycloalkyl are optionally substituted. In some embodiments, Z is a bond or —O— and G$^1$ is hydrogen and G$^2$ is alkyl or haloalkyl. In some embodiments, Z is a bond or —O— and G$^1$ is hydrogen and G$^2$ is methyl. In some embodiments, Z is a bond or —O— and G$^1$ and G$^2$ are each independently hydrogen. In some embodiments, Z is a bond and G$^1$ is hydrogen and G$^2$ is methyl. In some embodiments, Z is a bond and G$^1$ and G$^2$ are each independently hydrogen. In some embodiments, Z is —O—, G$^1$ is hydrogen and G$^2$ is methyl. In some embodiments, Z is —O— and G$^1$ and G$^2$ are each independently hydrogen.

In some embodiments, g is 1-20. In some embodiments, g is 1-10. In some embodiments, g is 1-5. In some embodiments, g is 2. In some embodiments, g is 1.

In some embodiments, g is 1 or 2, Z is a bond and G$^1$ is hydrogen, and G$^2$ is methyl. In some embodiments, g is 1 or 2, Z is a bond, and G$^1$ and G$^2$ are each independently hydrogen. In some embodiments, g is 1 or 2, Z is —O—, G$^1$ is hydrogen, and G$^2$ is methyl. In some embodiments, g is 1 or 2, Z is —O—, and G and G$^2$ are each independently hydrogen.

In some embodiments, the linker is selected from one or more of the group consisting of a bond, —O—, methylene,

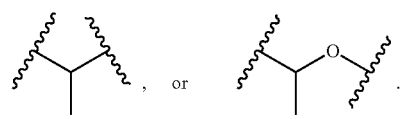

In some embodiments, the linker is a bond, methylene,

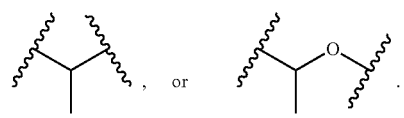

In some embodiments, D is selected from alkyl and heteroalkyl, the alkyl or heteroalkyl being optionally substituted. In some embodiments, D is alkyl substituted with oxo and one or more of the group selected from substituted alkyl and substituted heteroalkyl. In some embodiments, the alkyl is substituted with one or more of the group selected from —SH, —OH, substituted or unsubstituted aryl, substituted or unsubstituted heteroalkyl, or substituted or unsubstituted heterocycloalkyl. In some embodiments, D is heteroalkyl substituted with oxo and one or more of the group selected from substituted alkyl and substituted heteroalkyl. In some embodiments, the heteoralkyl is substituted with one or more of the group selected from —SH, —OH, or substituted or unsubstituted heteroalkyl. In some embodiments, the heteroalkyl is substituted with one or more of the group selected from —SH, —OH, alkyl, (C═O)alkyl, (C═O)heteroalkyl, and —NH(C═O)alkyl.

In some embodiments, D is selected from one or more of the group consisting of —CH$_2$OH, —CH(CH$_3$)OH, —CH$_2$(OCH$_2$CH$_2$)$_4$OH, —CH$_2$CH$_2$(OCH$_2$CH$_2$)$_4$OH,

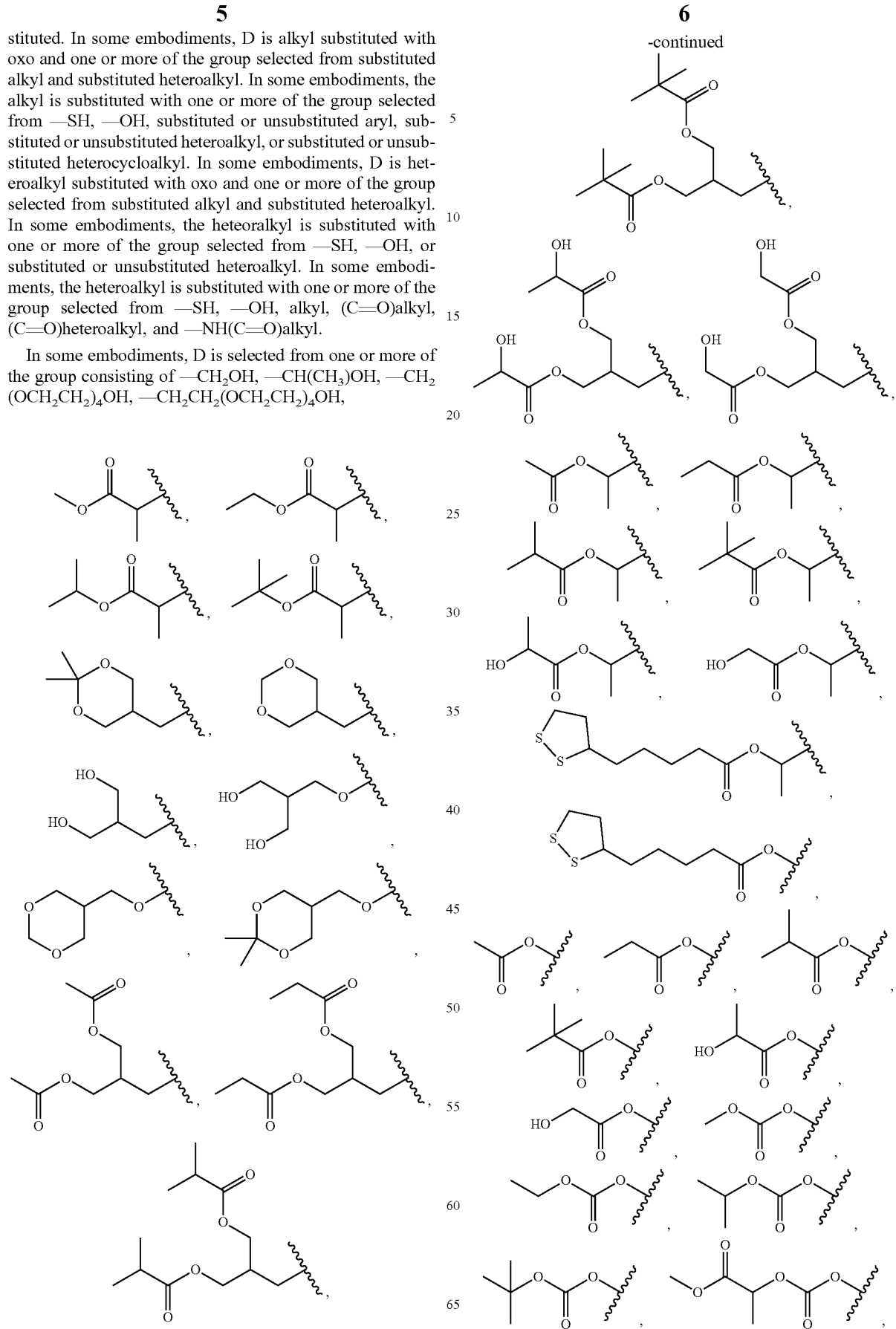

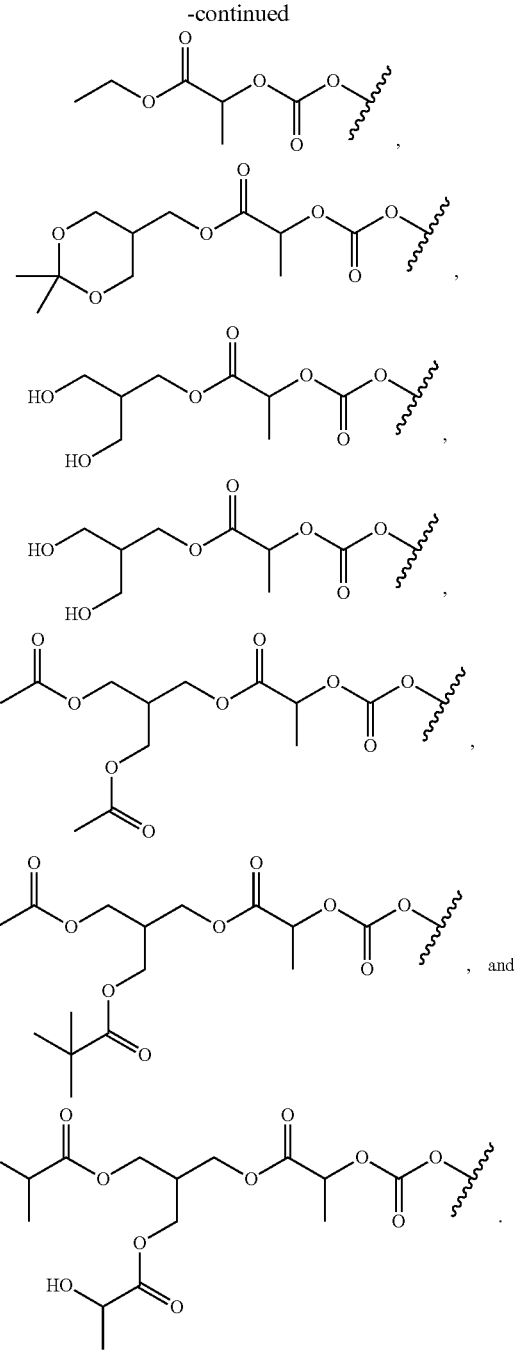
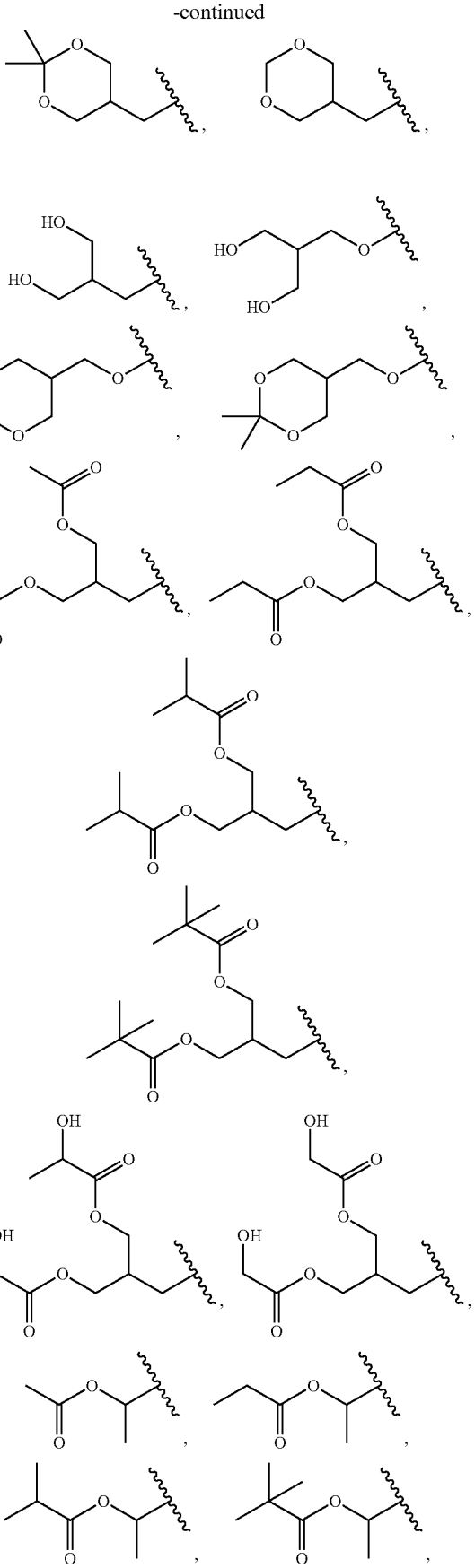
In some embodiments, D is —CH₂OH, —CH(CH₃)OH, —CH₂(OCH₂CH₂)₄OH, —CH₂CH₂(OCH₂CH₂)₄OH,

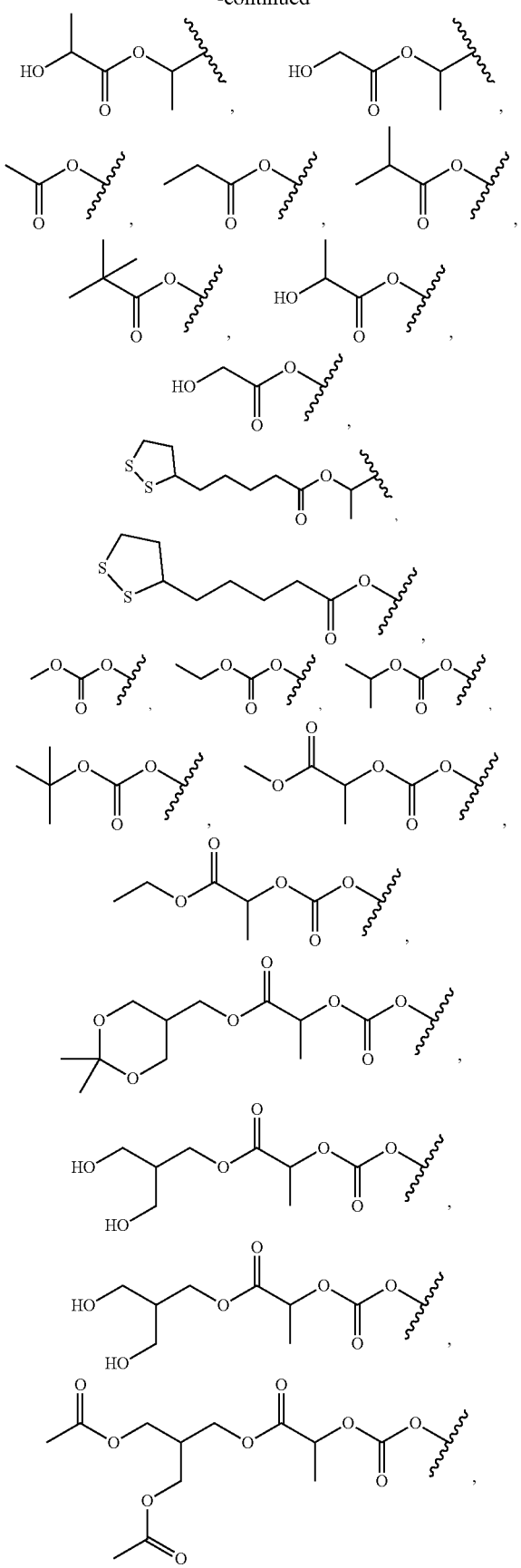
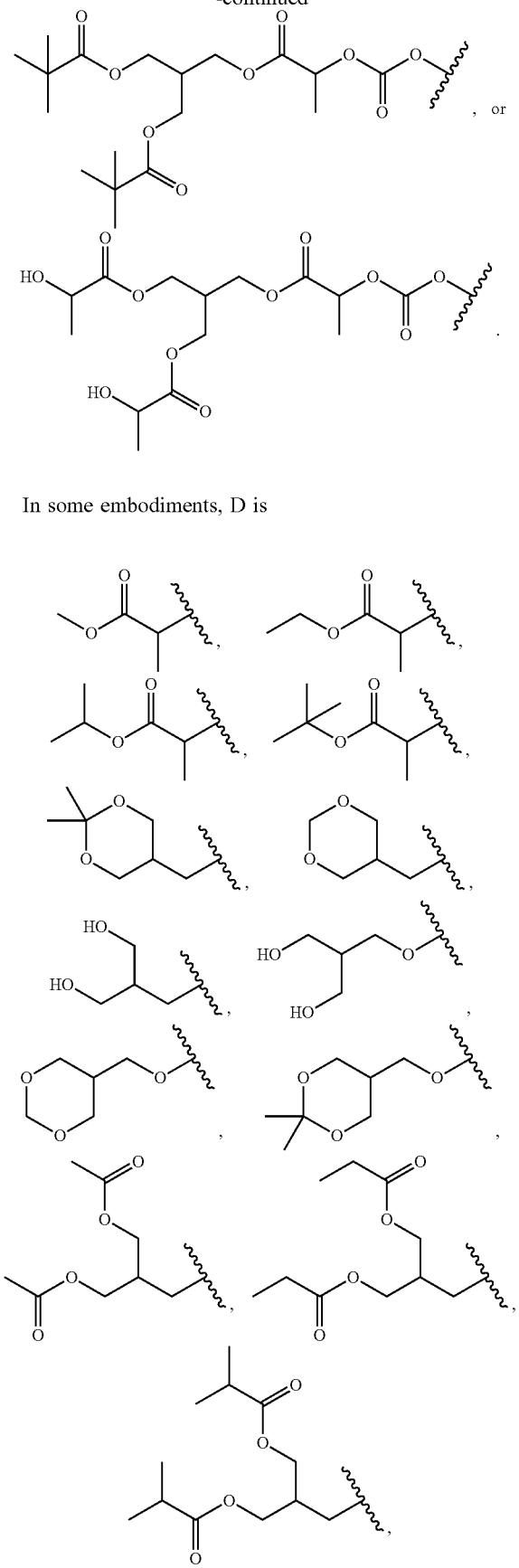
In some embodiments, D is

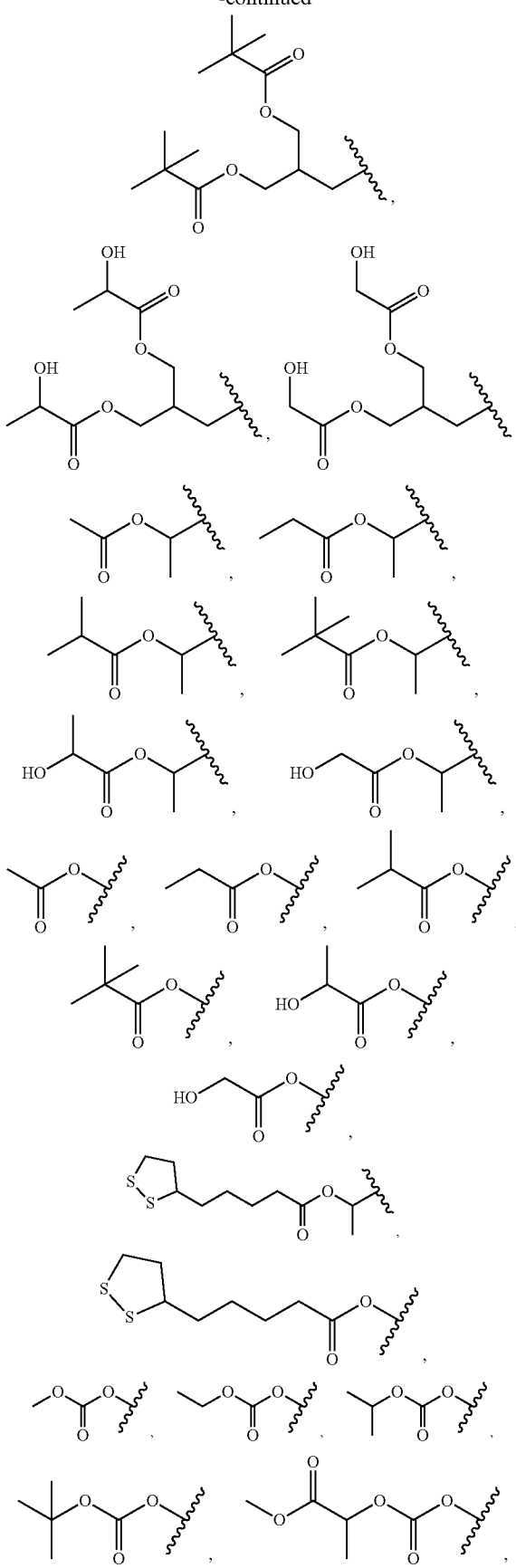
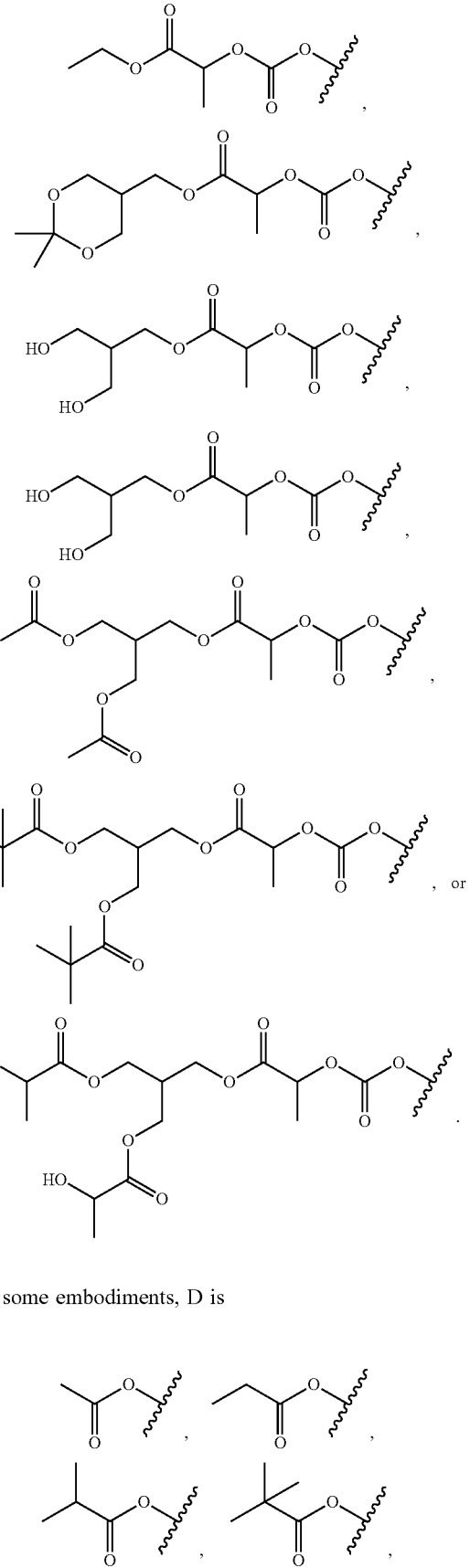
In some embodiments, D is

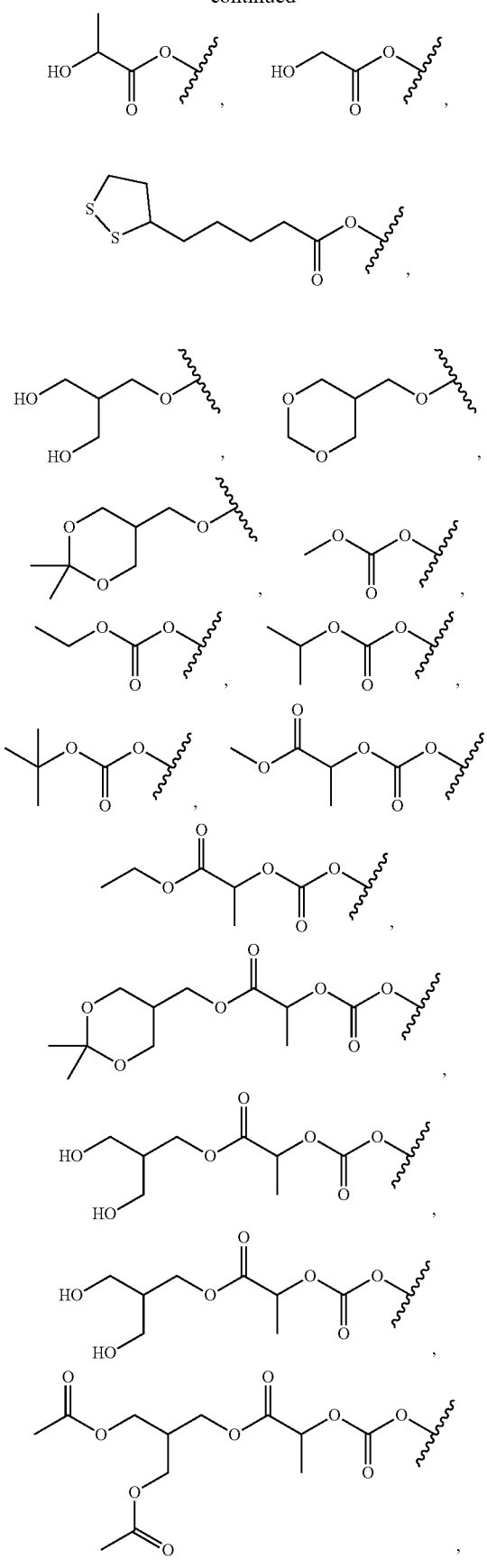

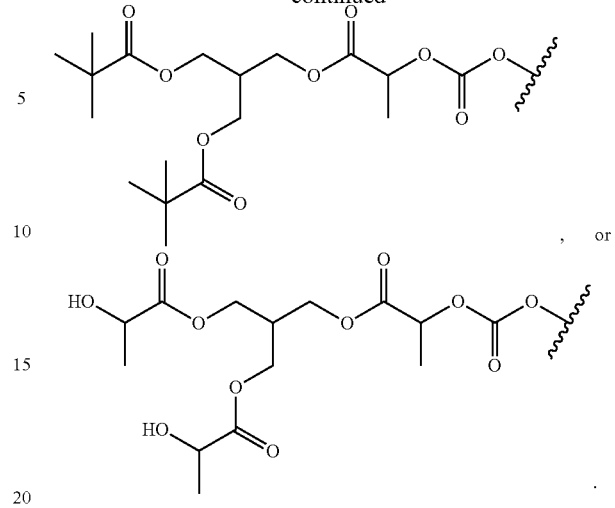

In some embodiments, D or the keratolytic agent is

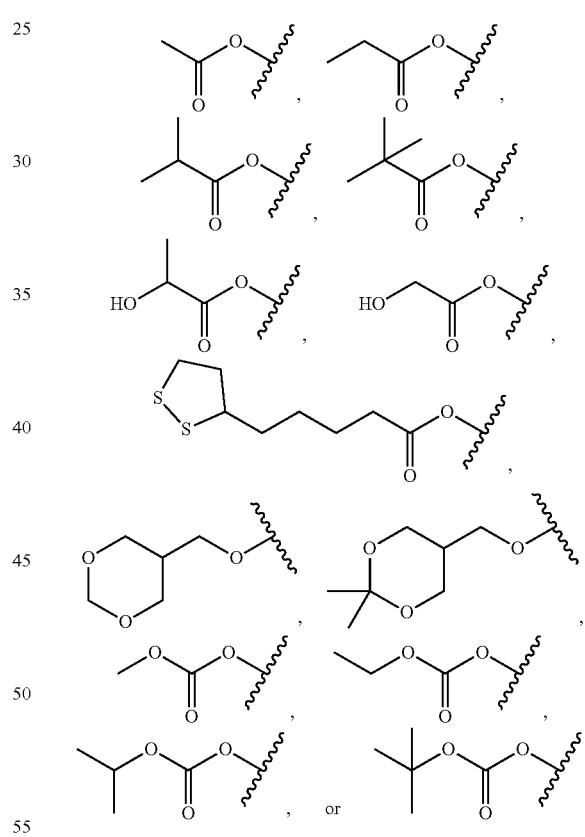

In some embodiments, D is a "keratolytic agent" radical that, upon release, hydrolysis, or other mechanism metabolizes or otherwise produces (e.g., when administered to an individual or patient, such as in or around the eye, such as the eyelid margin) an active keratolytic agent. In some instances, upon release (e.g., by hydrolysis or other mechanism), D produces a plurality of active keratolytic agents. In some instances, the active keratolytic agent comprises one or more of —SH, —OH, COOH (or COO—), or disulfide. In some embodiments, the active keratolytic agent is a carboxylic acid. In some embodiments, the active keratolytic agent is selected from the group consisting of acetic acid, glycolic acid, lactic acid, lipoic acid, pivalic acid, isobutryic acid, butyric acid, propionic acid, formic acid, and carbonic acid. In some embodiments, the active keratolytic agent is a thiol.

In some embodiments, L is attached to D by a bond.

In certain instances, combination of an anti-inflammatory and/or anti-microbial moiety (e.g., having a structure of any formula provided herein, minus the R') with a keratolytic moieity (e.g., being represented by and/or having a structure of D). In certain embodiments, such moieties are radicals connected by a linker that is a bond, with the keratolytic moiety being hydrolyzable to produce both (1) an anti-inflammatory and/or anti-microbial agent and (2) one or more active keratolytic agent. In some embodiments, such moieties are radicals connected by a hydrolyzable linker, with the hydrolyzable linker being hydrolyzable, such that both (1) an anti-inflammatory and/or anti-microbial agent and (2) one or more active keratolytic agent are released (e.g., in vivo, such as after therapeutic (e.g., topical) delivery to the eye and/or skin).

In certain embodiments, provided herein are compounds having the structure of Formula (Ia):

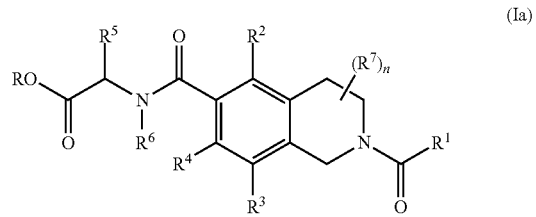

(Ia)

wherein $R^1$ is aryl, cycloalkyl, heterocyclyl, or heteroaryl, wherein the aryl, cycloalkyl, heterocyclyl, or heteroaryl is optionally substituted;

$R^2$, $R^3$, and $R^4$ are each independently H, cyano, halo, ester, alkoxy, alkyl, heteroalkyl, cycloalkyl or, heterocyclyl, wherein the alkoxy, alkyl, heteroalkyl, cycloalkyl or, heterocyclyl is optionally substituted;

$R^5$ is -L-$R^{5a}$, wherein L is a bond, alkyl, or heteroalkyl, and $R^{5a}$ is absent, a cycloalkyl, a heterocycloalkyl, an aryl, or a heteroaryl, wherein the cycloalkyl, heterocycloalkyl, aryl, or heteroaryl is optionally substituted;

$R^6$ is H, alkyl, or heteroalkyl;

each $R^7$ is independently H, cyano, halo, alkoxy, alkyl, heteroalkyl, cycloalkyl, or haloalkyl;

n is 0-6; and

R is alkyl or heteroalkyl substituted with at least one oxo, and further optionally substituted, or a pharmaceutically acceptable salt or solvate thereof.

In some embodiments, $R^1$ is optionally substituted aryl, heteroaryl, cycloalkyl, or heterocyclyl. In some embodiments, $R^1$ is optionally substituted aryl or heteroaryl. In some embodiments, $R^1$ is heteroaryl. In some embodiments, $R^1$ is benzofuran. In some embodiments, $R^1$ is

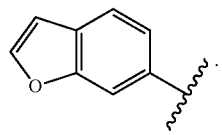 [SMILES: *c1ccc2ccoc2c1]

In some embodiments, $R^2$ and $R^4$ are each independently H, halo, alkoxy, or alkyl. In some embodiments, $R^2$ and $R^4$ are each independently H, halo, or alkyl. In some embodiments, $R^2$ and $R^4$ are halo. In some embodiments, $R^2$ and $R^4$ are each independently chloro. In some embodiments, $R^3$ is H, alkyl, halo, heteroalkyl, or cycloalkyl. In some embodiments, $R^3$ is H, alkyl, or halo. In some embodiments, $R^3$ is H. In some embodiments, $R^2$ and $R^4$ are each independently chloro and $R^3$ is H.

In some embodiments, L is a bond. In some embodiments, L is a bond and $R^{5a}$ is an optionally substituted aryl or heteroaryl. In some embodiments, L is alkyl and $R^{5a}$ is absent. In some embodiments, L is alkyl and $R^{5a}$ is optionally substituted aryl or optionally substituted heteroaryl. In some embodiments, $R^5$ is optionally substituted aryl, heteroaryl, aryl-alkyl, or heteroaryl-alkyl. In some embodiments, $R^5$ is optionally substituted aryl-alkyl or heteroaryl-alkyl. In some embodiments, $R^5$ is substituted aryl-alkyl or heteroaryl-alkyl. In some embodiments, $R^5$ is substituted aryl-alkyl. In some embodiments, $R^5$ is a sulfonyl substituted aryl-alkyl. In some embodiments, $R^5$ is a monosulfonyl substituted aryl-alkyl. In some embodiments, the sulfonyl substituent is methyl sulfone. In some embodiments, $R^5$ is

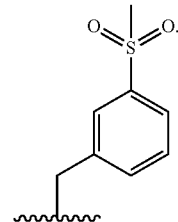 [SMILES: *Cc1cccc(S(C)(=O)=O)c1]

In some embodiments, $R^6$ is heteroalkyl. In some embodiments, $R^6$ is —(C=O)alkyl or —(C=O)heteroalkyl. In some embodiments, $R^6$ is alkyl. In some embodiments, $R^6$ is H.

In some embodiments, each $R^7$ is independently H, halo, alkyl, heteroalkyl, or cycloalkyl. In some embodiments, each $R^7$ is independently H, halo, or alkyl. In some embodiments, n is 1 and $R^7$ is halo or alkyl. In some embodiments, n is 2 and $R^7$ is independently halo or alkyl. In some embodiments, n is 0.

In some embodiments, $R^1$ is heteroaryl, $R^2$ and $R^4$ are each independently halo, and $R^5$ is a substituted aryl-alkyl. In some embodiments, $R^1$ is heteroaryl, $R^2$ and $R^4$ are each independently halo, $R^3$ is H, $R^5$ is a substituted aryl-alkyl, $R^6$ is H or alkyl, and n is 0. In some embodiments, $R^1$ is benzofuran, $R^2$ and $R^4$ are each independently halo, $R^3$ is H, $R^5$ is a sulfonyl substituted aryl-alkyl, $R^6$ is H, and n is 0. In some embodiments, R is benzofuran, $R^2$ and $R^4$ are each chloro, $R^3$ is H, $R^5$ is a sulfonyl mono-substituted aryl-alkyl, $R^6$ is H, and n is 0. In some embodiments, $R^1$ is:

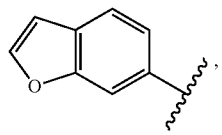

$R^2$ and $R^4$ are each chloro, $R^3$ is H, $R^5$ is:

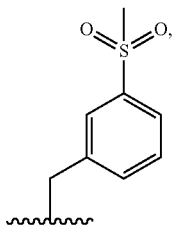

$R^6$ is H, and n is 0.

In some embodiments, the compound has the structure of Formula (Ib):

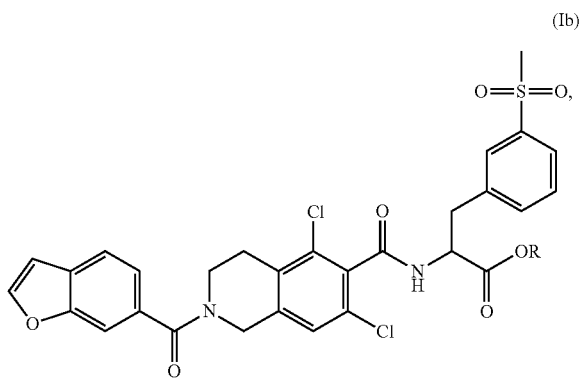

(Ib)

or a pharmaceutically acceptable salt thereof.

In some embodiments, the alkyl or heteroalkyl of R is substituted with one or more substituent, each substituent independently selected from the group consisting of alkyl, heteroalkyl, hydroxyl, thiol, thioether, disulfide, seleno, selenol, selenide, diselenide, sulfone, amide, halo, oxo, heterocyclyl, and cycloalkyl, wherein the heterocyclyl, and cycloalkyl is optionally substituted (e.g., with one or more substituent selected from the group consisting of alkyl, heteroalkyl, hydroxyl, thiol, thioether, disulfide, selenol, selenide, diselenide, sulfone, amide, halo and oxo). In some embodiments, the alkyl of R is substituted with one or more substituent, each substituent independently selected from alkyl, oxo, heteroalkyl, haloalkyl, hydroxyl, thiol, thioether, disulfide, and heterocycloalkyl.

In some embodiments, R is:

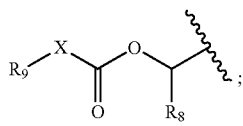

X is —O— or a bond;
$R^1$ is hydrogen, alkyl, heteroalkyl, or haloalkyl;
$R^9$ is alkyl or heteroalkyl, the alkyl or heteroalkyl being optionally substituted,
or a pharmaceutically acceptable salt or solvate thereof.

In some embodiments, X is —O— and $R^8$ is alkyl or haloalkyl. In some embodiments, X is —O— and $R^8$ is alkyl. In some embodiments, X is —O— and $R^8$ is methyl. In some embodiments, X is a bond and $R^8$ is alkyl or haloalkyl. In some embodiments, X is a bond and $R^8$ is alkyl. In some embodiments, X is a bond and $R^8$ is methyl.

In some embodiments, the compound has the structure of Formula (Ic):

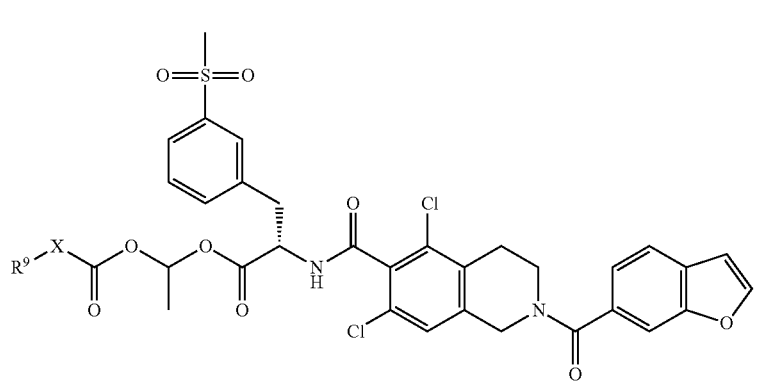

(Ic)

or a pharmaceutically acceptable salt or solvate thereof.

In some embodiments, X is a bond. In some embodiments X is —O—. In some embodiments, X is a bond or —O— and the alkyl or heteroalkyl of $R^9$ is substituted with one or more substituent, each substituent independently selected from the group consisting of alkyl, heteroalkyl, hydroxyl, thiol, thioether, disulfide, seleno, selenol, selenide, diselenide, sulfone, amide, ester, carboxylic acid, halo, oxo, heterocyclyl, and cycloalkyl, wherein the heterocyclyl, and cycloalkyl is optionally substituted (e.g., with one or more substituent selected from the group consisting of alkyl, heteroalkyl, hydroxyl, thiol, thioether, disulfide, selenol, sulfone, amide, ester halo and oxo). In some embodiments, the alkyl or heteroalkyl of $R^9$ is substituted with one or more substituent, each substituent independently selected from the group consisting of alkyl, heteroalkyl, hydroxyl, thiol, thioether, disulfide, ester, oxo, and heterocyclyl.

In some embodiments, X is —O— and $R^9$ is $C_{1-6}$ alkyl, —$(CR^dR^e)_p(C=O)O(C_1-C_6$-alkyl), —$(CR^dR^e)_p$carbocyclyl, —$(CR^dR^e)_p$heterocyclyl, or

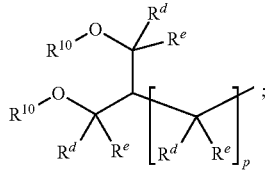

and $R^d$ and $R^e$ are each independently H, halo, alkyl, alkoxy, hydroxyl, thioether, sulfide, thiol, disulfide, seleno, heteroalkyl, carbocyclyl, carbocyclylalkyl, carbocyclylalkoxy, carboxyl, heterocyclyl, heterocyclylalkyl, or heterocyclylalkoxy;

$R^{10}$ is H, —$(C=O)C_{1-6}$ alkyl, or each $R^{10}$ combines to form an optionally substituted heterocycloalkyl;

p is 1 to 6; and wherein $C_{1-6}$ alkyl is optionally substituted with halo, alkyl, heteroalkyl, alkoxy, hydroxyl, thiol, disulfide, selenide, diselenide, amide, heterocyclyl or heterocyclylalkyl.

In some embodiments, X is —O— and $R^9$ is $C_{1-6}$ alkyl. In some embodiments, the $C_{1-6}$ alkyl is optionally substituted with alkyl, heteroalkyl, alkoxy, hydroxyl, heterocyclyl, or heterocyclylalkyl.

In some embodiments, X is —O— and $R^9$ is

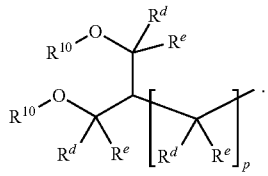

In some embodiments, each $R^{10}$ is independently hydrogen or —$(C=O)C_{1-6}$ alkyl. In some embodiments, each $R^{10}$ is hydrogen. In some embodiments, each $R^{10}$ is —$(C=O)$ $C_{1-6}$ alkyl. In some embodiments, the alkyl of —$(C=O)C_{1-6}$ alkyl is methyl, ethyl, propyl, isopropyl, or tert-butyl. In some embodiments, the alkyl of —$(C=O)C_{1-6}$ alkyl is methyl. In some embodiments, the alkyl of —$(C=O)C_{1-6}$ alkyl is ethyl. In some embodiments, the alkyl of —$(C=O)$ $C_{1-6}$ alkyl is propyl. In some embodiments, the alkyl of —$(C=O)C_{1-6}$ alkyl is isopropyl. In some embodiments, the alkyl of —$(C=O)C_{1-6}$ alkyl is tert-butyl.

In some embodiments, each $R^{10}$ are taken together to form an optionally substituted heterocycloalkyl. In some embodiments, each $R^d$ and $R^e$ is independently hydrogen, halo, or alkyl. In some embodiments, each $R^d$ and $R^e$ is hydrogen. In some embodiments, p is 1-5. In some embodiments, p is 1-3. In some embodiments, p is 1 or 2. In some embodiments, p is 1. In some embodiments, the heterocycloalkyl is 2,2-dimethyl-1,3-dioxane, 2-methyl-1,3-dioxane, or 1,3-dioxane.

In some embodiments, X is a bond and $R^9$ is $C_{1-6}$ alkyl, heteroalkyl or heterocyclylalkyl, wherein the $C_{1-6}$ alkyl may be linear or branched and is optionally substituted with halo, alkyl, heteroalkyl, alkoxy hydroxyl, thiol, disulfide, selenide, diselenide, amide, heterocyclyl or heterocyclylalkyl. In some embodiments, X is a bond and $R^9$ is heteroalkyl. In some embodiments, X is a bond and the heteroalkyl is —(C=O)alkyl, wherein the alkyl is optionally substituted with —OH or heterocycloalkyl. In some embodiments, the heterocycloalkyl is a dithiolane.

In some embodiments, X is bond or —O— and $R^9$ is methyl, ethyl, propyl, isopropyl, butyl, isobutyl, sec-butyl or tert-butyl.

In some embodiments, X is a bond and $R^9$ is —$CH_2OH$, —$CH(CH_3)OH$, —$CH_2(OCH_2CH_2)_4OH$, —$CH_2CH_2(OCH_2CH_2)_4OH$ In some embodiments, X is —O— and $R^9$ is

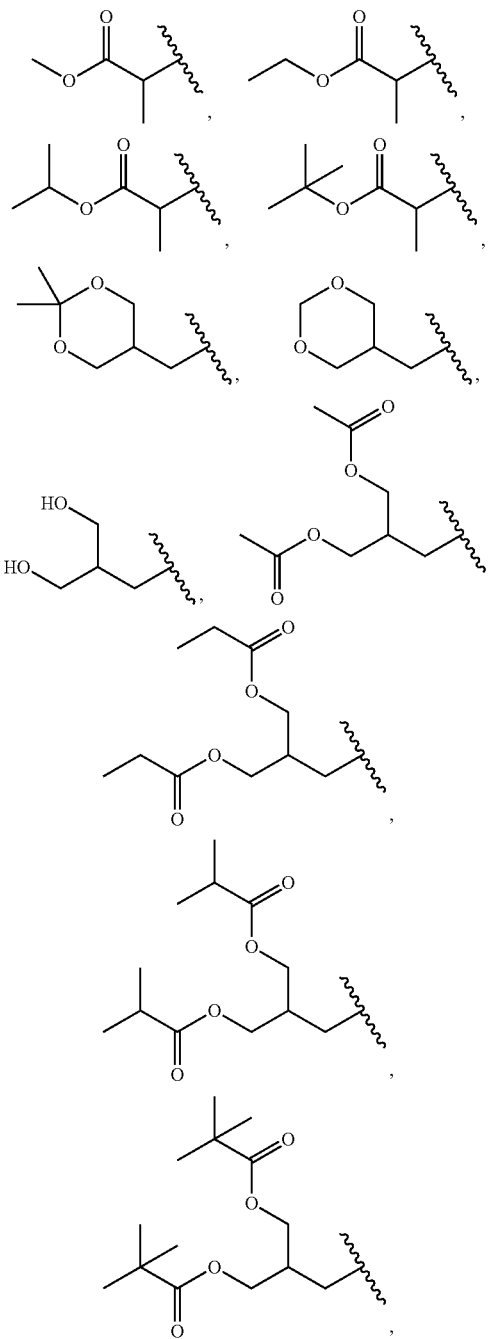

-continued

[Structures showing lactate ester and glycolate ester substituents], or

In some embodiments, R⁹ is methyl, ethyl, propyl, isopropyl, butyl, isobutyl, sec-butyl, tert-butyl, $CH_2OH$,

[isopropanol substituent], [lipoic acid-type dithiolane substituent], or

[dithiolane substituent].

One embodiment provides a compound, or a pharmaceutically acceptable salt thereof, having the structure of Formula (I):

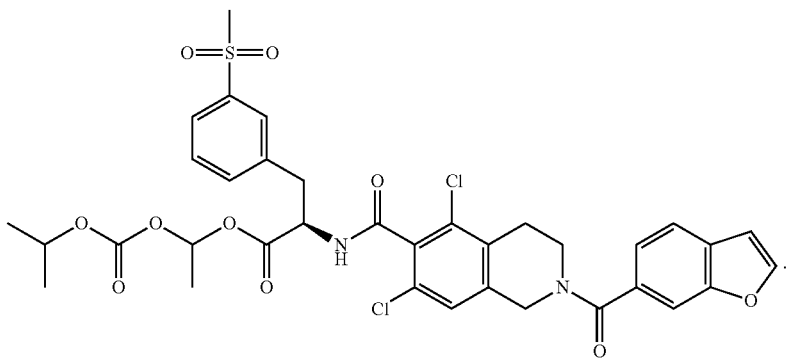

(I)

One embodiment provides a compound, or a pharmaceutically acceptable salt thereof, having the structure of Formula (I'):

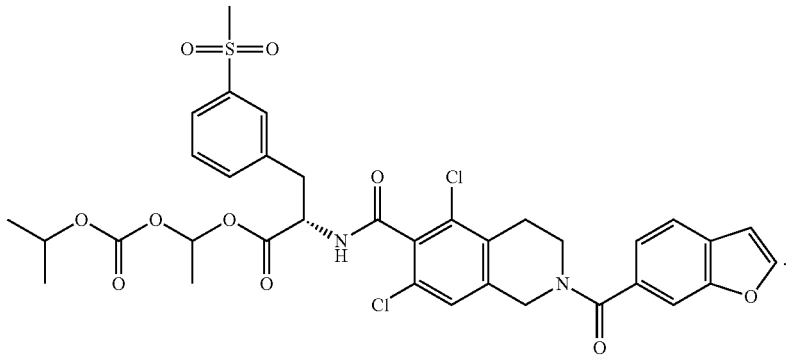

(I')

One embodiment provides a compound, or a pharmaceutically acceptable salt thereof, having the structure of Formula (II):

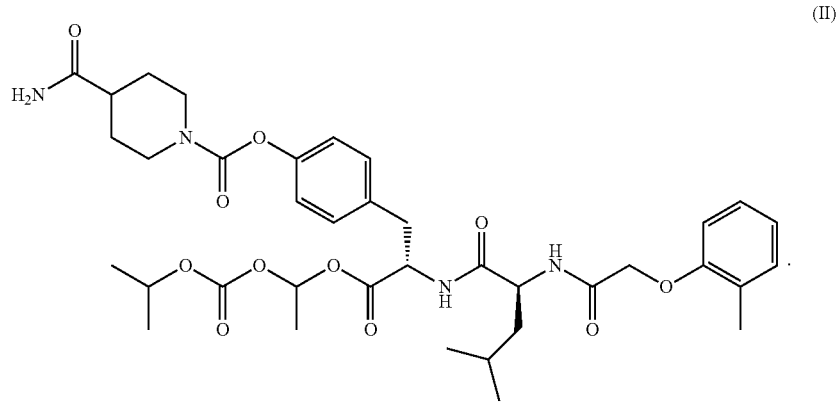 [SMILES: Cc1ccccc1OCC(=O)N[C@@H](CC(C)C)C(=O)N[C@@H](Cc1ccc(OC(=O)N2CCC(C(N)=O)CC2)cc1)C(=O)OC(C)OC(=O)OC(C)C]

One embodiment provides a pharmaceutical composition comprising any compound provided herein, such as a compound of any one of Formula (Ia), Formula (Ib), Formula (Ic), Formula (I), Formula (I'), or Formula (II), or a pharmaceutically acceptable salt thereof, and at least one pharmaceutically acceptable excipient. Another embodiment provides the pharmaceutical composition, wherein the pharmaceutical composition is suitable for ophthalmic administration. Another embodiment provides the pharmaceutical composition, wherein the pharmaceutical composition is suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

In some embodiments, a compound or a pharmaceutical composition comprising any compound provided herein, such as a compound of any one of Formula (Ia), Formula (Ib), Formula (Ic), Formula (I), Formula (I'), or Formula (II), or a pharmaceutically acceptable salt thereof, is substantially hydrolytically stable (e.g., stable in an aqueous composition (e.g., solution), such as a buffer solution or ophthalmically acceptable aqueous composition). In some embodiments, the compound or the pharmaceutical composition is formulated in an aqueous vehicle. In some embodiments, the compound or the pharmaceutical composition is formulated and stored in an aqueous vehicle. In some instances, compositions or formulations provided herein are chemically and/or physically stable in an aqueous composition.

In some embodiments, a compound provided herein, such as a compound of any one of Formula (Ia), Formula (Ib), Formula (Ic), Formula (I), Formula (I'), or Formula (II), or a pharmaceutically acceptable salt thereof, is hydrolyzed to an active pharmaceutical agent (e.g., a free form of a radical of Formula (Ia), Formula (Ib), Formula (Ic), Formula (I), Formula (I'), or Formula (II), such as wherein R is a negative charge or H) and a keratolytic agent. In some embodiments, the compound or pharmaceutical composition is hydrolyzed to an active pharmaceutical agent and a keratolytic agent in an ocular space. In some embodiments, the compound or pharmaceutical composition is hydrolyzed to an active pharmaceutical agent and a keratolytic agent by an esterase in an ocular space. In some embodiments, the active pharmaceutical agent is an anti-inflammatory agent. In some embodiments the anti-inflammatory agent is lifitegrast. In some embodiments, the keratolytic agent is a carboxylic acid. In some embodiments, the carboxylic acid is selected from the group consisting of acetic acid, glycolic acid, lactic acid, lipoic acid, pivalic acid, isobutryic acid, butyric acid, propionic acid, formic acid, and carbonic acid. In some embodiments, the active keratolytic agent is a thiol.

In some embodiments, a compound or a pharmaceutical composition comprising any compound provided herein, such as a compound of any one of Formula (Ia), Formula (Ib), Formula (Ic), Formula (I), Formula (I'), or Formula (II), or a pharmaceutically acceptable salt thereof. In certain embodiments, the composition further comprises an amount of a free form of a radical of any of Formula (Ia), Formula (Ib), Formula (Ic), Formula (I), Formula (I'), or Formula (II) or the like (such as wherein the free form is the radical, wherein R is a negative charge or an H). In some embodiments, a composition provided herein comprises a (e.g., weight or molar) ratio of a compound provided herein to a free form of a radical of Formula (Ia), Formula (Ib), Formula (Ic), Formula (I), Formula (I'), or Formula (II), or a pharmaceutically acceptable salt thereof (e.g., wherein R is a negative charge or an H) is about 1:99 to about 100:0 (e.g., the amount of the free form of the radical relative to the overall amount of free form of the radical plus the conjugate is between 0% (weight or molar) and 99%). In some embodiments, the relative amount of the free form of the radical is 0% to about 50%, such 0% to about 20%, 0% to about 10%, about 0.1% to about 10%, about 0.1% to about 5%, less than 5%, less than 2.5%, less than 2%, or the like (percentages being weight/weight or mole/mole percentages). In some instances, such aqueous compositions are pre-manufactured or are manufactured at the time of application in order to maintain high concentrations of the compound relative to the free form of a radical thereof. In some embodiments, such concentrations of the compound are present in the composition for at least 45 minutes in an aqueous composition (such as in an aqueous composition, e.g., a HEPES buffer, such as under the conditions described herein, such as in Tables 2 and 3). Tables 2 and 3 of the Examples illustrate good stability of the compositions provided herein and such recitations are incorporated in the disclosure hereof. Further, in some instances, compounds provided herein release free form of a radical of a compound of Formula (Ia), Formula (Ib), Formula (Ic), Formula (I), Formula (I'), or Formula (II) (e.g., wherein R is a negative charge or H), such as when administered to an individual (e.g., ocular (e.g., peri-ocular) or dermatological administration). In more specific instances, when administered to an individual at a location with esterases present, rapid release of active (free) forms of a radical of Formula (Ia), Formula (Ib), Formula (Ic), Formula (I), Formula (I'), or Formula (II) (e.g., wherein R is a negative charge or H) (and, a keratolytic agent and/or agent that further produces active keratolytic agent(s) (e.g., by further hydrolysis thereof)).

One embodiment provides a method of treating an ophthalmic disease or disorder in a patient in need of thereof, comprising administering to the patient a composition comprising any compound provided herein, such as a compound of any one of Formula (Ia), Formula (Ib), Formula (Ic), Formula (I), Formula (I'), or Formula (II), or a pharmaceutically acceptable salt thereof. Another embodiment provides the method wherein the ophthalmic disease or disorder is selected from dry eye, lid wiper epitheliopathy (LWE), contact lens discomfort (CLD), contact lens discomfort, dry eye syndrome, evaporative dry eye syndrome, aqueous deficiency dry eye syndrome, blepharitis, keratitis, meibomian gland dysfunction, conjunctivitis, lacrimal gland disorder, inflammation of the anterior surface of the eye, infection of the anterior surface of the eye, infection of the lid, demodex lid infestation, lid wiper epitheliopathy and autoimmune disorder of the anterior surface of the eye.

In certain embodiments, provided herein is a method of treating an ocular (e.g., peri-ocular) or dermatological indication (e.g., associated with keratolytic activity, inflammation, and/or microbial infiltration), the method comprising administering a therapeutically effective amount of a compound or composition provided herein. In some embodiments, a composition provided herein (e.g., used in a method provided herein) comprises a compound provided herein in a therapeutically effective amount (e.g., at a concentration effective to treat keratosis/keratolytic activity, inflammation, and/or microbial infiltration), in the eye, surrounding tissue, or skin. In certain embodiments, a (e.g., pharmaceutical and/or ophthalmic) composition provided herein comprises about 0.1 wt. % to about 10 wt. % of a compound provided herein.

Ocular and/or dermatological disorders include inflammatory conditions of the eyelids (e.g., hordeolum (stye), blepharitis, and chalazion), ocular surface (e.g., dry eye disease and anterior uveitis) and posterior eye (e.g., posterior and pan-uveitis), abnormalities of the peri-ocular glands (e.g., meibomian gland dysfunction (MGD)), allergic-type conditions, (e.g., eczema, atopic dermatitis, atopic keratoconjunctivitis refractory to topical steroid treatment, and vernal keratoconjunctivitis), surgical complications (e.g., corneal transplant rejection, post-corneal transplant glaucoma, cataracts secondary to phakic corneal transplant, fungal infections in keratoplasty patients, and post-LASIK dry eye and/or poor refractive outcomes), corneal abnormalities (e.g., inflammatory corneal ulceration, rheumatoid corneal ulcers, and Thygeson's superficial punctate keratitis), conjunctival abnormalities (e.g., iridocyclitis, ligneous conjunctivitis), ocular complications from systemic treatments and/or autoimmune diseases (e.g., pauciarticular juvenile rheumatoid arthritis, graft versus host disease, and sjogren's syndrome) and/or infectious disease of the anterior surface of the eye. Provided herein are compositions and methods for the treatment of ocular and periocular abnormalities that are known to have multifactorial etiologies and interactions.

One embodiment provides a compound having the structure of Formula (III):

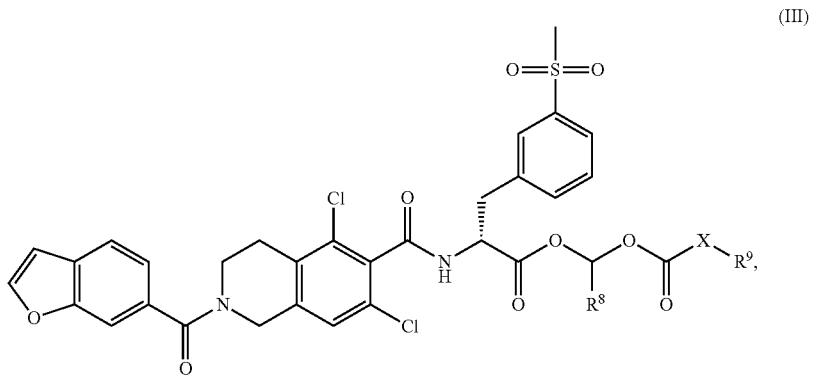

X is a bond or —O—;

$R^1$ is hydrogen, alkyl, heteroalkyl, or haloalkyl;

$R^9$ is alkyl or heteroalkyl, the alkyl or heteroalkyl being optionally substituted, or a pharmaceutically acceptable salt or solvate thereof.

In some embodiments, $R^8$ is hydrogen, alkyl, or haloalkyl. In some embodiments, $R^8$ is $C_1$-$C_4$ alkyl. In some embodiments, $R^8$ is methyl.

In some embodiments, X is a bond. In some embodiments, $R^9$ is alkyl optionally substituted with one or more substituent(s), each substituent being independently selected from the group consisting of —OH and optionally substituted alkyl. In some embodiments, the alkyl is substituted with alkyl or heterocycloalkyl. In some embodiments, the heterocycloalkyl is further optionally substituted. In some embodiments, $R^9$ is alkyl substituted with —OH. In some embodiments, $R^9$ is alkyl substituted with —OH and alkyl. In some embodiments, $R^9$ is alkyl substituted with a dithiolane. In some embodiments, $R^9$ is $C_1$-$C_4$ alkyl.

In some embodiments, $R^9$ is $C_1$-$C_4$ alkyl, —CH(CH$_3$)OH, —CH$_2$OH, or

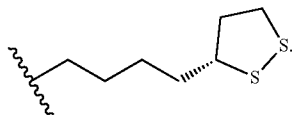 [SMILES: *CCCC[C@@H]1CCSS1]

In some embodiments, X is —O—. In some embodiments, $R^8$ is methyl and $R^9$ is alkyl further optionally substituted with one or more substituent(s), each substituent being independently selected from the group consisting of alkyl, heteroalkyl (e.g., hydroxymethyl or ester), and heterocycloalkyl, wherein the heteroalkyl (e.g., hydroxymethyl or ester) or heterocycloalkyl is further optionally substituted. In some embodiments, $R^9$ is alkyl further substituted with an optionally substituted 1,3-dioxane. In some embodiments, $R^9$ is alkyl further substituted with 1,3-dioxane. In some embodiments, $R^9$ is alkyl further substituted with 2,2-dimethyl-1,3-dioxane or 2-methyl-1,3-dioxane. In some embodiments, $R^9$ is alkyl further substituted with one or more heteroalkyl substituents. In some embodiments, the heteroalkyl substituent is —CH$_2$OH or —O(C=O)C$_1$-C$_4$ alkyl. In some embodiments, $R^9$ is alkyl further substituted with alkyl, wherein the alkyl is further substituted with an ester further substituted with alkyl, wherein the alkyl is further optionally substituted with one or more substituent(s), each substituent being independently selected from the group consisting of —OH and alkyl. In some embodiments, $R^9$ is $C_1$-$C_4$ alkyl. In some embodiments, $R^9$ is alkyl further substituted with methyl and —O(C=O)C$_1$-C$_4$ alkyl.

In some embodiments, $R^9$ is $C_1$-$C_4$ alkyl,

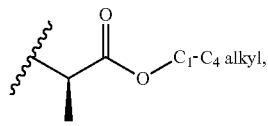

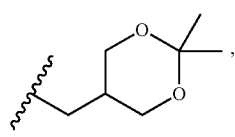

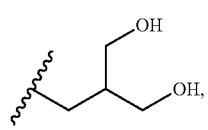

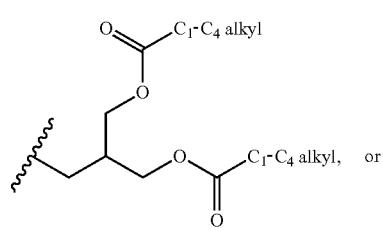

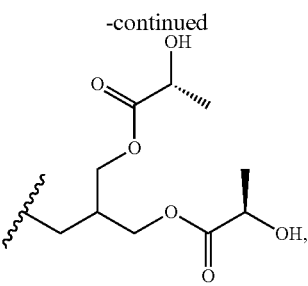

In some embodiments, $C_1$-$C_4$ alkyl is methyl, ethyl, propyl, isopropyl, or tert-butyl.

In certain embodiments, described herein is a method of treating a (e.g., ophthalmic or dermal) disease or disorder (e.g., any disease or disorder described herein) in an individual in need of thereof, comprising administering (e.g., topically to the eye and/or skin) to the individual a composition (e.g., any composition described herein) comprising any compound provided herein, such as a compound of any one of Formula (III), or a pharmaceutically acceptable salt thereof.

INCORPORATION BY REFERENCE

All publications, patents, and patent applications mentioned in this specification are herein incorporated by reference for the specific purposes identified herein.

DETAILED DESCRIPTION OF THE INVENTION

Certain Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms associated with a disease, disease sate, or indication (e.g., MGD) in either a chronic or acute therapeutic scenario. In one embodiment, treatment includes a reduction of a terminal duct obstruction. Also, treatment of a disease or disease state described herein includes the disclosure of use of such compound or composition for the treatment of such disease, disease state, or indication.

The term "opening" refers to the clearing (at least in part) of an obstructed meibomian gland canal or orifice and/or maintaining the patency of the meibomian gland canal or orifice.

The term "keratolytic agent" and/or "keratoplastic agent" as used herein refers to an agent that softens, disrupts, dissolves, solubilizes, or loosens a keratinized obstruction, or prevents the formation of a keratinized obstruction. Specifically, the term "keratolytic agents" refers to agents used to promote softening and dissolution of keratin and the term "keratoplastic agents" refers to agents used to reduce keratin production.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" generally refers to a straight or branched hydrocarbon chain radical consisting solely of carbon and hydrogen atoms, such as having from one to fifteen carbon atoms (e.g., $C_1$-$C_{15}$ alkyl). Unless otherwise state, alkyl is saturated or unsaturated (e.g., an alkenyl, which comprises at least one carbon-carbon double bond). Disclosures provided herein of an "alkyl" are intended to include independent recitations of a saturated "alkyl," unless otherwise stated. Alkyl groups described herein are generally monovalent, but may also be divalent (which may also be described herein as "alkylene" or "alkylenyl" groups). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. In general, alkyl groups are each independently substituted or unsubstituted. Each recitation of "alkyl" provided herein, unless otherwise stated, includes a specific and explicit recitation of an unsaturated "alkyl" group. Similarly, unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is optionally substituted as described for "alkyl" groups.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n-butylene, and the like. Unless stated otherwise specifically in the specification, an alkylene chain is optionally substituted as described for alkyl groups herein.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" or "aryl-alkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl or cycloalkyl is saturated (i.e., containing single C—C bonds only) or unsaturated (i.e., containing one or more double bonds or triple bonds). Examples of saturated cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkenyl" refers to a radical of the formula —$R^c$-carbocyclyl where $R^c$ is an alkenylene chain as defined above. The alkenylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

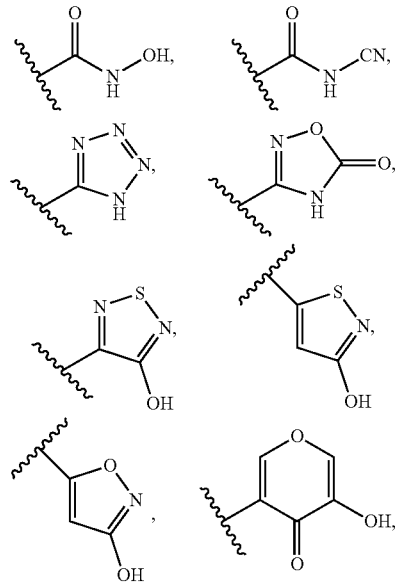

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

The term "heteroalkyl" refers to an alkyl group as defined above in which one or more skeletal carbon atoms of the alkyl are substituted with a heteroatom (with the appropriate number of substituents or valencies—for example, —CH$_2$— may be replaced with —NH— or —O—). For example, each substituted carbon atom is independently substituted with a heteroatom, such as wherein the carbon is substituted with a nitrogen, oxygen, selenium, or other suitable heteroatom. In some instances, each substituted carbon atom is independently substituted for an oxygen, nitrogen (e.g. —NH—, —N(alkyl)-, or —N(aryl)- or having another substituent contemplated herein), or sulfur (e.g. —S—, —S(=O)—, or —S(=O)$_2$—). In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a C$_1$-C$_{18}$ heteroalkyl. In some embodiments, a heteroalkyl is a C$_1$-C$_{12}$ heteroalkyl. In some embodiments, a heteroalkyl is a C$_1$-C$_6$ heteroalkyl. In some embodiments, a heteroalkyl is a C$_1$-C$_4$ heteroalkyl. Representative heteroalkyl groups include, but are not limited to —OCH$_2$OMe, or —CH$_2$CH$_2$OMe. In some embodiments, heteroalkyl includes alkoxy, alkoxyalkyl, alkylamino, alkylaminoalkyl, aminoalkyl, heterocycloalkyl, heterocycloalkyl, and heterocycloalkylalkyl, as defined herein. Unless stated otherwise specifically in the specification, a heteroalkyl group is optionally substituted as defined above for an alkyl group.

"Heteroalkylene" refers to a divalent heteroalkyl group defined above which links one part of the molecule to another part of the molecule. Unless stated specifically otherwise, a heteroalkylene is optionally substituted, as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) 7-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a, 7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)OR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, substituted groups may be substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The compounds disclosed herein, reference to any atom includes reference to isotopes thereof. For example reference to H includes reference to any isotope thereof, such as a $^1$H, $^2$H, $^3$H, or mixtures thereof.

"Pharmaceutically acceptable salt" includes both acid and base addition salts. A pharmaceutically acceptable salt of any one of the dual-acting meibomian gland dysfunction pharmacological agents described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Meibomian Gland

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and is only a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

The term "keratinized obstruction" as used herein refers to a blockage of the meibomian gland, regardless of the location of the blockage. In some embodiments, the blockage is complete, whereas in other embodiments, the blockage is partial. Regardless of the degree of blockage, such keratinized obstruction leads to meibomian gland dysfunction. In some embodiments, the keratinized obstruction is composed of keratinized material and lipids. In some embodiments, the keratinized obstruction is a blockage at the meibomian gland orifice and excretory duct. In some embodiments, the keratinized obstruction is caused by keratinization of the epithelium at the lid margin and meibomian gland. In certain instances, the keratin obstruction is influenced by the migration or aberrant differentiation of stem cells. In some embodiments, the keratinized obstruction results in reduced delivery of oil to the lid margin and tear film, and stasis inside the meibomian gland that causes increased pressure, resultant dilation, acinar atrophy, and low secretion. In certain instances, keratinization of the meibomian gland causes degenerative gland dilation and atrophy.

Ocular Surface Diseases or Disorders

Ocular surface diseases is a group of diseases including, but not limited to, dry eye syndrome (including evaporative DES and/or aqueous deficiency DES), blepharitis, keratitis, meibomian gland dysfunction, conjunctivitis, lacrimal gland disorder, contact lens related conditions and inflammatory, infectious, or autoimmune diseases or disorders of the anterior surface of the eye. The term, "meibomian gland dysfunction," as used herein, refers to chronic, diffuse abnormality of the meibomian glands, that is characterized by terminal duct obstruction or qualitative or quantitative changes in the glandular secretion, or both. MGD may result in alteration of the tear film, eye irritation symptoms, inflammation, or ocular surface disease. The most prominent aspects of MGD are obstruction of the meibomian gland orifices and terminal ducts and changes in the meibomian gland secretions.

In some instances, meibomian gland dysfunction (MGD) is a chronic, diffuse abnormality of the meibomian glands, commonly characterized by terminal duct obstruction and/or qualitative/quantitative changes in the glandular secretion. Terminal duct obstruction is caused by hyperkeratinization of the ductal epithelium (Nichols et al, Inv. Oph. & Vis. Sci. (2011); 52(4):1922-1929). These alterations in both meibum quality and expression may result in alteration of the tear film, symptoms of eye irritation, and ocular surface disease such as evaporative dry eye. The principal clinical consequence of MGD is evaporative dry eye syndrome and large population based studies (i.e., Bankok Study and the Shihpai Eye Study) estimate that over 60% of patients with dry eye symptoms also have MGD (Schaumberg et al, Investigative Ophthalmology and Visual Science. (2011); 52(4):1994-2005).

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye. An inadequate amount of lipids flowing from the meibomian glands as caused by a keratinized obstruction, may cause excessive evaporation, thereby causing dry eye syndrome.

In some embodiments, altered meibomian gland secretion is detected by physically expressing the meibomian glands by applying digital pressure to the tarsal plates. In subjects without MGD, the meibum is a pool of clear oil. In MGD, both the quality and expressibility of the expressed material is altered. The altered meibum is also known as meibomian excreta and is made up of a mixture of altered secretions and keratinized epithelial material. In MGD, the quality of expressed lipid varies in appearance from a clear fluid, to a viscous fluid containing particulate matter and densely opaque, toothpaste-like material. The meibomian orifices may exhibit elevations above surface level of the lid, which is referred to as plugging or pouting, and is due to obstruction of the terminal ducts and extrusion of a mixture of meibomian lipid and keratinized material.

Obstructive MGD is characterized by all or some of the following: 1) chronic ocular discomfort, 2) anatomic abnormalities around the meibomian gland orifice (which is one or more of the following: vascular engorgement, anterior or posterior displacement of the mucocutaneous junction, irregularity of the lid margin) and 3) obstruction of the meibomian glands (obstructive findings of the gland orifices by slit lamp biomicroscopy (pouting, plugging or ridge), decreased meibum expression by moderate digital pressure).

Current methods for assessing and monitoring MGD symptoms include, but are not limited to patient questionnaires, meibomian gland expression, tear stability break up time, and determining the number of patent glands as seen by digital expression.

In some embodiments, the symptoms of a patient are assessed by asking the patient a series of questions. Questionnaires allow the assessment of a range of symptoms associated with ocular discomfort. In some embodiments, the questionnaire is the SPEED questionnaire. The SPEED questionnaire assesses frequency and severity of a patient's dry eye symptoms. It examines the occurrence of symptoms on the current day, past 72 hours and past three months. A SPEED score is tallied based on the patient's answers to the questions, to give a range of severity of the patient's symptoms. The SPEED questionnaire includes questions such as the following: 1) what dry eye symptoms are you experiencing, and when do they occur? 2) how frequently do you experience dryness, grittiness, or scratchiness in your eyes? 3) how often do you experience soreness or irritation of the eyes? 4) how often do you experience burning or watering of the eyes?5) how often do you experience eye fatigue? and 6) how severe are the symptoms?

Meibomian gland expressibility is optionally determined to assess the meibomian gland function. In normal patients, meibum is a clear to light yellow oil. Meibum is excreted from the glands when digital pressure is placed on the glands. Changes in meibomian gland expressibility are one potential indicator of MGD. In some embodiments, during expression, quantifying the amount of physical force applied during expression is monitored in addition to assessing lipid volume and lipid quantity.

Tear stability break up time (TBUT) is a surrogate marker for tear stability. Tear film instability is a core mechanism in dry eye and MGD. Low TBUT implies a possibility of lipid layer compromise and MGD. TBUT is optionally measured by examining fluorescein breakup time, as defined as the time to initial breakup of the tear film after a blink. Fluorescein is optionally applied by wetting a commercially available fluorescein-impregnated strip with saline, and applied to the inferior fornix or bulbar conjuctiva. The patient is then asked to blink several times and move the eyes. The break up is then analyzed with a slit lamp, a cobalt blue filter, and a beam width of 4 mm. The patient is instructed to blink, and the time from upstroke of the last blink to the first tear film break or dry spot formation is recorded as a measurement.

Other methods for assessing MGD symptoms, include but are not limited to, Schirmer test, ocular surface staining, lid morphology analysis, meibography, meibometry, interferometry, evaporimetry, tear lipid composition analysis, fluorophotometry, meiscometry, osmolarity analysis, indices of tear film dynamics, evaporation and tear turnover.

Current treatments for MGD include lid warming, lid massage, lid hygiene, lid expression and meibomian gland probing. Pharmacological methods, prior to those described herein, have not been used.

Lid hygiene is considered the primary treatment for MGD and consists of three components: 1) application of heat, 2) mechanical massage of eyelids and 3) cleansing the eyelid. Eyelid warming procedures improve meibomian gland secretion by melting the pathologically altered meibomian lipids. Warming is achieved by warm compresses or devices. Mechanical lid hygiene includes the use of scrubs, mechanical expression and cleansing with various solutions of the eyelashes and lid margins. Lid margins are optionally also cleansed with hypoallergenic bar soap, dilute infant shampoo or commercial lid scrubs. Physical expression of meibomian glands is performed in a physician's office or is performed by the patient at home. The technique varies from gentle massage of the lids against the eyeball to forceful squeezing of the lids either against each other or between a rigid object on the inner lid surface and a finger, thumb, or rigid object (such as a glass rod, cotton swab, or metal paddle) on the outer lid surface. The rigid object on the inner lid surface protects the eyeball from forces transferred through the eyelid during expression and to offer a stable resistance, to increase the amount of force that is applied to the glands.

Eyelid warming is limited because the warming melts the lipids, but does not address movement of the keratinized material. Further, eyelid warming induces transient visual degradation due to corneal distortion. Mechanical lid hygiene is also limited because the force needed to remove an obstruction can be significant, resulting in significant pain to the patient. The effectiveness of mechanical lid hygiene is limited by the patient's ability to tolerate the associated pain during the procedure. Other treatments for MGD are limited.

Physical opening of meibomian glands obstruction by meibomian gland expression is an acceptable method to improve meibomian gland secretion and dry eye symptoms. In addition probing of the meibomian gland canal has been used to open the obstructed canal. Both methods, expression and probing, are limited, however, by the pain induced by the procedure, the possible physical insult to the gland and canal structures and their short lived effect estimated at days and weeks. Therefore, methods are needed to improve patient comfort, which will not cause harm to the meibomian glands and canals, that will reduce the dependency on frequent office visits and improve secretion of meibum.

U.S. Pat. No. 9,463,201 entitled, "Compositions and methods for the treatment of meibomian gland dysfunction" describes a method for treating meibomian gland dysfunction involving the topical administration of a therapeutically-effective amount of at least one keratolytic agent in an ophthalmically-acceptable carrier. The patent includes keratolytic agents that are inorganic selenium (Se) compounds such as selenium disulfide ($SeS_2$) or organoselenium compounds such as Ebselen (2-Phenyl-1,2-benzoselenazol-3-one). This agent would treat the underlying cause of MGD, but not a "plus" inflammatory disease as described by the DEWS report on MGD.

The role of inflammation in the etiology of MGD is controversial. The terms posterior blepharitis and MGD are not synonymous. Posterior blepharitis describes inflammatory conditions of the posterior lid margin and has various causes, of which MGD is only one possible cause (Nichols et al 2011). In its earliest stages, MGD is not associated with clinical signs characteristic of posterior blepharitis. As MGD progresses, an MGD-related posterior blepharitis is said to be present. MGD-related posterior blepharitis affects the meibomian glands and meibomian gland orifices. MGD-related posterior blepharitis is characterized by flora changes, esterase and lipase release, lipid changes, and eyelid inflammation. Hyperkeratinization of the meibomian gland epithelium (thickening of the lining of the glands) may lead to obstruction and a decrease in the quantity of meibomian gland secretions and may be responsible for MGD-related posterior blepharitis. Diagnosis of MGD-related posterior blepharitis includes meibomian gland expression with demonstration of an altered quality of expressed secretions, and/or by a loss of gland functionality (decreased or absent expressibility). The TFOS report on Meibomian Gland Disease specifically notes that anterior blepharitis and exacerbated inflammatory ocular surface disease are "plus" diseases to MGD which are managed by topical, ocular steroids (Nichols et al 2011). Since these "plus" conditions can be present in various levels of severity from early to late MGD there is a need for treatments and/or combinations of treatments that can target both the underlying non-inflammatory pathophysiology of MGD and inflammation associated with these comorbid conditions.

MGD-related inflammatory eye disease may comprise a different mechanism than blepharitis-related MGD. MGD-related inflammatory eye disease is characterized by an inflammatory cascade involving activation and migration of T lymphocytes to the inflamed tissue. T lymphocyte infiltration may result in lacrimal gland stimulation and upregulation of cytokines. Exemplary cytokines that may be involved in MGD-related inflammatory eye disease include, but are not limited to, interleukin-1, interleukin-4, interleukin-6, interleukin-8, interferon gamma, macrophage inflammatory protein 1 alpha, and tumor necrosis factor alpha. Kinase pathways including the mitogen activated protein kinase (MAPK) pathway are also activated in the inflammatory cascade. The inflammatory process results in loss of mucin-producing goblet cells and destruction of the ocular surface that can lead to further damage.

Dry eye syndrome, also known as keratoconjunctivitis sicca (KCS), is considered a self-sustaining disease that is progressively disconnected from its initial cause. Dry eye syndrome is associated with inflammation at the ocular surface and periocular tissue. Inflammation is characterized by the activation and migration of T lymphocytes to the inflamed tissue including in the conjunctiva and lacrimal glands. Inflammatory cytokines, chemokines, and matrix metalloproteinase have also been identified as being increased.

Animal models of dry eye disease have been established and reviewed (Barabino, et al, (Invest. Ophthalmol. Vis. Sci. 2004, 45:1641-1646)). Barabino, et al, (Invest. Ophthalmol. Vis. Sci. 2005, 46:2766-2771) described a model wherein exposure of normal mice to a low-humidity environment in a controlled-environment chamber leads to significant alterations in tear secretion, goblet cell density, and acquisition of dry eye-related ocular surface signs. However, no single animal model adequately accounts for the immune, endocrine, neuronal and environmental factors which contribute to dry eye pathogenesis.

Anti-inflammatory agents may be used to treat ocular surface diseases or disorders including dry eye syndrome. Corticosteroids are an effective anti-inflammatory therapy in dry eye disease. For example, in a 4-week, double-masked, randomized study in 64 patients with dry eye and delayed tear clearance, loteprednol etabonate 0.5% ophthalmic suspension (Lotemax [Bausch and Lomb, Rochester, N.Y.]), QID, was found to be more effective than its vehicle in improving some signs and symptoms (Pflugfelder et al, Am J Ophthalmol (2004); 138:444-57). The TFOS 2007 report on dry eye disease went so far as to conclude that, "In the US Federal Regulations, ocular corticosteroids receiving "class labelling" are indicated for the treatment " . . . of steroid responsive inflammatory conditions of the palpebral and bulbar conjunctiva, cornea and anterior segment of the globe such as allergic conjunctivitis, acne rosacea, superficial punctate keratitis, herpes zoster keratitis, iritis, cyclitis, selected infective conjunctivitis, when the inherent hazard of steroid use is accepted to obtain an advisable diminution in edema and inflammation." KCS, in some instances, is included in this list of steroid-responsive inflammatory conditions (Therapy Subcommittee of the International Dry Eye WorkShop, 2007. Management and Therapy of Dry Eye Disease: Report of the Management and Therapy Subcommittee of the International Dry Eye WorkShop (2007). 2007; 5: 163-178)." While the US FDA does not agree with this conclusion, short courses of steroids, especially Lotemax, are commonly used to treat inflammation associated with dry eye disease.

Other anti-inflammatory agents include nonsteroidal anti-inflammatory drugs (NSAIDs). NSAIDs inhibit the activity of cyclooxygenases including cyclooxygenase-1 (COX-1) and cyclooxygenase-2 (COX-2), which are enzymes involved in the synthesis of prostaglandins and thromboxanes from arachidonic acid. Prostaglandin and thromboxane signaling are involved in inflammation and immune modulation. In some cases, NSAIDs are used for treating dry eye disease by treating the inflammation at the ocular surface.

Treatment of dry eye is also accomplished through agents that enhance tear fluid and mucin production. For example, agonists of the P2Y2 receptor have been shown to increase tear fluid and mucin secretion. The mechanism is thought to involve P2Y2 signalling to raise intracellular calcium and open chloride channels in the apical membrane. The P2Y2 receptor belongs to the family of purinergic receptors, which have been classified into P1 receptors and P2 receptors on the basis of their native agonism by purine nucleosides and purine and pyrimidine nucleotides, respectively. P2 receptors are further distinguished physiologically into two types: P2X receptors and P2Y receptors. The P2Y receptors are involved in diver signaling including platelet aggregation, immunity, lipid metabolism, and bone activity. Several studies have also demonstrated the presence of P2X and P2Y receptors in ocular tissues, including the retina, ciliary body, and lens. These studies indicate that $P2Y_2$ receptors appear to be the main subtype of purinergic receptor located at the ocular surface. $P2Y_2$ receptors have also been demonstrated to be localized in ocular tissues in the conjunctival epithelial goblet and serous cells and meibomian gland acinus and ductal epithelial cells of the rhesus macaque.

Lifitegrast

The chemical name for lifitegrast is (S)-2-(2-(benzofuran-6-carbonyl)-5,7-dichloro-1,2,3,4-tetrahydroisoquinoline-6-carboxamido)-3-(3-(methylsulfonyl)phenyl)propanoic acid having a molecular formula of $C_{29}H_{24}Cl_2N_2O_7S$ and a molecular weight is 615.5. Lifitegrast is typically administered as a 5% ophthalmic solution with a pH of 7.0-8.0 and an osmolality range of 200-330 mOsmol/kg. The structural formula of lifitegrast is:

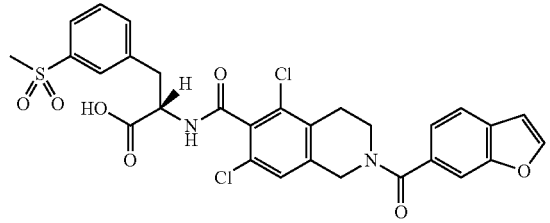

(S)-2-(2-(benzofuran-6-carbonyl)-5,7-dichloro-1,2,3,4-
tetrahydroisoquinoline-
6-carboxamido)-3-(3-(methylsulfonyl)phenyl)propanoic acid Lifitegrast is indicated for the treatment of the signs and symptoms of dry eye disease (DED). Lifitegrast binds to the integrin lymphocyte function-associated antigen-1 (LFA-1), a cell surface protein found on leukocytes and blocks the interaction of LFA-1 with its cognate ligand intercellular adhesion molecule-1 (ICAM-1). ICAM-1 may be overexpressed in corneal and conjunctival tissues in dry eye disease. LFA-1/ICAM-1 interaction can contribute to the formation of an immunological synapse resulting in T-cell activation and migration to target tissues. In vitro studies demonstrated that lifitegrast may inhibit T-cell adhesion to ICAM-1 in a human T-cell line and may inhibit secretion of inflammatory cytokines in human peripheral blood mononuclear cells. The exact mechanism of action of lifitegrast in dry eye disease is not known. More information about lifitegrast can be found in the following U.S. Pat. Nos. 10,124,000, 7,314,938, 7,745,460, 7,790,743, 7,928,122, 8,084,047, 8,168,655, 8,367,701, 8,592,450, 8,927,574, 9,085,553, 9,216,174, 9,353,088, 9,447,077, and 9,890,141.

GW-559090

The chemical name for GW-559090 is (S)-3-(4-((4-carbamoylpiperidine-1-carbonyl)oxy)phenyl)-2-((S)-4-methyl-2-(2-(o-tolyloxy)acetamido)pentanamido)propanoic acid having a molecular formula of $C_{31}H_{40}N_4O_8$ and a molecular weight of 596.7. The structural formula of GW-559090 is:

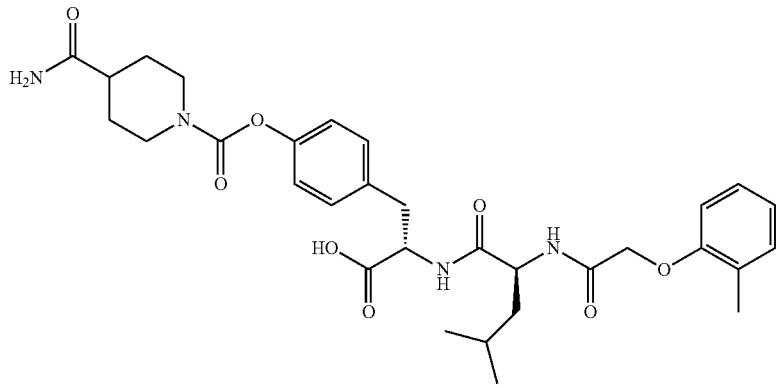

(S)-3-(4-((4-carbamoylpiperidine-1-carbonyl)oxy)phenyl)-2-((S)-4-methyl-2-((S)-4-methyl-2-(2-(o-tolyoxy)acetamido)pentanamido)propanoic acid GW-559090 is a potent integrin a4 antagonist (Ravensberg et al, *Allergy* (2006) 61, 1097-1103) that has demonstrated improvements in objective signs of dry eye in the murine DS model. The potent integrin a4 antagonist was found to act locally at the level of the ocular surface, presumably by preventing the migration of antigen-presenting cells to the draining lymph nodes with a resulting interruption of the immune cycle of dry eye (*Invest. Ophthalmol. Vis. Sci.* (2015) 56(10), 5888-5895).

Meibomian Gland Dysfunction and Dry Eye Disease Pharmacological Agents

Keratolytic Conjugates as Dual-Acting Agents

Described herein are dual-acting agents which address simultaneously the non-inflammatory keratolytic blockage component of meibomian gland dysfunction and the inflammation associated dry eye disease including aqueous deficiency. The keratolytic conjugates described herein are useful as either an acute therapy (e.g., by a trained specialist or physician) or as a chronic therapy (e.g., in the hands of a patient, or alternatively, by a trained specialist or physician). The keratolytic conjugates are tested, in certain embodiments, using the assays and methods described herein (e.g., as described in the examples). The keratolytic conjugates described herein represent a significant advance in the art as the first-order metabolites obtained from metabolism of the agents are operative against both the keratolytic and the inflammatory component of dry eye disease.

One embodiment provides a compound, having the structure of Formula (Ia):

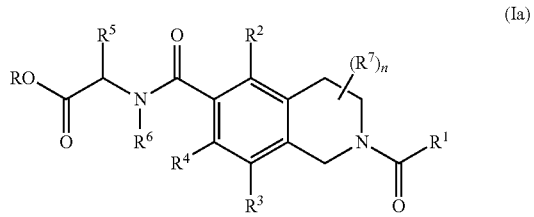

wherein $R^1$ is aryl, cycloalkyl, heterocyclyl, or heteroaryl, wherein the aryl, cycloalkyl, heterocyclyl, or heteroaryl is optionally substituted;

$R^2$, $R^3$, and $R^4$ are each independently H, cyano, halo, ester, alkoxy, alkyl, heteroalkyl, cycloalkyl or heterocyclyl, wherein the alkoxy, alkyl, heteroalkyl, cycloalkyl or heterocyclyl is optionally substituted;

$R^5$ is -L-$R^{5a}$, wherein L is a bond, alkyl, or heteroalkyl, and $R^{5a}$ is absent, a cycloalkyl, a heterocycloalkyl, an aryl, or a heteroaryl, wherein the cycloalkyl, heterocycloalkyl, aryl or heteroaryl is optionally substituted;

$R^6$ is H, alkyl, or heteroalkyl;

each $R^7$ is independently H, cyano, halo, alkoxy, alkyl, heteroalkyl, cycloalkyl or haloalkyl;

n is 0-6;

R is -L'-D, wherein:

D is a keratolytic agent; and

L' is a linker, or a pharmaceutically acceptable salt or solvate thereof.

In some embodiments, L' comprises one or more linker groups, wherein each linker group is selected from the group consisting of a bond, —O—, —S—, alkyl (alkylenyl), heteroalkyl (heteroalkylenyl), disulfide, ester and carbonyl. In some embodiments, the keratolytic agent comprises one or more group (e.g., keratolytic group), each group (e.g., keratolytic group) being independently selected from the group consisting of thiol, disulfide, selenium (e.g., selenide, diselenide), and carboxylic acid.

In certain aspect, the disclosure provides a compound having the structure of Formula (Id):

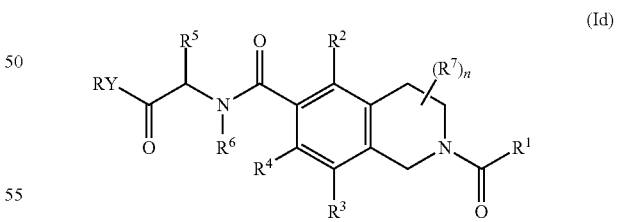

wherein $R^1$ is aryl, cycloalkyl, heterocyclyl, or heteroaryl, wherein the aryl, cycloalkyl, heterocyclyl, or heteroaryl is optionally substituted;

$R^2$, $R^3$, and $R^4$ are each independently H, cyano, halo, ester, alkoxy, alkyl, heteroalkyl, cycloalkyl or, heterocyclyl, wherein the alkoxy, alkyl, heteroalkyl, cycloalkyl or, heterocyclyl is optionally substituted;

$R^5$ is -L-$R^{5a}$, wherein L is a bond, alkyl, or heteroalkyl, and $R^{5a}$ is absent, a cycloalkyl, a heterocycloalkyl, an aryl, or a heteroaryl, wherein the cycloalkyl, heterocycloalkyl, aryl, or heteroaryl is optionally substituted;

$R^6$ is H, alkyl, or heteroalkyl;

each $R^7$ is independently H, cyano, halo, alkoxy, alkyl, heteroalkyl, cycloalkyl, or haloalkyl;

n is 0-6;

Y is O or S; and

R is alkyl or heteroalkyl substituted with at least one oxo, and further optionally substituted, or a pharmaceutically acceptable salt or solvate thereof.

In certain aspect, the disclosure provides a compound having the structure of Formula (Ia):

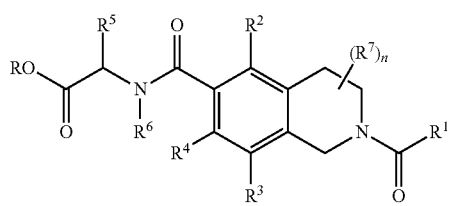

(Ia)

wherein $R^1$ is aryl, cycloalkyl, heterocyclyl, or heteroaryl, wherein the aryl, cycloalkyl, heterocyclyl, or heteroaryl is optionally substituted;

$R^2$, $R^3$, and $R^4$ are each independently H, cyano, halo, ester, alkoxy, alkyl, heteroalkyl, cycloalkyl or, heterocyclyl, wherein the alkoxy, alkyl, heteroalkyl, cycloalkyl or, heterocyclyl is optionally substituted;

$R^5$ is -L-$R^a$, wherein L is a bond, alkyl, or heteroalkyl, and $R^a$ is absent, a cycloalkyl, a heterocycloalkyl, an aryl, or a heteroaryl, wherein the cycloalkyl, heterocycloalkyl, aryl, or heteroaryl is optionally substituted;

$R^6$ is H, alkyl, or heteroalkyl;

each $R^7$ is independently H, cyano, halo, alkoxy, alkyl, heteroalkyl, cycloalkyl, or haloalkyl;

n is 0-6; and

R is alkyl or heteroalkyl substituted with at least one oxo, and further optionally substituted, or a pharmaceutically acceptable salt or solvate thereof.

In some embodiments, the alkyl or heteroalkyl of R is substituted with one or more substituent, each substituent independently selected from the group consisting of alkyl, heteroalkyl, hydroxyl, thiol, thioether, disulfide, seleno, selenol, selenide, diselenide, sulfone, amide, halo, oxo, heterocyclyl, and cycloalkyl, wherein the heterocyclyl, and cycloalkyl is optionally substituted (e.g., with one or more substituent selected from the group consisting of alkyl, heteroalkyl, hydroxyl, thiol, thioether, disulfide, selenol, sulfone, amide, halo and oxo).

In some embodiments, R is

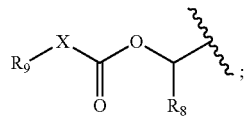

X is —O— or a bond;

$R^1$ is hydrogen, alkyl, heteroalkyl, or haloalkyl;

$R^9$ is alkyl or heteroalkyl, the alkyl or heteroalkyl being optionally substituted, or a pharmaceutically acceptable salt or solvate thereof.

In some embodiments, the alkyl or heteroalkyl of $R^9$ is substituted with one or more substituent, each substituent independently selected from the group consisting of alkyl, heteroalkyl, hydroxyl, thiol, thioether, disulfide, seleno, selenol, selenide, diselenide, sulfone, amide, ester, carboxylic acid, halo, oxo, heterocyclyl, and cycloalkyl, wherein the heterocyclyl, and cycloalkyl is optionally substituted (e.g., with one or more substituent selected from the group consisting of alkyl, heteroalkyl, hydroxyl, thiol, thioether, disulfide, selenol, sulfone, amide, ester halo and oxo).

In some embodiments, $R^6$ is H. In some embodiments, $R^3$ is H. In some embodiments, n is 0. In some embodiments, $R^1$ is optionally substituted aryl, heteroaryl, cycloalkyl, or heterocyclyl. In some embodiments, $R^1$ is heteroaryl. In some embodiments, $R^1$ is benzofuran. In some embodiments, $R^2$ and $R^4$ are each independently H, halo, alkoxy, or alkyl. In some embodiments, $R^2$ and $R^4$ are halo. In some embodiments, $R^2$ and $R^4$ are chloro. In some embodiments, $R^5$ is optionally substituted aryl, heteroaryl, aryl-alkyl, or heteroaryl-alkyl. In some embodiments, $R^5$ is optionally substituted aryl-alkyl. In some embodiments, $R^5$ is substituted aryl-alkyl. In some embodiments, $R^5$ is a sulfonyl substituted aryl-alkyl.

In certain embodiments, the compound has the structure of Formula (Ib):

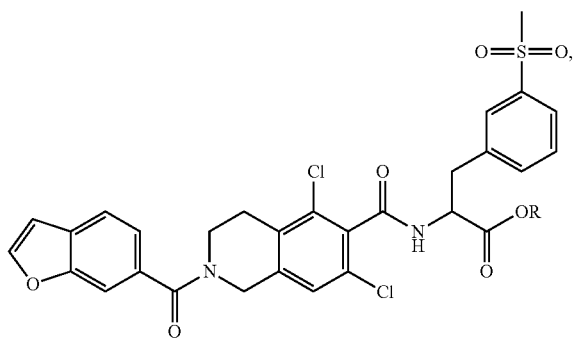

(Ib)

or a pharmaceutically acceptable salt thereof.

In certain embodiments, the compound has the structure of Formula (Ic):

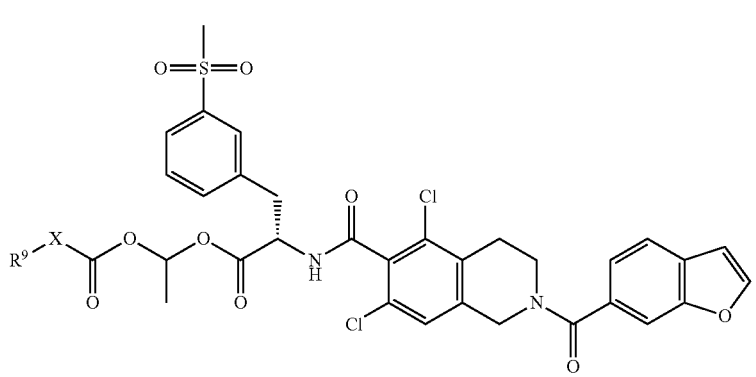

(Ic)

or a pharmaceutically acceptable salt or solvate thereof.

In some embodiments, X is —O— and $R^9$ is $C_{1-6}$ alkyl —$(CR^dR^e)_p$(C=O)($C_1$-$C_6$-alkyl), —$(CR^dR^e)_p$carbocyclyl, —$(CR^dR^e)_p$heterocyclyl, or

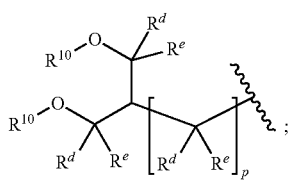

and $R^d$ and $R^e$ are each independently H, halo, alkyl, alkoxy, hydroxyl, thioether, sulfide, thiol, disulfide, seleno, heteroalkyl, carbocyclyl, carbocyclylalkyl, carbocyclylalkoxy, carboxyl, heterocyclyl, heterocyclylalkyl, or heterocyclylalkoxy;

$R^{10}$ is —(C=O)$C_{1-6}$ alkyl;

p is 1 to 6; and wherein $C_{1-6}$ alkyl is optionally substituted with halo, alkyl, heteroalkyl, alkoxy hydroxyl, thiol, disulfide, selenide, diselenide, amide, heterocyclyl or heterocyclylalkyl.

In some embodiments, X is a bond and $R^9$ is $C_{1-6}$ alkyl, heteroalkyl or heterocyclylalkyl wherein the $C_{1-6}$ alkyl may be linear or branched and is optionally substituted with halo, alkyl, heteroalkyl, alkoxy hydroxyl, thiol, disulfide, selenide, diselenide, amide, heterocyclyl or heterocyclylalkyl. In some embodiments, $R^9$ is methyl, ethyl, propyl, isopropyl, butyl, isobutyl, sec-butyl, tert-butyl, —CH$_2$OH, —CH(CH$_3$)OH, —CH$_2$(OCH$_2$CH$_2$)$_4$OH, —CH$_2$CH$_2$(OCH$_2$CH$_2$)$_4$OH,

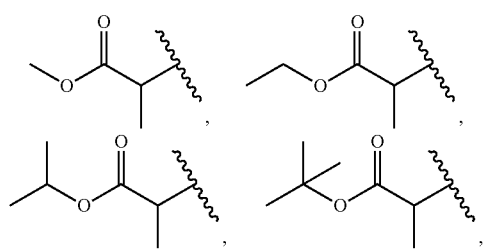

-continued

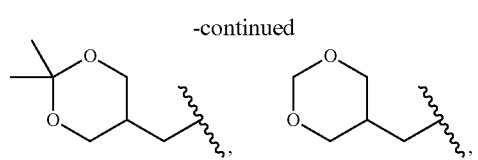

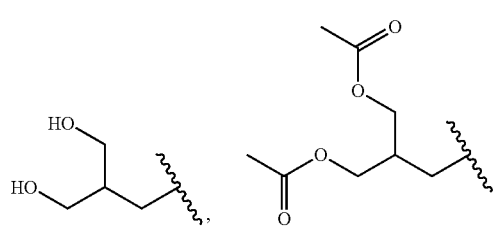

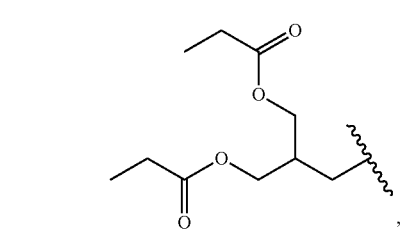

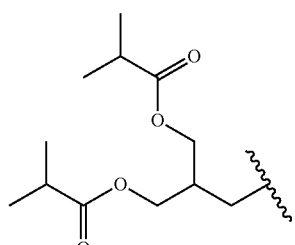

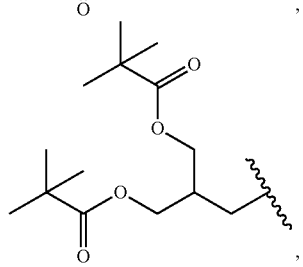

-continued
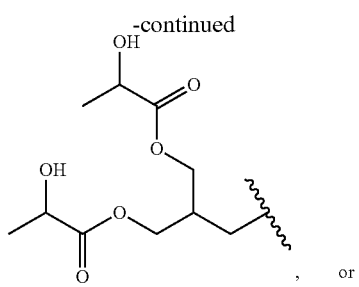, or
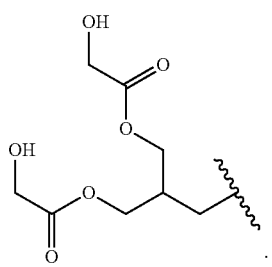.
In some embodiments, $R^9$ is methyl, ethyl, propyl, isopropyl, butyl, isobutyl, sec-butyl, tert-butyl, $CH_2OH$,
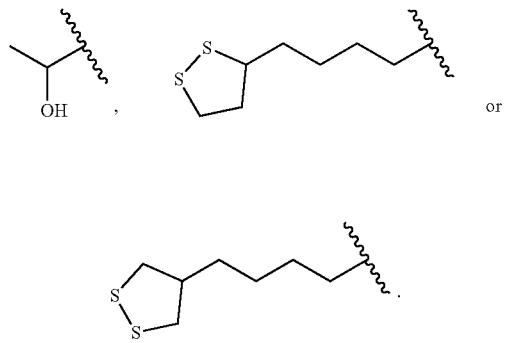.
One embodiment provides a compound, or a pharmaceutically acceptable salt thereof, having the structure of Formula (I):
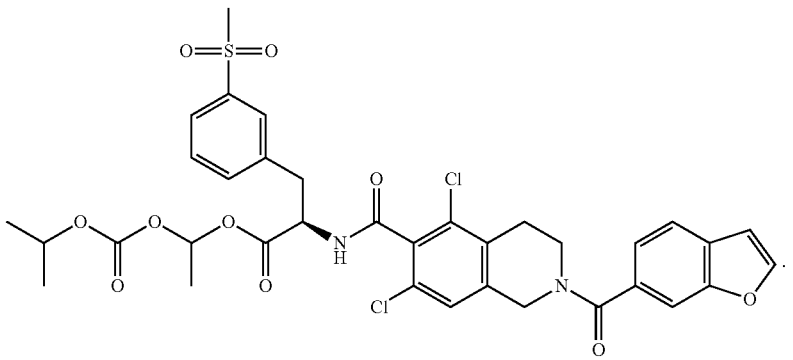
(I)
One embodiment provides a compound, or a pharmaceutically acceptable salt thereof, having the structure of Formula (I'):
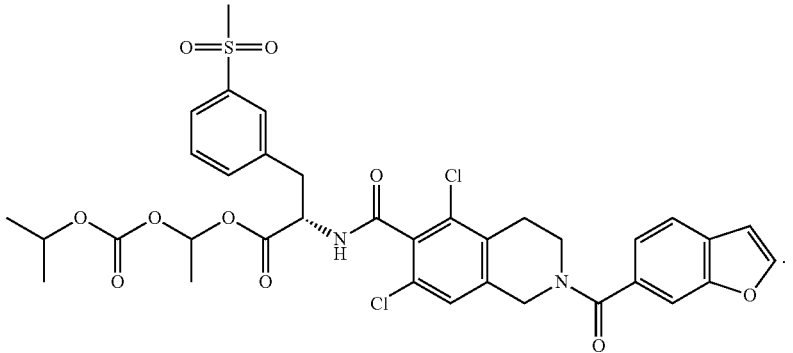
(I')

One embodiment provides a compound, or a pharmaceutically acceptable salt thereof, having the structure of Formula (II):

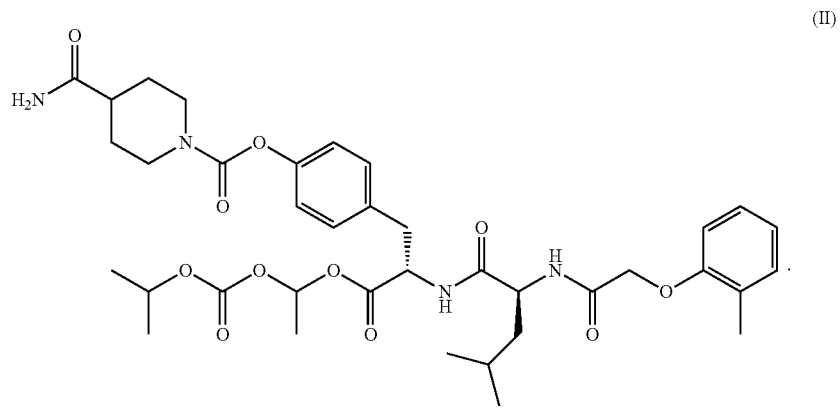 [SMILES: Cc1ccccc1OCC(=O)N[C@@H](CC(C)C)C(=O)N[C@@H](Cc1ccc(OC(=O)N2CCC(C(N)=O)CC2)cc1)C(=O)OC(C)OC(=O)OC(C)C]

(II)

In one embodiment is provided a keratolytic conjugate, or pharmaceutically acceptable salt thereof, having a structure provided in Table 1.

TABLE 1

| Chemistry Example | Structure | Name |
| --- | --- | --- |
| 1 | 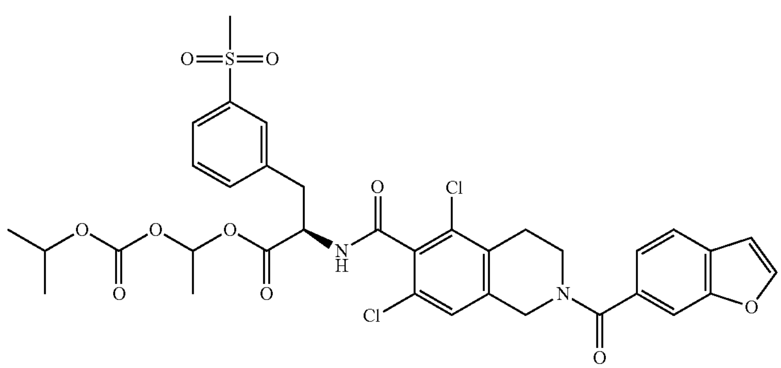 [SMILES: CC(C)OC(=O)OC(C)OC(=O)[C@@H](Cc1cccc(S(C)(=O)=O)c1)NC(=O)c1c(Cl)cc2c(c1Cl)CCN(C(=O)c1ccc3ccoc3c1)C2] | 1-((isopropoxy-carbonyl)oxy)ethyl (2R)-2-(2-(benzofuran-6-carbonyl)-5,7-dichloro-1,2,3,4-tetrahydroisoquinoline-6-carboxamido)-3-(3-(methylsulfonyl)phenyl) propanoate |
| 2 | 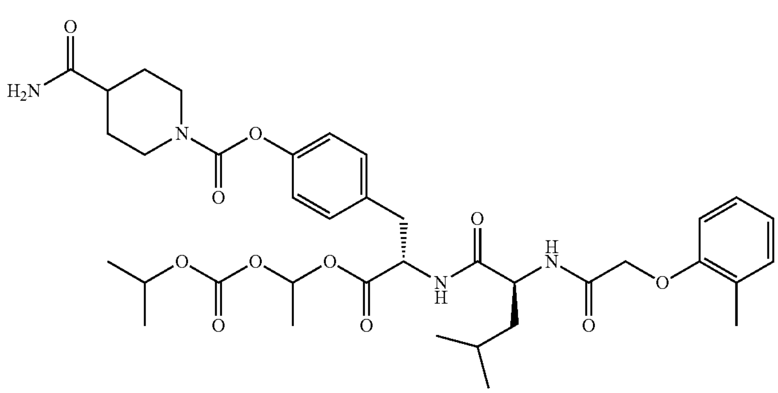 [SMILES: Cc1ccccc1OCC(=O)N[C@@H](CC(C)C)C(=O)N[C@@H](Cc1ccc(OC(=O)N2CCC(C(N)=O)CC2)cc1)C(=O)OC(C)OC(=O)OC(C)C] | 4-((2S)-3-(1-((isopropoxycarbonyl) oxy)ethoxy)-2-((S)-4-methyl-2-(2-(o-tolyloxy)acetamido) pentanamido)-3-oxopropyl)phenyl 4-carbamoylpiperidine-1-carboxylate |

TABLE 1-continued

| Chemistry Example | Structure | Name |
|---|---|---|
| 3 | 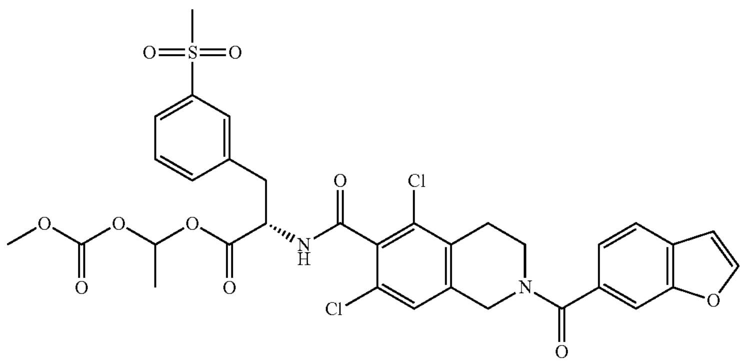 [SMILES: COC(=O)OC(C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-((methoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 4 | 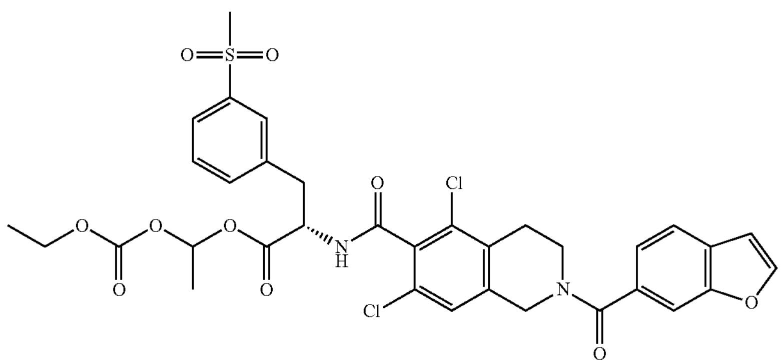 [SMILES: CCOC(=O)OC(C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-((ethoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 5 | 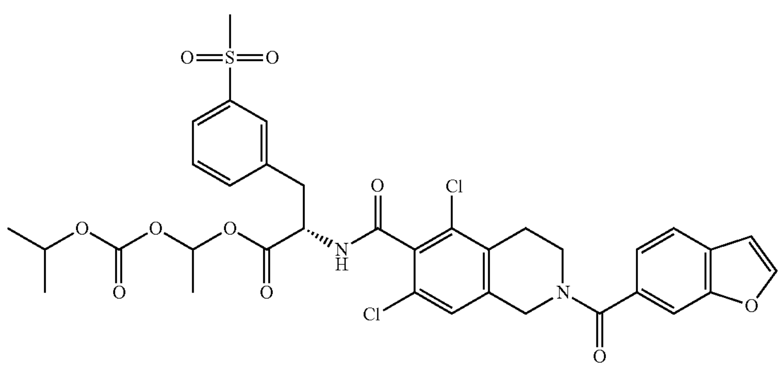 [SMILES: CC(C)OC(=O)OC(C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-((isopropoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 6 | 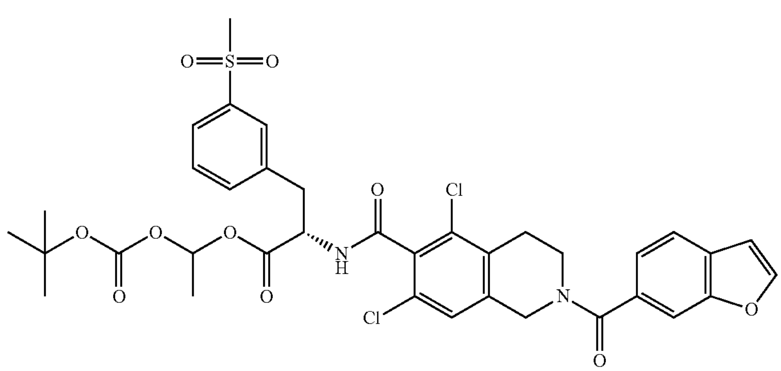 [SMILES: CC(OC(=O)OC(C)(C)C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-((tert-butoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |

TABLE 1-continued

| Chemistry Example | Structure | Name |
|---|---|---|
| 7 | 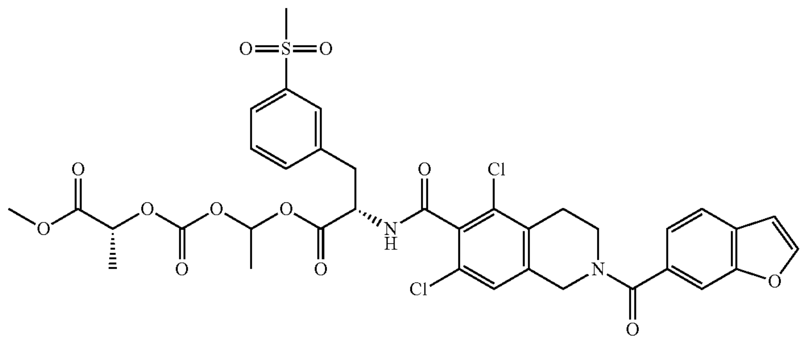 [SMILES: COC(=O)[C@@H](C)OC(=O)OC(C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-(((((R)-1-methoxy-1-oxopropan-2-yl)oxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 8 | 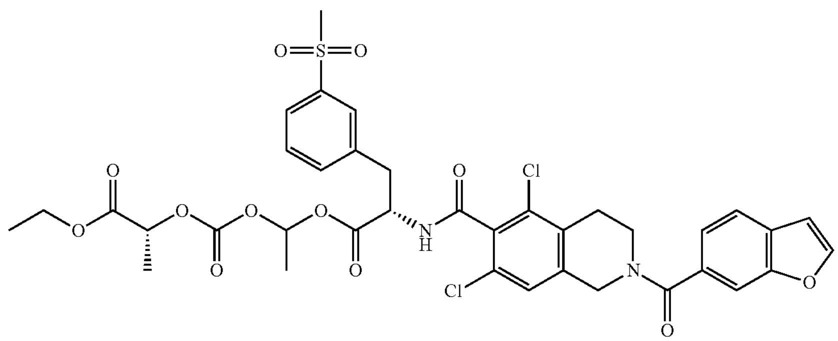 [SMILES: CCOC(=O)[C@@H](C)OC(=O)OC(C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-(((((R)-1-ethoxy-1-oxopropan-2-yl)oxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 9 | 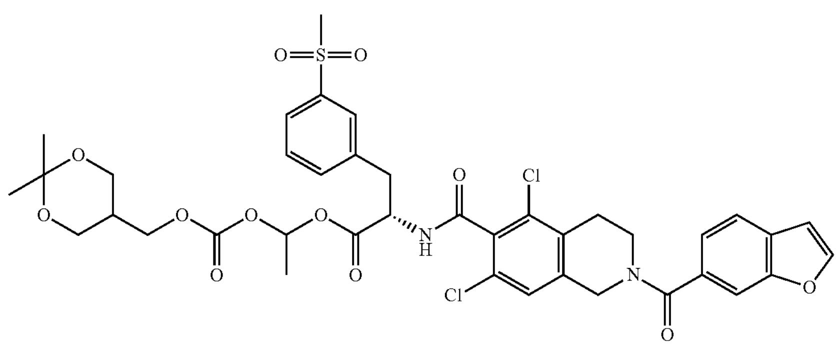 [SMILES: CC(OC(=O)OCC1COC(C)(C)OC1)OC(=O)[C@H](Cc1cccc(S(C)(=O)=O)c1)NC(=O)c1c(Cl)cc2c(c1Cl)CCN(C(=O)c1ccc3ccoc3c1)C2] | 1-((((2,2-dimethyl-1,3-dioxan-5-yl)methoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 10 | 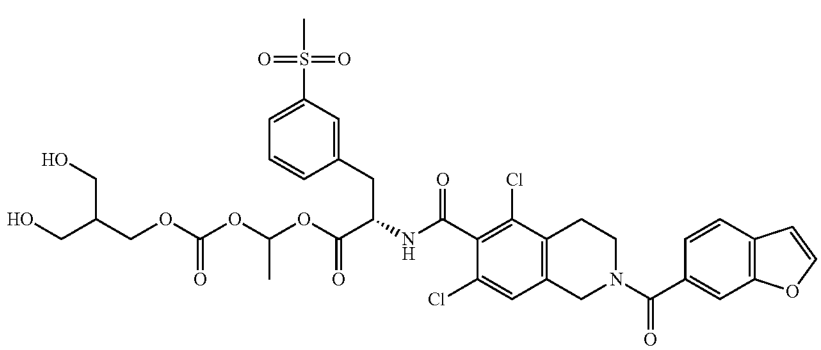 [SMILES: CC(OC(=O)OCC(CO)CO)OC(=O)[C@H](Cc1cccc(S(C)(=O)=O)c1)NC(=O)c1c(Cl)cc2c(c1Cl)CCN(C(=O)c1ccc3ccoc3c1)C2] | 1-(((3-hydroxy-2-(hydroxymethyl)propoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |

TABLE 1-continued

| Chemistry Example | Structure | Name |
| --- | --- | --- |
| 11 | 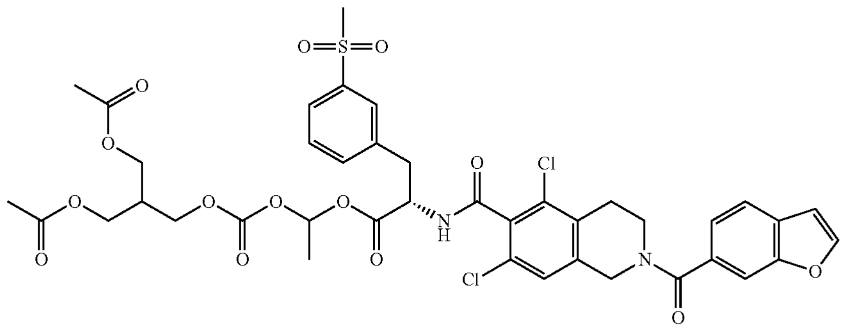 [SMILES: CC(=O)OCC(COC(C)=O)COC(=O)OC(C)OC(=O)[C@H](Cc1cccc(S(C)(=O)=O)c1)NC(=O)c1c(Cl)cc2c(c1Cl)CCN(C(=O)c1ccc3ccoc3c1)C2] | 2-((8S)-10-(2-(benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl diacetate |
| 12 | 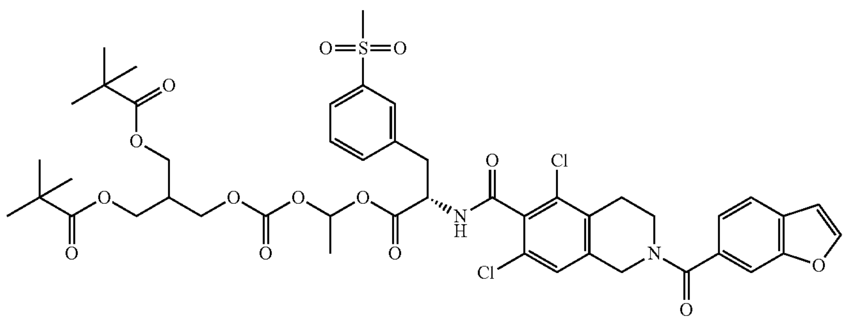 [SMILES: CC(OC(=O)OCC(COC(=O)C(C)(C)C)COC(=O)C(C)(C)C)OC(=O)[C@H](Cc1cccc(S(C)(=O)=O)c1)NC(=O)c1c(Cl)cc2c(c1Cl)CCN(C(=O)c1ccc3ccoc3c1)C2] | 2-((8S)-10-(2-(benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl bis(2,2-dimethylpropanoate) |
| 13 | 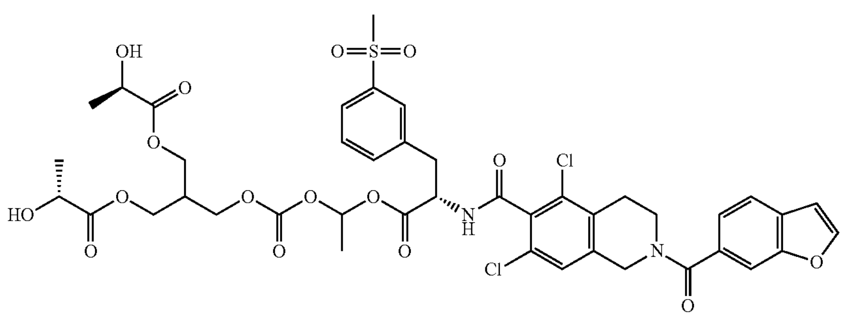 [SMILES: CC(OC(=O)OCC(COC(=O)[C@@H](C)O)COC(=O)[C@@H](C)O)OC(=O)[C@H](Cc1cccc(S(C)(=O)=O)c1)NC(=O)c1c(Cl)cc2c(c1Cl)CCN(C(=O)c1ccc3ccoc3c1)C2] | 2-((8S)-10-(2-(benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl (2R,2'R)-bis(2-hydroxypropanoate) |
| 14 | 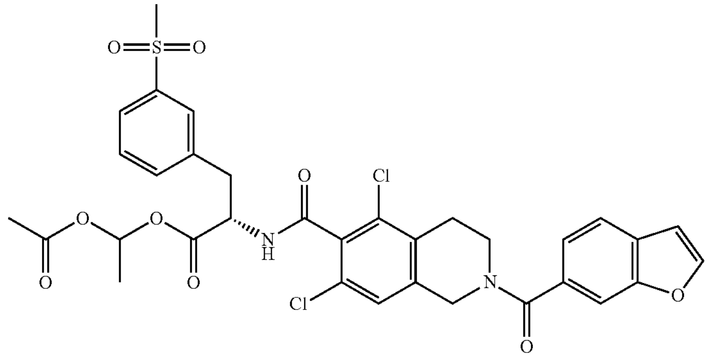 [SMILES: CC(=O)OC(C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-acetoxyethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |

TABLE 1-continued

| Chemistry Example | Structure | Name |
|---|---|---|
| 15 | 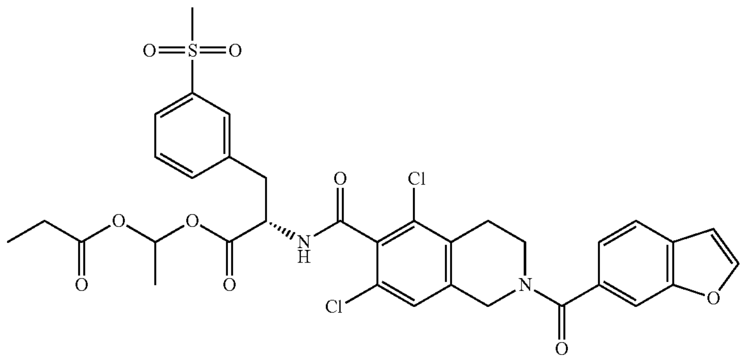 | 1-(propionyloxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 16 | 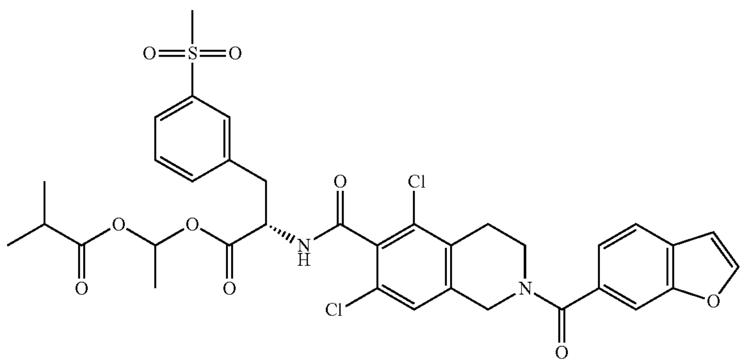 [SMILES: CC(OC(=O)C(C)C)OC(=O)[C@H](Cc1cccc(S(C)(=O)=O)c1)NC(=O)c1c(Cl)cc2c(c1Cl)CCN(C(=O)c1ccc3ccoc3c1)C2] | 1-(isobutyryloxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 17 | 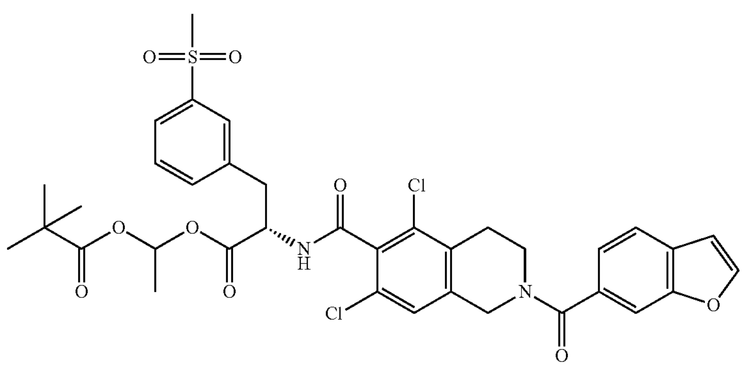 [SMILES: CC(OC(=O)[C@H](Cc1cccc(S(C)(=O)=O)c1)NC(=O)c1c(Cl)cc2c(c1Cl)CCN(C(=O)c1ccc3ccoc3c1)C2)OC(=O)C(C)(C)C] | 1-(((S)-2-(2-(benzofuran-6-carbonyl)-5,7-dichloro-1,2,3,4-tetrahydroisoquinoline-6-carboxamido)-3-(3-(methylsulfonyl)phenyl)propanoyl)oxy)ethyl pivalate |
| 18 | 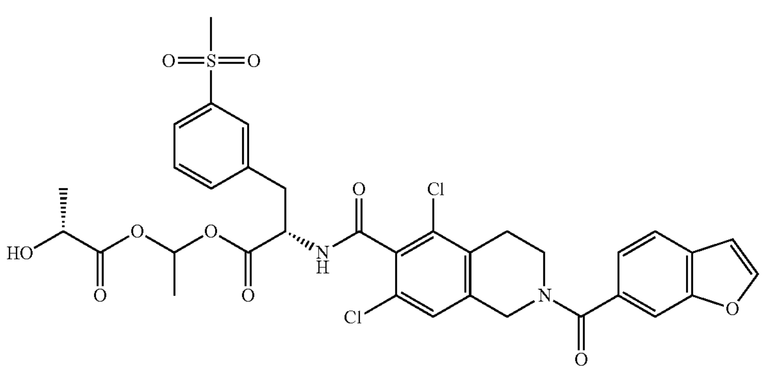 [SMILES: CC(OC(=O)[C@H](Cc1cccc(S(C)(=O)=O)c1)NC(=O)c1c(Cl)cc2c(c1Cl)CCN(C(=O)c1ccc3ccoc3c1)C2)OC(=O)[C@@H](C)O] | 1-(((R)-2-hydroxy-propanoyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |

TABLE 1-continued

| Chemistry Example | Structure | Name |
|---|---|---|
| 19 | 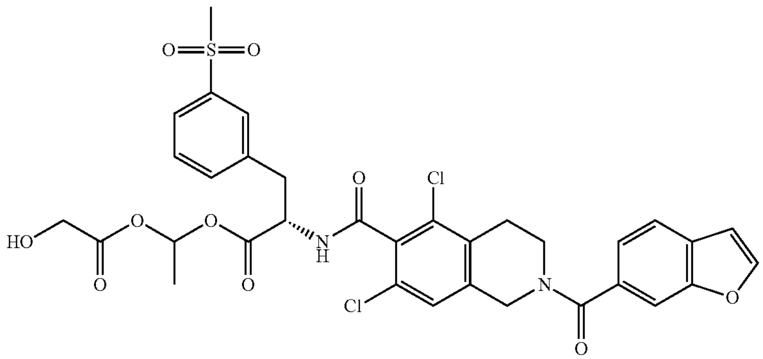 [SMILES: CC(OC(=O)CO)OC(=O)[C@H](Cc1cccc(S(C)(=O)=O)c1)NC(=O)c1c(Cl)cc2c(c1Cl)CCN(C(=O)c1ccc3ccoc3c1)C2] | 1-(2-hydroxyacetoxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate |
| 20 | 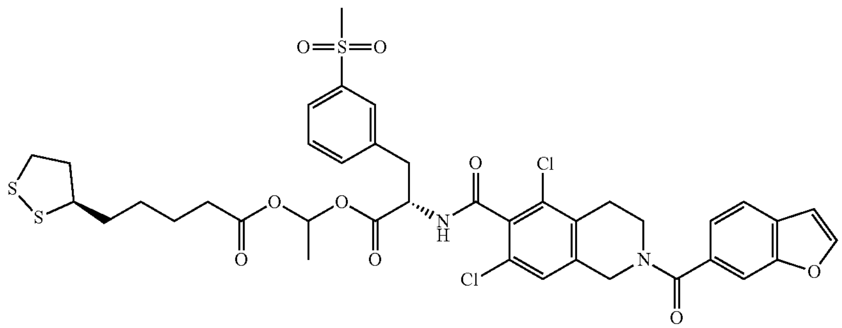 [SMILES: CC(OC(=O)CCCC[C@@H]1CCSS1)OC(=O)[C@H](Cc1cccc(S(C)(=O)=O)c1)NC(=O)c1c(Cl)cc2c(c1Cl)CCN(C(=O)c1ccc3ccoc3c1)C2] | 1-(((S)-2-(2-(benzofuran-6-carbonyl)-5,7-dichloro-1,2,3,4-tetrahydroisoquinoline-6-carboxamido)-3-(3-(methylsulfonyl)phenyl)propanoyl)oxy)ethyl 5-((R)-1,2-dithiolan-3-yl)pentanoate |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the dual-acting meibomian gland dysfunction pharmacological agent described herein is P. H. Stahl & C. G. Wermuth "Handbook of Pharmaceutical Salts", Verlag Helvetica Chimica Acta, Zurich, 2002.

Pharmaceutical Compositions

In some embodiments, the keratolytic conjugate described herein has a structure provided in any one of Formula (Ia), Formula (Ib), Formula (Ic), Formula (Id), Formula (I), or Formula (I'). In some embodiments, the keratolytic conjugate described herein has a structure provided in Formula (II). In some embodiments, the keratolytic conjugate described herein has a structure provided in Formula (III). In certain embodiments, the keratolytic conjugates as described herein is administered as a pure chemical. In other embodiments, the keratolytic conjugate described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Provided herein is a pharmaceutical composition comprising at least one keratolytic conjugate, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising any compound provided herein, such as a compound of any one of Formula (Ia), Formula (Ib), Formula (Ic), Formula (Id), Formula (I), or Formula (I'), or a pharmaceutically acceptable salt thereof, and at least one pharmaceutically acceptable excipient. One embodiment provides a pharmaceutical composition comprising any compound provided herein, such as a compound of any one of Formula (II), or a pharmaceutically acceptable salt thereof, and at least one pharmaceutically acceptable excipient. Another embodiment provides the pharmaceutical composition, wherein the pharmaceutical composition is suitable for ophthalmic administration. Another embodiment provides the pharmaceutical composition, wherein the pharmaceutical composition is suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

One embodiment provides a pharmaceutical composition comprising a compound of Formula (II), or a pharmaceutically acceptable salt thereof, and at least one pharmaceutically acceptable excipient. Another embodiment provides the pharmaceutical composition, wherein the pharmaceutical composition is suitable for ophthalmic administration. Another embodiment provides the pharmaceutical composition, wherein the pharmaceutical composition is suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

In certain embodiments, any compound provided herein, such as the keratolytic conjugate as described by any one of Formula (Ia), Formula (Ib), Formula (Ic), Formula (Id), Formula (I), Formula (I'), Formula (II), or Formula (III) (or pharmaceutically acceptable salt thereof) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

In some embodiments, the keratolytic conjugate as described by any one of Formula (Ia), Formula (Ib), Formula (Ic), Formula (Id), Formula (I), Formula (I'), Formula (II), or Formula (III) is formulated as a solution or suspension for topical administration to the eye.

In some embodiments, the keratolytic conjugate as described by any one of Formula (Ia), Formula (Ib), Formula (Ic), Formula (Id), Formula (I), Formula (I'), Formula (II), or Formula (III) is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising at least one keratolytic conjugate as described herein differ, depending upon the patient's (e.g., human) condition, that is, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. The optimal dose depends upon the body mass, weight, or blood volume of the patient.

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable)

carrier). Exemplary excipients are described, for example, in Remington: The Science and Practice of Pharmacy (Gennaro, 21$^{st}$ Ed. Mack Pub. Co., Easton, Pa. (2005)).

Methods of Treatment Utilizing Keratolytic Conjugates

One embodiment provides a method of treating an ophthalmic disease or disorder in a patient in need of thereof, comprising administering to the patient any compound provided herein, or a pharmaceutically acceptable salt thereof, or a (e.g., pharmaceutical) composition comprising any compound provided herein, or a pharmaceutically acceptable salt thereof, such as a compound of any one of Formula (Ia), Formula (Ib), Formula (Ic), Formula (Id), Formula (I), Formula (I'), Formula (II), or Formula (III). Another embodiment provides the method wherein the pharmaceutical composition is in the form of a solution or suspension suitable for topical ophthalmic administration. In some embodiments, topical ophthalmic administration is administration in and/or around the eye, such as to the eyelid margin. In some embodiments, topical ophthalmic administration is administration to the ocular surface and the inner surface to the eyelid.

Another embodiment provides the method wherein the ophthalmic disease or disorder is selected from dry eye, lid wiper epitheliopathy (LWE), contact lens discomfort (CLD), dry eye syndrome, evaporative dry eye syndrome, aqueous deficiency dry eye syndrome, blepharitis, keratitis, meibomian gland dysfunction, conjunctivitis, lacrimal gland disorder, contact lens related conditions and inflammation of the anterior surface of the eye, infection of the anterior surface of the eye, and autoimmune disorder of the anterior surface of the eye.

Described herein are methods for treating ocular surface disorders in a patient in need comprising topical administration of a keratolytic conjugate to the patient. There are two potential categories of administration. One occurs with the assistance of a health-care provider: this category includes both acute and maintenance uses of the keratolytic conjugate. An acute use, in one embodiment, requires a stronger keratolytic conjugate (either in terms of concentration of the agent or the inherent activity of the agent). A maintenance use, in one embodiment, allows for the use of lower concentrations of the agent, or agents with lower inherent activity. A maintenance use, in one embodiment, involves a patient at a routine visit to the health care provider. Both acute uses and maintenance uses optionally involve use of an eye-protecting device or apparatus. In one embodiment, the acute use is performed by the health care provider, and the maintenance use is performed by the patient or non-health care provider. The second potential category of administration does not occur with the active assistance of a health care provider, but rather involves the patient applying the keratolytic conjugate to his/her own eyelid margin. In one embodiment, such administration occurs over an extended period of time; one way of describing this patient-administered multi-administration mode is as a chronic use. In general, different or second formulations of the keratolytic conjugate are recommended for chronic or patient-administered uses. In one embodiment the different or second formulation utilizes a lower concentration of the keratolytic conjugate. In another embodiment, the second or different formulation utilizes a keratolytic conjugate that has a lower activity than the first formulation.

It should be understood that the present methods also include the physical removal of the obstruction in the meibomian gland, followed by chronic and/or maintenance administration of the keratolytic conjugate described herein.

One embodiment provides a method for treating meibomian gland dysfunction in a patient in need thereof, comprising topically administering to the patient a composition comprising a therapeutically-effective amount of at least one keratolytic conjugate in an ophthalmically-acceptable carrier. In some embodiments, the topical administration of the composition comprising a therapeutically-effective amount of at least one keratolytic conjugate in an ophthalmically-acceptable carrier results in enhanced meibum production.

In some embodiments, the topical administration of the composition comprising a therapeutically-effective amount of at least one keratolytic conjugate in an ophthalmically-acceptable carrier occurs until the keratinized obstruction is relieved. In some embodiments, the topical administration of the composition comprising a therapeutically-effective amount of at least one keratolytic conjugate in an ophthalmically-acceptable carrier occurs periodically after relieving of the keratinized obstruction. In some embodiments, the topical administration of the composition comprising a therapeutically-effective amount of at least one keratolytic conjugate in an ophthalmically-acceptable carrier is a single administration. In some embodiments, the topical administration of the composition comprising a therapeutically-effective amount of at least one keratolytic conjugate in an ophthalmically-acceptable carrier is a periodic administration. In some embodiments, the topical administration of the composition comprising a therapeutically-effective amount of at least one keratolytic conjugate in an ophthalmically-acceptable carrier occurs once a day. In some embodiments, the topical administration of the composition comprising a therapeutically-effective amount of at least one keratolytic conjugate in an ophthalmically-acceptable carrier occurs twice a day. In some embodiments, the topical administration of the composition comprising a therapeutically-effective amount of at least one keratolytic conjugate in an ophthalmically-acceptable carrier occurs more than twice a day.

In some embodiments, the composition for topical administration, comprising a therapeutically-effective amount of at least one keratolytic conjugate in an ophthalmically-acceptable carrier is a solution. In some embodiments, the composition for topical administration, comprising a therapeutically-effective amount of at least one keratolytic conjugate in an ophthalmically-acceptable carrier is a solution suitable for topical administration as eye drops. In some embodiments, the composition for topical administration, comprising a therapeutically-effective amount of at least one keratolytic conjugate in an ophthalmically-acceptable carrier is a gel, ocular insert, spray, or other topical ocular delivery method. In some embodiments, the composition for topical administration, comprising a therapeutically-effective amount of at least one keratolytic conjugate in an ophthalmically-acceptable carrier is a semi-solid. In some embodiments, the composition for topical administration, comprising a therapeutically-effective amount of at least one keratolytic conjugate in an ophthalmically-acceptable carrier is homogenous. In some embodiments, the composition for topical administration, comprising a therapeutically-effective amount of at least one keratolytic conjugate in an ophthalmically-acceptable carrier is a dispersion. In some embodiments, the composition for topical administration, comprising a therapeutically-effective amount of at least one keratolytic conjugate in an ophthalmically-acceptable carrier is hydrophilic. In some embodiments, the composition for topical administration, comprising a therapeutically-effective amount of at least one keratolytic conjugate in an ophthalmically-acceptable carrier has an oleaginous base. In some embodiments, the composition for topical administration, comprising a therapeutically-effective amount of at least one keratolytic conjugate in an ophthalmically-acceptable carrier has at least one ophthalmically-acceptable excipient.

One embodiment provides a method for treating MGD in a patient in need thereof comprising topical administration of a composition comprising a keratolytic conjugate. In some embodiments, the topical administration of the composition comprising a keratolytic conjugate occurs once a week. In some embodiments, the topical administration of the composition comprising a keratolytic conjugate occurs twice a week. In some embodiments, the topical administration of the composition comprising a keratolytic conjugate occurs every other day. In some embodiments, the topical administration of the composition comprising a keratolytic conjugate occurs every day. In some embodiments, the topical administration of the composition comprising a keratolytic conjugate occurs several times a day.

In some embodiment, the method comprises treatment in an acute treatment scenario. In another embodiment, the method comprises treatment of a patient naïve to treatment. In another embodiment, the method comprises treatment in a chronic treatment scenario. In another embodiment, the method comprises treatment in a maintenance therapy scenario. In an acute treatment scenario, the administered dosage of keratolytic conjugate maybe higher than the administered dosage of keratolytic conjugate employed in a chronic treatment scenario or a maintenance therapy scenario. In an acute treatment scenario, the keratolytic conjugate maybe different from the keratolytic conjugate employed in a chronic treatment scenario. In some embodiments, the course of therapy begins in the initial phase of therapy as an acute treatment scenario and later transitions into a chronic treatment scenario or a maintenance therapy scenario. In some embodiments, the meibomian gland opening pharmacological agent administered in the acute treatment scenario is a keratolytic agent and/or keratoplastic agent, and the pharmacological agent administered in the chronic treatment scenario or a maintenance therapy scenario is a keratolytic conjugate.

In certain clinical presentations, patients may require an initial treatment administered by a physician or healthcare professional, to initially open the blockage of the meibomiam gland, such as by placing a more highly concentrated formulation of one of the keratolytic conjugates described herein. In the event the higher concentration formulations are required, the application thereof may require ocular shielding or other activity to minimize the impact of irritation or disruption of the ocular surface or surrounding tissues. Following such a procedure, a patient may be given a different formulation of keratolytic conjugate to take home to apply periodically to the lid margin to maintain the patency of the meibomiam gland. Such application may occur twice daily, once a day, weekly or monthly, depending on the formulation activity and the desired product profile of the therapy.

One aspect of the methods of treatment described herein is the location of the topical administration of the composition. In one embodiment, the composition comprising a keratolytic conjugate is administered such that no irritation to eye occurs. In one embodiment, the composition comprising a keratolytic conjugate is administered to the eye lid margin.

One additional embodiment of the methods of treatment described herein is the use of a protective element provided to the eye to avoid irritation to the eye. Although the formulations described herein are generally non-irritating, in some embodiments (e.g., high concentration of agent or when used on a sensitive eye) a protective element provides an additional layer of safety and comfort for the patient. In one embodiment, the composition comprising a keratolytic conjugate is administered while an eye shield is placed on the eye to reduce contact of the pharmacological agent with the cornea and/or conjunctiva such that reduced irritation to eye occurs. In some embodiments, the eye shield is a contact lens or an eye covering. In some embodiments, the eye covering comprises a self-adhesive. In one embodiment, the composition comprising a keratolytic conjugate is administered while the lid is pulled away from the globe to reduce contact of the pharmacological agent with the cornea and/or conjunctiva such that reduced irritation to eye occurs.

EXAMPLES

I. Chemical Synthesis

Solvents, reagents and starting materials were purchased from commercial vendors and used as received unless otherwise described. All reactions were performed at room temperature unless otherwise stated. Starting materials were purchased from commercial sources or synthesised according to the methods described herein or using literature procedures.

Abbreviations

The following abbreviations are used in the Examples and other parts of the description:
AcOH: acetic acid
$CD_2Cl_2$: deuterated dichloromethane
$CDCl_3$: deuterated chloroform
COMU: (1-cyano-2-ethoxy-2-oxoethylideneaminooxy)dimethylamino-morpholino-carbenium hexafluorophosphate
DCC: dicyclohexyl carbodiimide
DCM: dichloromethane
DIPEA: N,N-diisopropylethylamine
DMF: N,N-Dimethylformamide
DMSO-D6: Dimethyl sulfoxide-$d_6$
EtOAc: Ethyl acetate
EtOH: ethanol
HCl: hydrochloric acid
$H_2O$: Water
HPLC: High performance liquid chromatography
$KHSO_4$: potassium bisulfate
MeCN: Acetonitrile
MeOH: Methanol
$MgSO_4$: Magnesium sulfate
mins: Minutes
$N_2$: nitrogen
$NaHCO_3$: sodium bicarbonate
$NH_4Cl$: ammonium chloride
Rt: retention time
r.t.: room temperature
sat.: saturated
TFA: trifluoroacetic acid
THF: tetrahydrofuran Analytical Methods Method A: Phenomenex Gemini C18 5 μm, 150×4.6 mm; A=water+0.1% formic acid; B=MeOH; 40° C.; % B: 0.0 min 5%, 0.5 min 5%, 7.5 min 95%, 10.0 min 95%, 10.1 min 5%, 13.0 min 5%; 1.5 mL/min.

Method B: Phenomenex Luna C18 (2) 3 μm, 50×4.6 mm; A=water+0.1% formic acid; B=MeOH+0.1% formic acid;

Method C: Phenomenex Luna C18 (2) 5 μm, 150×4.6 mm; A=water+0.1% formic acid; B=MeCN; 40° C.; % B: 0.0 min 5%, 0.5 min 5%, 7.5 min 95%, 10.0 min 95%, 10.1 min 5%, 13.0 min 5%; 1.50 mL/min.

Method D: Phenomenex Luna C18 (2) 3 μm, 50×4.6 mm; A=water pH 9 (ammonium bicarbonate 10 mM); B=MeOH; 45° C.; % B: 0.0 min 5%, 1.0 min 37.5%, 3.0 min 95%, 3.5 min 95%, 3.51 5%, 4.0 min 5%; 2.25 mL/min.

Method E: Waters Sunfire C18 3.5 μm, 50×4.6 mm; A=water+0.1% formic acid; B=MeCN; 40° C.; % B: 0.0 min 5%, 1.0 min 37.5%, 3.0 min 95%, 3.5 min 95%, 3.51 min 5%, 4.0 min 5%; 2.25 mL/min.

Method F: Phenomenex Gemini NX C18 5 μm, 150×4.6 mm; A=water+0.1% formic acid; B=MeOH+0.1% formic acid; 40° C.; % B: 0.0 min 5%, 0.5 min 5%, 7.5 min 95%, 10.0 min 95%, 10.1 min 5%, 13.0 min 5%; 1.5 mL/min.

Chemical Synthesis Example 1

1-((Isopropoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

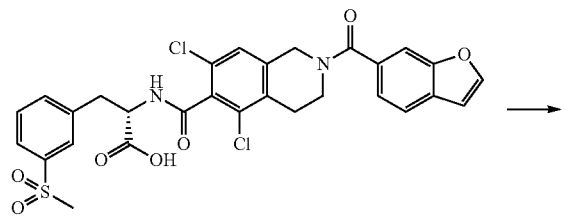

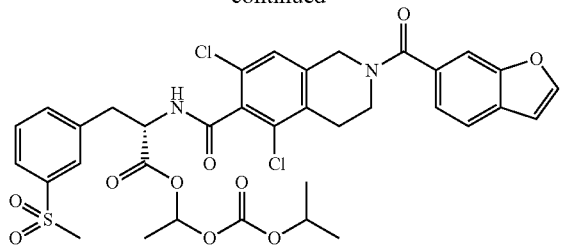

To a stirred solution of Lifitegrast (250 mg, 0.410 mmol) in anhydrous DMF (5 mL) was added 1-chloroethyl isopropyl carbonate (81.2 mg, 0.490 mmol) followed by potassium carbonate (73.0 mg, 0.530 mmol) and the mixture stirred at 55° C. for 2 hours. The mixture was diluted with EtOAc and washed successively with water followed by sat. brine solution. The organic phase was dried (MgSO$_4$) and the solvent evaporated in vacuo. The residue was dissolved in DMSO and the product purified by reversed-phase preparative HPLC. Fractions containing product were combined and concentrated in vacuo to approximately ⅕ of the volume. The mixture was diluted with EtOAc and washed successively with water followed by sat. brine solution. The organic phase was dried (MgSO$_4$), filtered and the solvent evaporated in vacuo. The residue was dissolved in 1:1 MeCN—H$_2$O and the solution frozen. The solvent was evaporated by lyophilisation to reveal the title compound as an off-white solid (72 mg, 24%). LCMS (Method A): Rt=7.87 mins; [M+H]+=745.3. $^1$H-NMR (400 MHz, CD$_2$Cl$_2$) δ 7.78-7.91 (m, 2H), 7.76 (d, J=2.1 Hz, 1H), 7.67 (d, J=7.8 Hz, 1H), 7.57-7.64 (m, 2H), 7.49-7.56 (m, 1H), 7.31 (d, J=7.8 Hz, 1H), 6.83-6.93 (m, 1H), 6.77 (td, J=11.1, 5.5 Hz, 1H), 6.32 (dd, J=20.4, 8.5 Hz, 1H), 5.17-5.28 (m, 1H), 4.51-4.99 (m, 3H), 3.78 (s, 2H), 3.17-3.49 (m, 2H), 2.98-3.07 (m, 3H), 2.87 (s, 2H), 1.49-1.56 (m, 3H), 1.25-1.34 (m, 6H).

Chemical Synthesis Example 2

4-((2S)-3-(1-((isopropoxycarbonyl)oxy)ethoxy)-2-((S)-4-methyl-2-(2-(o-tolyloxy)acetamido)pentanamido)-3-oxopropyl)phenyl 4-carbamoylpiperidine-1-carboxylate

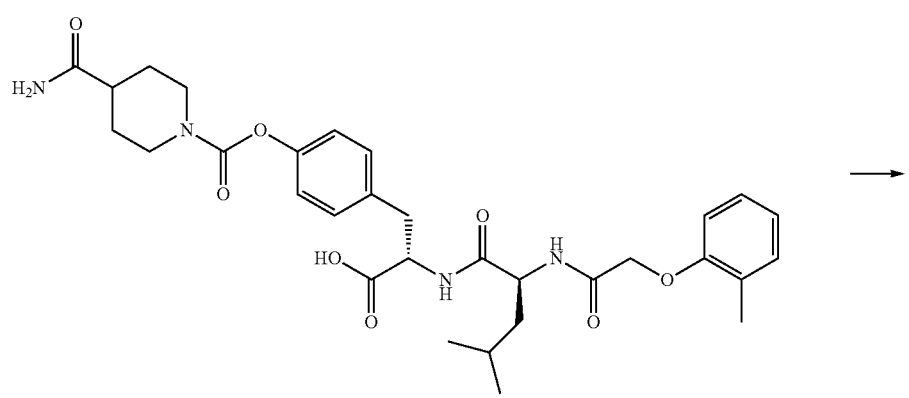

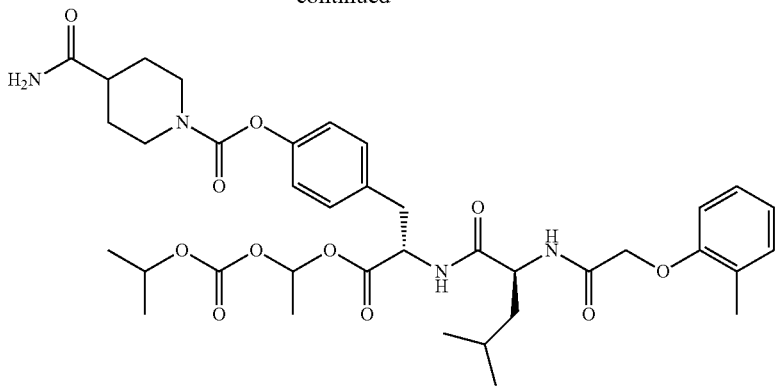

3-[4-(4-carbamoylpiperidine-1-carbonyl)oxyphenyl]-2-[[(2S)-4-methyl-2-[[2-(2-methylphenoxy)acetyl]amino]pentanoyl]amino]propanoic acid (80 mg, 0.134 mmol) was dissolved in anhydrous N,N-dimethylformamide (5.0 mL). 1-Chloroethyl isopropyl carbonate (50 mL, 0.327 mmol) was added and the mixture stirred at 60° C. for 24 hours. N,N-Diisopropylethylamine (80 mL, 0.459 mmol) and 1-chloroethyl isopropyl carbonate (50 mL, 0.327 mmol) were added and the mixture stirred at 60° C. for 2 hours. The solvent was evaporated in vacuo, and the residue partitioned between EtOAc (40 mL) and sat. NaHCO$_{3(aq)}$ (20 mL). The layers were separated and the organic phase washed with sat. brine solution (20 mL), dried (MgSO$_4$), filtered, and the solvent evaporated in vacuo. The crude product was purified by flash chromatography (Biotage SP1; 10 g SNAP cartridge) eluting with EtOAc→20% acetone-EtOAc to yield [4-[3-(1-isopropoxycarbonyloxyethoxy)-2-[[(2S)-4-methyl-2-[[2-(2-methylphenoxy)acetyl]amino]pentanoyl]amino]-3-oxo-propyl]phenyl] 4-carbamoylpiperidine-1-carboxylate (58 mg, 60%) as an off-white solid. LCMS (Method F): Rt=8.36 mins (98.1%) [M+H]+=727.6.

Chemical Synthesis Example 3

1-((tert-Butoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

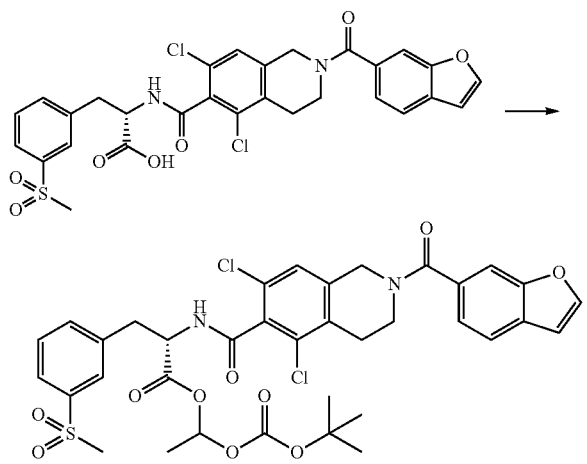

Method A:

To a mixture of Lifitegrast (20 mg, 0.0300 mmol), DIPEA (11 mL, 0.0650 mmol) and DMF (1 mL), under an atmosphere of N$_2$, was added tert-butyl 1-chloroethyl carbonate (7.04 mg, 0.0400 mmol). The reaction mixture was stirred at 60° C. for 48 hours. tert-Butyl 1-chloroethyl carbonate (5.9 mg, 0.033 mmol) and DIPEA (8.9 µL, 0.065 mmol) were added and the reaction mixture stirred at 60° C. for 4 hours. Potassium iodide (5.4 mg, 0.0325 mmol) was added and the reaction mixture stirred at 60° C. for 72 hours. The reaction mixture was diluted with EtOAc (10 mL), and the solution washed successively with H$_2$O (2×5 mL) and sat. brine solution (5 mL). The organic phase was dried (MgSO$_4$), filtered and the solvent evaporated in vacuo. The crude product was then purified by preparative reversed-phase HPLC.

Method B:

A mixture of Lifitegrast (15 mg, 0.0244 mmol), tert-butyl 1-chloroethyl carbonate (8.8 mg, 0.0487 mmol) and cesium carbonate (8.0 mg, 0.0244 mmol) were dissolved in DMF (1 mL) and the mixture stirred at r.t. for 72 hours. The reaction mixture was passed through a syringe filter and the crude product purified by preparative reversed-phase HPLC.

Method C:

A mixture of Lifitegrast (15 mg, 0.0244 mmol), tert-butyl 1-chloroethyl carbonate (8.8 mg, 0.0487 mmol), cesium carbonate (8.0 mg, 0.0244 mmol) and potassium iodide (2.0 mg, 0.0122 mmol) were dissolved in DMF (1 mL) and the mixture stirred at r.t. for 72 hours. The reaction mixture was passed through a syringe filter and the crude product purified by preparative reversed-phase HPLC.

Method D:

The three individual samples from methods A, B & C were combined (as solutions in MeOH) and the solvent evaporated in vacuo. The crude product was purified by preparative reversed-phase HPLC, desired fractions combined, and the solvent evaporated in vacuo. The residue was dissolved in 1:1 MeCN—H$_2$O (2 mL) and the solution frozen. The solvent was evaporated in vacuo (lyophilisation) to yield 1-((tert-butoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (10.2 mg, 16% (combined yield)) as a white solid. LCMS (Method F):

Rt=8.01 min; [M+H]+=759.5 $^1$H-NMR (400 MHz, DMSO-d6) δ 9.15-9.20 (1H, m), 8.12 (1H, d, J=2.3 Hz), 7.87 (1H, br s), 7.66-7.78 (4H, m), 7.53-7.58 (1H, m), 7.10-7.50 (2H, br m), 7.03-7.04 (1H, m), 6.62-6.69 (1H, m), 4.85-4.93 (1H, m), 4.60-4.84 (2H, br s), 3.52-3.94 (2H, m), 3.25-3.30 (1H, m, partially obscured by H₂O peak), 3.13-3.15 (3H, m), 2.98-3.05 (1H, m), 2.76 (2H, br s), 1.39-1.46 (12H, m).

Chemical Synthesis Example 4

1-Chloroethyl ((2,2-dimethyl-1,3-dioxan-5-yl)methyl) carbonate

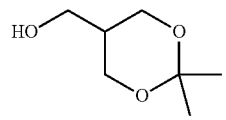

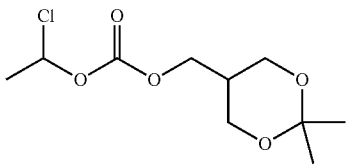

To an ice-cold solution of (2,2-dimethyl-1,3-dioxan-5-yl) methanol (0.40 mL, 2.78 mmol) and pyridine (0.45 mL, 5.56 mmol) in DCM (2 mL) was added dropwise over 1 minute 1-chloroethyl chloroformate (0.30 mL, 2.78 mmol) and the mixture stirred at r.t. for 4 hours. The reaction mixture was partitioned between DCM (10 mL) and H₂O (10 mL) and the organic phase separated (phase separator). The solvent was evaporated in vacuo and the crude product purified by flash chromatography eluting with isohexane→EtOAc to yield 1-chloroethyl ((2,2-dimethyl-1,3-dioxan-5-yl)methyl) carbonate as a yellow/green oil (508 mg, 72%). ¹H-NMR (400 MHz, DMSO-d6) δ 6.47 (1H, q, J=5.8 Hz), 4.21 (2H, d, J=7.3 Hz), 3.88 (2H, dd, J=11.7, 3.9 Hz), 3.60 (2H, J=5.8 Hz, 2H), 1.89-1.95 (1H, m), 1.73 (3H, d, J=6.0 Hz), 1.30 (3H, s), 1.26 (3H, s).

Chemical Synthesis Example 5

1-((((2,2-Dimethyl-1,3-dioxan-5-yl)methoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

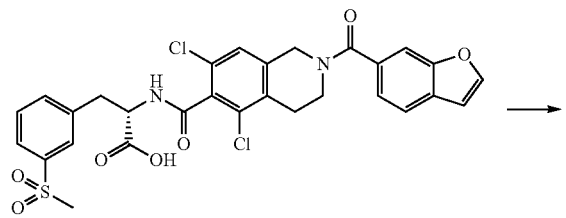

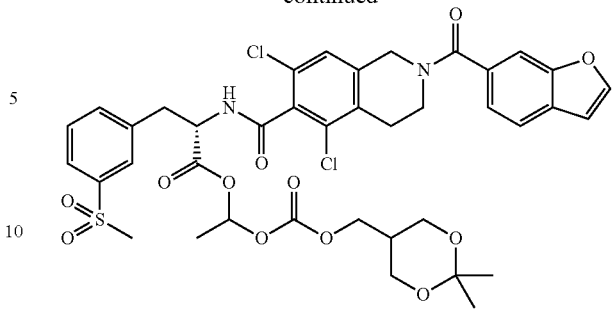

A mixture of Lifitegrast (100 mg, 0.162 mmol), 1-chloroethyl (2,2-dimethyl-1,3-dioxan-5-yl)methyl carbonate (123 mg, 0.487 mmol) and DIPEA (110 mL, 0.650 mmol) were dissolved in DMF (1 mL). The mixture was stirred under N₂ at 60° C. for 18 hours. The reaction mixture was diluted with EtOAc (25 mL) and washed successively with H₂O (10 mL), sat. NaHCO₃(aq) (10 mL) and sat. brine solution (10 mL). The organic phase was dried (MgSO₄), filtered and the solvent evaporated in vacuo. Three purification strategies were then attempted: Purification Method A:

Approximately one quarter of the crude material was dissolved in MeCN (2 mL) and purified by preparative reversed-phase HPLC. Desired fractions were combined and the solvent evaporated in vacuo. The residue was dissolved in a 1:1 MeCN—H₂O (2 mL) and the solution frozen. The solvent was evaporated in vacuo (lyophilisation).

Purification Method B:

Approximately one quarter of the crude material was dissolved in MeCN (2 mL) and purified by preparative reversed-phase HPLC. Desired fractions were combined and extracted with EtOAc (2×50 mL). The combined organics were washed successively with H₂O (50 mL) and sat. brine solution (50 mL), dried (MgSO₄), filtered and the solvent evaporated in vacuo. The residue was dissolved in 1:1 MeCN—H₂O (2 mL) and the solution frozen. The solvent was evaporated in vacuo (lyophilisation) to yield 1-((((2,2-dimethyl-1,3-dioxan-5-yl)methoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl) phenyl)propanoate (10.3 mg, 8%) as a white solid.

Purification Method C:

The remaining crude material plus the material isolated from Purification Method A were combined as solutions in MeCN (2 mL) then purified by preparative reversed-phase HPLC. Desired fractions were combined and extracted with EtOAc (2×50 mL). The combined organics were washed with sat. brine solution (50 mL), dried (MgSO₄), filtered, and the solvent evaporated in vacuo. The residue was dissolved in a 1:1 MeCN—H₂O (2 mL) and the solution frozen. The solvent was evaporated in vacuo (lyophilisation) to yield 1-((((2,2-dimethyl-1,3-dioxan-5-yl)methoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate as an off-white sticky solid (39.1 mg, 29%). LCMS (Method F): Rt=7.78 min; [M+H]+=831.6. ¹H-NMR (400 MHz, DMSO-d6) δ 9.18 (1H, d, J=7.8 Hz), 8.12 (1H, d, J=2.3 Hz), 7.88 (1H, br s), 7.65-7.78 (4H, m), 7.55 (1H, td, J=7.8, 1.8 Hz), 7.10-7.50 (2H, br m), 7.03-7.04 (1H, m), 6.68-6.73 (1H, m), 4.87-4.95 (1H, m), 4.61-4.81 (2H, br s), 4.19 (2H, d, J=7.3 Hz), 3.50-4.00 (6H, br m), 3.27-3.31 (1H, m, partially obscured by H₂O peak), 3.13-3.14 (3H, m), 3.00-3.06 (1H, m), 2.76

(2H, br s), 1.89-1.96 (1H, br m), 1.48 (1.5H, d, J=5.5 Hz), 1.44 (1.5H, d, J=5.5 Hz), 1.31 (3H, s), 1.27 (3H, s).

Chemical Synthesis Example 6

2-((((J-Chloroethoxy)carbonyl)oxy)methyl)propane-1,3-diyl bis(2,2-dimethylpropanoate)

Chemical Synthesis Example 7

2-((8S)-10-(2-(Benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl bis(2,2-dimethylpropanoate)

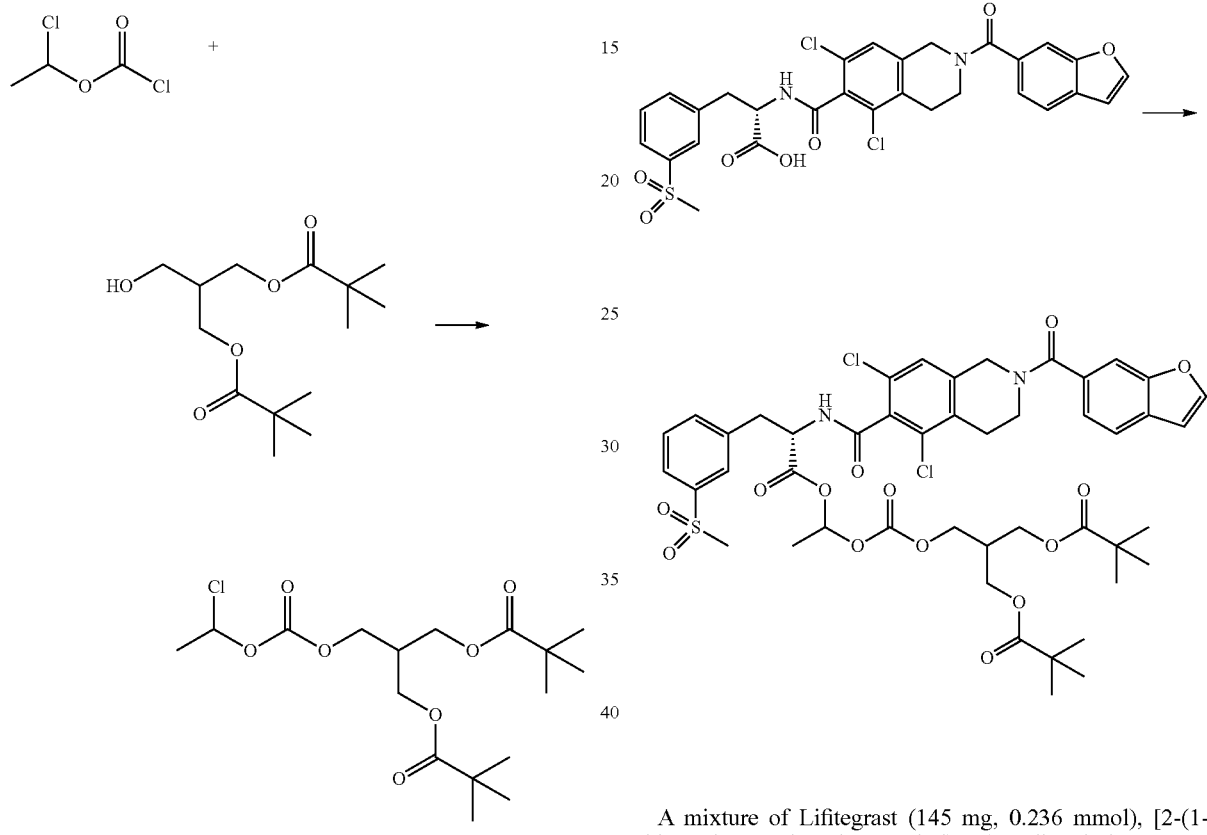

A solution of 1-chloroethyl chloroformate (56 mL, 0.519 mmol) in DCM (2 mL) was placed under an atmosphere of nitrogen and cooled to 0° C. Pyridine (56 mL, 0.693 mmol) was added followed by [2-(2,2-dimethylpropanoyloxymethyl)-3-hydroxy-propyl] 2,2-dimethylpropanoate (200 mL, 0.346 mmol) and the mixture stirred at r.t. for 3 hours. 1-Chloroethyl chloroformate (56 mL, 0.519 mmol) and pyridine (56 mL, 0.693 mmol) were added and the mixture stirred at r.t. for 1 hour. The reaction mixture was partitioned between DCM (10 mL) and $H_2O$ (10 mL) and the layers separated (phase separator). The solvent was evaporated in vacuo and the residue purified by flash chromatography (Biotage SP1; 10 g cartridge) eluting with isohexane→40% EtOAc-isohexane to yield 2-((((1-chloroethoxy)carbonyl)oxy)methyl)propane-1,3-diyl bis(2,2-dimethylpropanoate) (91 mg, 69%) as a colourless oil. $^1$H-NMR (400 MHz, CDCl$_3$) δ 6.40 (1H, q, J=5.8 Hz), 4.24-4.31 (2H, m), 4.06-4.18 (4H, m), 2.43-2.52 (1H, m), 1.82 (3H, d, J=5.5 Hz), 1.19 (18H, s).

A mixture of Lifitegrast (145 mg, 0.236 mmol), [2-(1-chloroethoxycarbonyloxymethyl)-3-(2,2-dimethylpropanoyloxy)propyl] 2,2-dimethylpropanoate (90 mg, 0.236 mmol), DIPEA (82 mL, 0.473 mmol) and DMF (1 mL) were heated in a sealed vial at 60° C. The crude product was purified by preparative reversed-phase HPLC. Desired fractions were combined, and the solvents evaporated in vacuo. The residue was dissolved in 1:1 MeCN—$H_2O$ (3 mL) and the solution frozen. The solvent was evaporated in vacuo (lyophilisation) to yield 2-((8S)-10-(2-(benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl bis(2,2-dimethylpropanoate) (81.1 mg, 36%) as a white solid. LCMS (Method F): Rt=8.54 min; [M+H]+=960.1. $^1$H-NMR (400 MHz, DMSO-d6) δ 9.16 (1H, d, J=7.8 Hz), 8.11 (1H, d, J=2.3 Hz), 7.87 (1H, br s), 7.66-7.77 (4H, m), 7.53-7.57 (1H, m), 7.10-7.50 (2H, br m), 7.03-7.04 (1H, m), 6.68-6.74 (1H, m), 4.86-4.94 (1H, m), 4.72 (2H, br s), 4.15-4.26 (2H, m), 4.02-4.11 (4H, m), 3.50-3.90 (2H, br s), 3.26-3.29 (1H, m, partially obscured by $H_2O$ peak), 3.13-3.14 (3H, m), 2.98-3.07 (1H, m), 2.76 (2H, br s), 2.40-2.47 (1H, m), 1.48 (1.5H, d, J=5.3 Hz), 1.44 (1.5H, d, J=5.3 Hz), 1.10-1.11 (18H, m).

Chemical Synthesis Example 8

1-(((3-Hydroxy-2-(hydroxymethyl)propoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

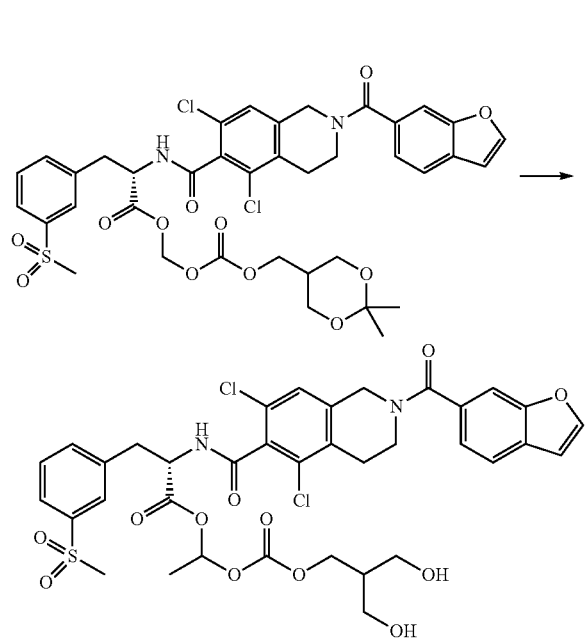

To a solution of 1-((((2,2-dimethyl-1,3-dioxan-5-yl)methoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (36 mg, 0.0433 mmol) in THF (1 mL) was added 2M HCl$_{(aq)}$ (0.50 mL, 1.00 mmol) and the mixture stirred at r.t. for 30 minutes. The reaction mixture was diluted with water (10 mL) and the solution extracted with EtOAc (2×10 mL). The combined organics were washed successively with sat. NaHCO$_{3(aq)}$ (10 mL), water (10 mL) and sat. brine solution (10 mL). The organic phase was dried (MgSO$_4$), filtered and the solvent evaporated in vacuo. The crude product was purified by purified by preparative reversed-phase HPLC. Desired fractions were combined and extracted with EtOAc (2×50 mL). The combined organics were washed with sat. brine solution (50 mL), dried (MgSO$_4$), filtered and the solvent evaporated in vacuo. The residue was dissolved in 1:1 MeCN—H$_2$O (2 mL) and the solution frozen. The solvent was evaporated in vacuo (lyophilisation) to yield 1-(((3-hydroxy-2-(hydroxymethyl)propoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (9.5 mg, 28%) as a white solid. LCMS (Method F): Rt=7.14 min; [M+H]+=791.5. $^1$H-NMR (400 MHz, DMSO-d6) δ 9.16-9.21 (1H, m), 8.11-8.12 (1H, m), 7.88 (1H, br s), 7.66-7.78 (4H, m), 7.53-7.58 (1H, m), 7.10-7.50 (2H, br m), 7.03-7.04 (1H, m), 6.67-6.73 (1H, m), 4.87-4.93 (1H, m), 4.73 (2H, br s), 4.54-4.57 (2H, m), 4.09-4.18 (2H, m), 3.54-3.94 (2H, br m), 3.36-3.47 (4H, m), 3.27-3.31 (1H, m, partially obscured by H$_2$O peak), 3.13-3.15 (3H, m), 2.99-3.06 (1H, m), 2.76 (2H, br s), 1.82-1.89 (1H, m), 1.48 (1.5H, d, J=5.3 Hz), 1.44 (1.5H, d, J=5.3 Hz).

Chemical Synthesis Example 9

2-((((1-Chloroethoxy)carbonyl)oxy)methyl)propane-1,3-diyl Diacetate

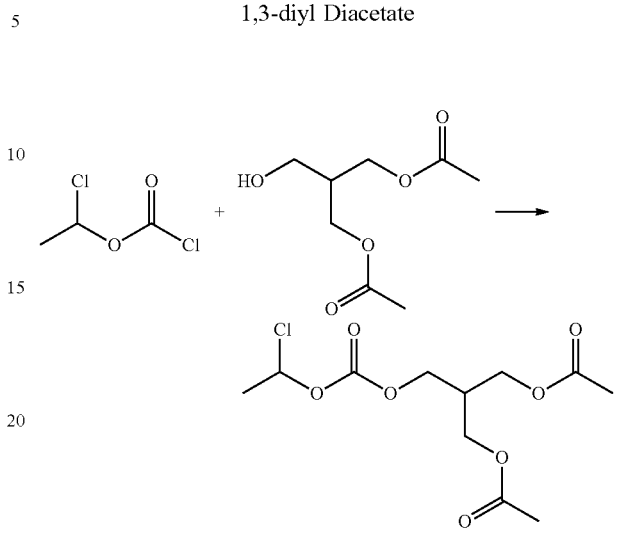

A solution of 1-chloroethyl chloroformate (53 mL, 0.494 mmol) in DCM (2 mL) was placed under an atmosphere of N$_2$ and cooled to 0° C. Pyridine (60 mL, 0.741 mmol) was added followed by [2-(acetoxymethyl)-3-hydroxy-propyl] acetate (200 mL, 0.247 mmol). The mixture was stirred at 0° C. for 6.5 hours. Pyridine (20 ml, 0.250 mmol) and 1-chloroethyl chloroformate (26 mL, 0.250 mmol) were added and the mixture stirred at 0° C. for 90 minutes. 1-Chloroethyl chloroformate (26 ml, 0.250 mmol) was added and the mixture stirred at 0° C. for 90 minutes. The mixture was diluted with DCM (10 mL) and H$_2$O (10 mL). The layers were separated (phase separator) and the organic phase evaporated in vacuo. The crude product was purified by flash chromatography (Biotage SP1; 10 g cartridge) eluting with isohexane→40% EtOac-isohexane yield 2-((((1-chloroethoxy)carbonyl)oxy)methyl)propane-1,3-diyl diacetate (34 mg, 46%) as a colourless oil. $^1$H-NMR (400 MHz, CDCl$_3$) δ 6.39 (1H, q, J=5.8 Hz), 4.27 (2H, d, J=6.0 Hz), 4.09-4.17 (4H, m), 2.38-2.47 (1H, m), 2.05 (6H, s), 1.81 (3H, d, J=5.5 Hz).

Chemical Synthesis Example 10

2-((8S)-10-(2-(Benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl Diacetate

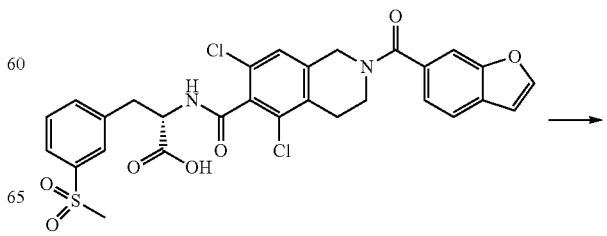

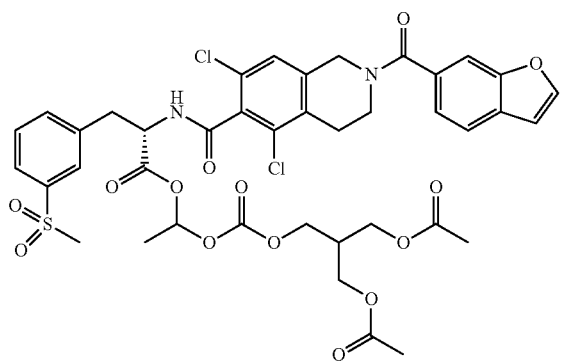

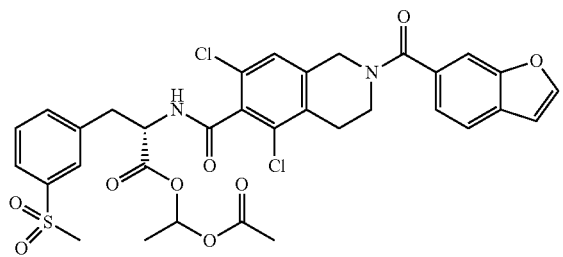

A mixture of [2-(acetoxymethyl)-3-(1-chloroethoxycarbonyloxy)propyl] acetate (34 mg, 0.115 mmol), Lifitegrast (71 mg, 0.115 mmol) and DIPEA (40 mL, 0.229 mmol) were dissolved in DMF (1 mL) and the mixture stirred at 60° C. for 72 hours. The crude product was purified by purified by preparative reversed-phase HPLC. Desired fractions were combined, and the solvent evaporated in vacuo. The residue was dissolved in 1:1 MeCN—H$_2$O (3 mL) and the solution frozen. The solvent was evaporated in vacuo (lyophilisation) to yield 2-((8S)-10-(2-(benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl diacetate (34.4 mg, 34%) as an off-white solid. LCMS (Method F): Rt=7.66 min; [M+H]+=875.5. $^1$H-NMR (400 MHz, DMSO-d6) δ 9.18 (1H, d, J=7.8 Hz), 8.12 (1H, d, J=2.3 Hz), 7.88 (1H, br s), 7.66-7.77 (4H, m), 7.53-7.58 (1H, m), 7.15-7.50 (2H, br m), 7.03-7.04 (1H, m), 6.67-6.73 (1H, m), 4.87-4.94 (1H, m), 4.73 (2H, br s), 4.14-4.23 (2H, m), 4.05 (4H, d, J=6.0 Hz), 3.55-3.90 (2H, br m), 3.27-3.31 (1H, m, partially obscured by H$_2$O peak), 3.13-3.14 (3H, m), 2.99-3.06 (1H, m), 2.76 (2H, br s), 2.35-2.41 (1H, m), 1.98-2.00 (6H, m), 1.48 (1.5H, d, J=5.5 Hz), 1.44 (1.5H, d, J=5.5 Hz).

Chemical Synthesis Example 11

1-Acetoxyethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate Lifitegrast (60 mg, 0.0975 mmol), 1-chloroethyl acetate (18 mg, 0.147 mmol) and DIPEA (34 mL, 0.195 mmol) in DMF (0.90 mL) were heated at 60° C. in a sealed tube for 16 hours. The crude product was purified preparative reversed-phase HPLC to yield 1-acetoxyethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (28 mg, 39%) as an off-white solid. LCMS (Method F): Rt=7.45 min; [M+H]+=701.5. $^1$H-NMR (400 MHz, DMSO-d6) δ 9.13-9.16 (1H, m), 8.09 (1H, d, J=2.3 Hz), 7.84 (1H, s), 7.63-7.74 (4H, m), 7.51-7.55 (1H, m), 7.28 (2H, s), 7.00-7.01 (1H, m), 6.74-6.79 (1H, m), 4.82-4.88 (1H, m), 4.70 (2H, br s), 3.61 (2H, br s), 3.23-3.29 (1H, m, partially obscured by H$_2$O peak), 3.11 (3H, m), 2.94-3.03 (1H, m), 2.73 (2H, br s), 2.01 (3H, s), 1.39 (3H, dd, J=17.9, 5.5 Hz).

Chemical Synthesis Example 12

1-(Isobutyryloxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

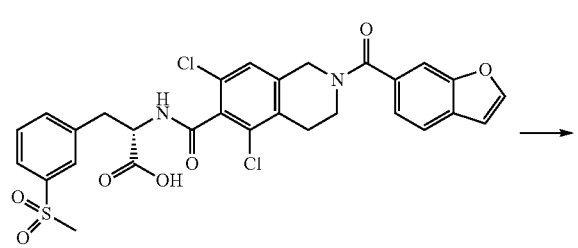

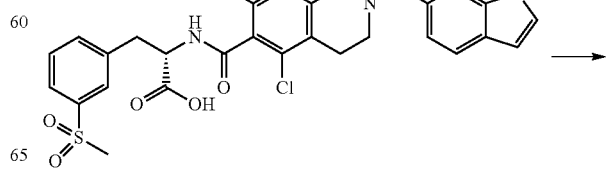

-continued

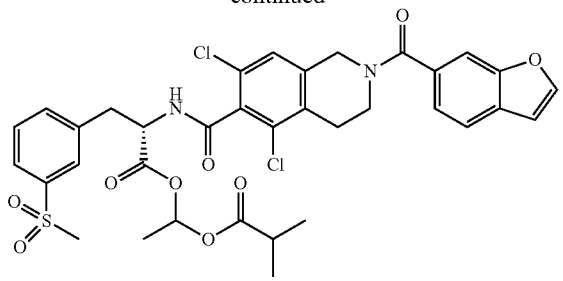

Lifitegrast (60 mg, 0.0975 mmol), 1-chloroethyl 2-methylpropanoate (22 mg, 0.146 mmol) and DIPEA (34 mL, 0.195 mmol) in DMF (0.90 mL) were heated at 60° C. in a sealed tube for 16 hours. The crude product was purified by preparative reversed-phase HPLC to yield 1-(isobutyryloxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (46 mg, 61%) as a brown solid. LCMS (Method F): Rt=7.88 min; [M+H]+=729.5. $^1$H-NMR (400 MHz, DMSO-d$_6$) δ 9.13-9.17 (1H, m), 8.09 (1H, d, J=2.3 Hz), 7.84 (1H, s), 7.63-7.75 (4H, m), 7.50-7.55 (1H, m), 7.27-7.29 (2H, m), 7.01 (1H, m), 6.72-6.79 (1H, m), 4.80-4.89 (1H, m), 4.70 (2H, br s), 3.62 (2H, br s), 3.21-3.26 (1H, m), 3.11 (3H, d, J=3.4 Hz), 2.94-3.03 (1H, m), 2.73 (2H, br s), 2.48-2.53 (1H, m), 1.39 (3H, dd, J=22.9, 5.5 Hz), 1.04 (6H, dd, J=7.1, 2.1 Hz).

Chemical Synthesis Example 13

Methyl (2R)-2-(((1-chloroethoxy)carbonyl)oxy)propanoate

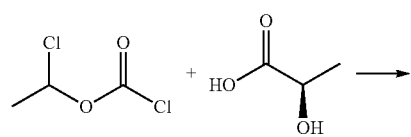

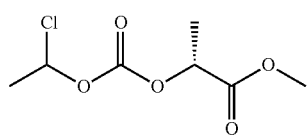

To a solution of 1-chloroethyl chloroformate (339 µL, 3.14 mmol) and pyridine (381 µL, 4.71 mmol) in DCM (10 mL) at 0° C. under N$_2$ was added (R)-methyl 2-hydroxypropanoate (150 µL, 1.57 mmol) in DCM (2 mL) dropwise over 5 mins. The reaction mixture was stirred at r.t. for 16 hours *. The mixture was diluted with DCM (30 mL) and the solution washed with H$_2$O (30 mL). The organic phase was separated (phase separator) and the solvent evaporated in vacuo. The crude product was purified by flash chromatography eluting with isohexane→15% EtOAc-isohexane to yield methyl (2R)-2-(((1-chloroethoxy)carbonyl)oxy)propanoate (275 mg, 75%) as a colourless oil. $^1$H-NMR (400 MHz, CDCl$_3$) δ 6.38-6.43 (1H, m), 5.04-5.10 (1H, m), 3.77 (3H, m), 1.84 (3H, dd, J=6.0, 4.1 Hz), 1.54-1.56 (3H, m).

* Alternatively, the reaction mixture may be stirred at 0° C.→r.t. for up to 40 hours with additional equivalents of chloroformate (up to 0.54) added portion wise at irregular intervals over the course of the reaction to ensure almost complete conversion of the starting material.

Chemical Synthesis Example 14

1-(((((R)-1-Methoxy-1-oxopropan-2-yl)oxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

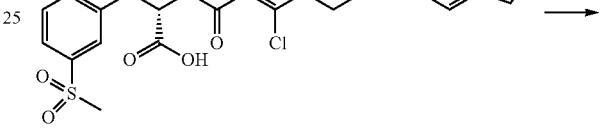

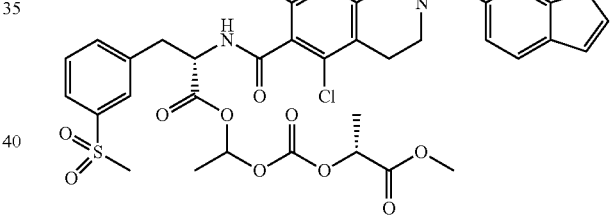

Lifitegrast (60 mg, 0.0975 mmol), methyl (2R)-2-(((1-chloroethoxy)carbonyl)oxy)propanoate (34 mg, 0.146 mmol) and DIPEA (34 mL, 0.195 mmol) in DMF (0.90 mL) were heated in a sealed tube at 60° C. for 16 hours *. The crude product was purified by preparative reversed-phase HPLC ** to yield 1-(((((R)-1-methoxy-1-oxopropan-2-yl)oxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (30 mg, 37%) as an off-white solid. LCMS (Method F): Rt=7.62 min; [M+H]+=789.5. $^1$H-NMR (400 MHz, DMSO-d6) δ 9.14-9.21 (1H, m), 8.08 (1H, d, J=1.8 Hz), 7.85-7.89 (1H, m), 7.63-7.74 (4H, m), 7.50-7.55 (1H, m), 7.28 (2H, br s), 7.00-7.01 (1H, m), 6.64-6.70 (1H, m), 4.97-5.04 (1H, m), 4.82-4.90 (1H, m), 4.64 (2H, br s), 3.64-3.66 (5H, m), 3.21-3.26 (1H, m), 3.11 (3H, m), 2.96-3.07 (1H, m), 2.73 (2H, br s), 1.39-1.48 (6H, m).

* Alternatively, the mixture may be stirred under N$_2$ for up to 18 hours at 60° C.

** Additionally, fractions containing desired product may be combined and the solution frozen. The solvent may be evaporated in vacuo (lyophilisation).

Chemical Synthesis Example 15

The following compound was synthesized via an analogous method to that described for 1-(((((R)-1-Methoxy-1-oxopropan-2-yl)oxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate:

| Structure | Analytical Data |
|---|---|
| 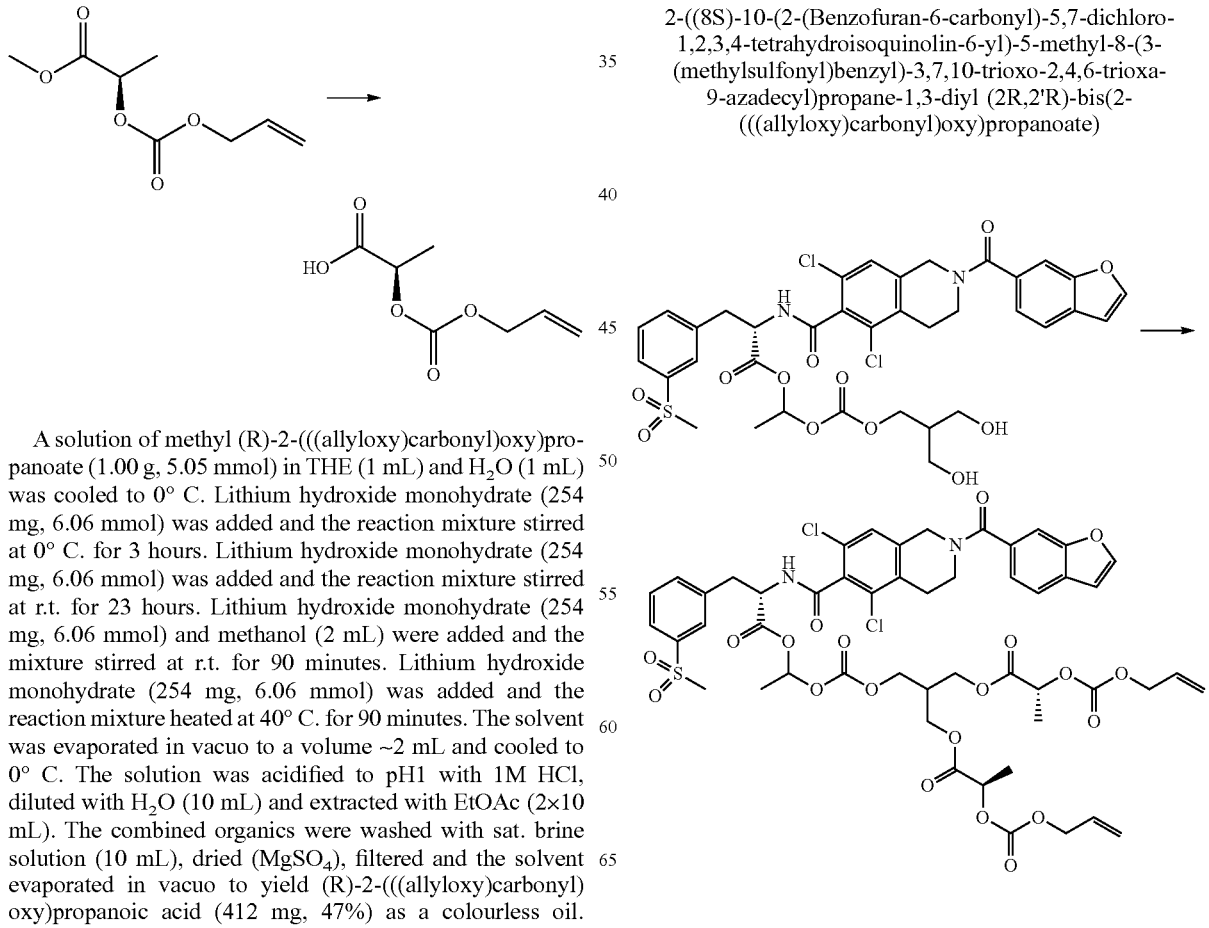 | LCMS (QC Method C): Rt = 7.36 mins; [M + H]+ = 803.2 |

Chemical Synthesis Example 16

(R)-2-(((Allyloxy)carbonyl)oxy)propanoic Acid

A solution of methyl (R)-2-(((allyloxy)carbonyl)oxy)propanoate (1.00 g, 5.05 mmol) in THF (1 mL) and H$_2$O (1 mL) was cooled to 0° C. Lithium hydroxide monohydrate (254 mg, 6.06 mmol) was added and the reaction mixture stirred at 0° C. for 3 hours. Lithium hydroxide monohydrate (254 mg, 6.06 mmol) was added and the reaction mixture stirred at r.t. for 23 hours. Lithium hydroxide monohydrate (254 mg, 6.06 mmol) and methanol (2 mL) were added and the mixture stirred at r.t. for 90 minutes. Lithium hydroxide monohydrate (254 mg, 6.06 mmol) was added and the reaction mixture heated at 40° C. for 90 minutes. The solvent was evaporated in vacuo to a volume ~2 mL and cooled to 0° C. The solution was acidified to pH1 with 1M HCl, diluted with H$_2$O (10 mL) and extracted with EtOAc (2×10 mL). The combined organics were washed with sat. brine solution (10 mL), dried (MgSO$_4$), filtered and the solvent evaporated in vacuo to yield (R)-2-(((allyloxy)carbonyl)oxy)propanoic acid (412 mg, 47%) as a colourless oil.

$^1$H-NMR (400 MHz, CDCl$_3$) δ 5.88-5.97 (1H, m), 5.34-5.40 (1H, m), 5.25-5.30 (1H, m), 5.05 (1H, q, J=7.2 Hz), 4.66 (2H, td, J=3.4, 1.8 Hz), 1.58 (3H, d, J=6.9 Hz).

Chemical Synthesis Example 17

2-((8S)-10-(2-(Benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl (2R,2'R)-bis(2-(((allyloxy)carbonyl)oxy)propanoate)

A solution of (R)-2-(((allyloxy)carbonyl)oxy)propanoic acid (81 mg, 0.467 mmol), COMU (200 mg, 0.467 mmol) and DIPEA (110 mL, 0.654 mmol) in DCM (3 ml) were stirred at r.t. for 10 minutes. A solution of 1-(((3-hydroxy-2-(hydroxymethyl)propoxy)carbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (74 mg, 0.0935 mmol) in DCM (2 mL) was added and the mixture stirred at r.t. for 18 hours. The solvent was evaporated in vacuo and the residue dissolved in EtOAc (30 mL). The solution was washed successively with sat. NH$_4$Cl$_{(aq)}$ (30 mL), H$_2$O (30 mL) and sat. brine solution (30 mL). The organic phase was dried (MgSO$_4$), filtered and the solvent evaporated in vacuo. The crude product was purified by preparative reversed-phase HPLC to yield 2-((8S)-10-(2-(benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl (2R,2'R)-bis(2-(((allyloxy)carbonyl)oxy)propanoate) (10 mg, 10%) as a white solid. LCMS (Method D): Rt=3.34 min; [M+H]+=1103.8.

Chemical Synthesis Example 18

(3R)-1-Hydroxy-7-((((R)-2-hydroxypropanoyl)oxy)methyl)-3-methyl-1,4,10-trioxo-2,5,9,11-tetraoxatridecan-12-yl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

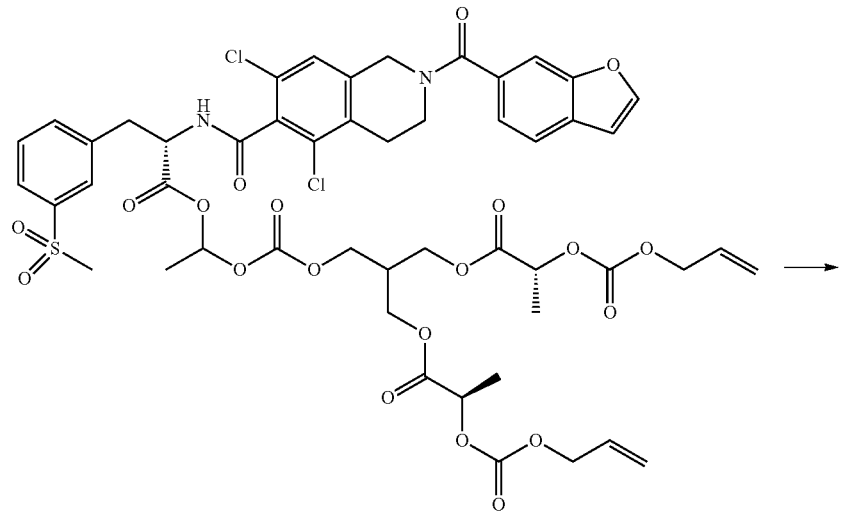

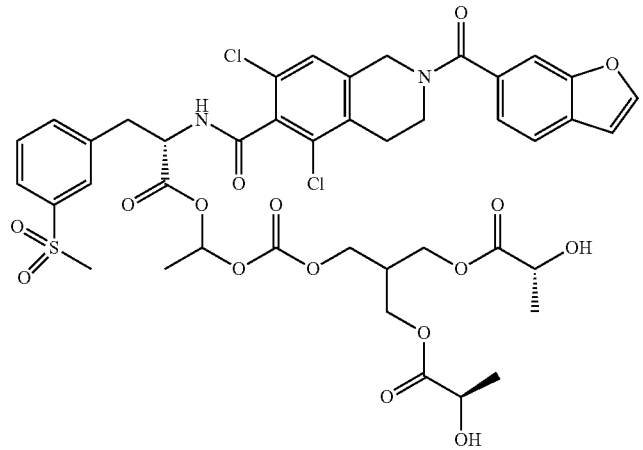

A solution of 2-((8S)-10-(2-(benzofuran-6-carbonyl)-5,7-dichloro-1,2,3,4-tetrahydroisoquinolin-6-yl)-5-methyl-8-(3-(methylsulfonyl)benzyl)-3,7,10-trioxo-2,4,6-trioxa-9-azadecyl)propane-1,3-diyl (2R,2'R)-bis(2-(((allyloxy)carbonyl)oxy)propanoate) (13 mg, 0.0113 mmol) in DCM (2 mL) was stirred under N$_2$. Phenylsilane (5.6 mL, 0.0453 mmol) and tetrakis(triphenylphosphine)palladium(O) (1.3 mg, 0.00113 mmol) were added and the mixture stirred at r.t. for 10 minutes. The solvent was evaporated in vacuo. The crude product was purified by preparative reversed-phase HPLC and desired fractions were combined, and the solvent evaporated in vacuo. The residue was dissolved in 1:1 MeCN—H$_2$O (2 mL) and the solution frozen. The solvent was then evaporated in vacuo (lyophilisation) to yield (3R)-1-hydroxy-7-((((R)-2-hydroxypropanoyl)oxy)methyl)-3-methyl-1,4,10-trioxo-2,5,9,11-tetraoxatridecan-12-yl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (3.5 mg, 33%) as a white solid. LCMS (Method F): Rt=7.31 min; [M+H]+=935.7. $^1$H-NMR (400 MHz CDCl$_3$) δ 7.90-7.91 (1H, m), 7.81-7.85 (1H, m), 7.72 (1H, m), 7.61-7.67 (3H, m), 7.44-7.55 (1H, m), 7.32 (1H, d, J=7.8 Hz), 7.13 (1H, br s), 6.74-6.83 (2.5H, m), 6.64 (0.5H, d, J=8.2 Hz), 5.26-5.32 (1H, m), 4.77 (2H, br s), 4.36-4.46 (1H, m), 4.12-4.32 (7H, m), 3.78 (2H, m), 3.44-3.51 (1H, m), 3.26 (1H, dt, J=14.3, 7.6 Hz), 3.05 (3H, d, J=1.4 Hz), 2.70-2.96 (4H, br m), 2.48-2.55 (1H, m), 1.57 (3H, t, J=5.5 Hz, partially obscured by H$_2$O peak), 1.37-1.41 (6H, m).

Chemical Synthesis Example 19

1-Chloroethyl 5-((R)-1,2-dithiolan-3-yl)pentanoate

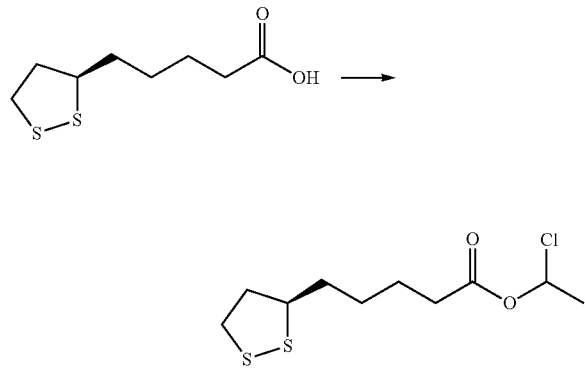

To a stirred mixture of sodium bicarbonate (122 mg, 1.60 mmol), tetrabutylammonium hydrogen sulfate (14 mg, 0.0400 mmol), and lipoic acid (83 mg, 0.400 mmol) in DCM (3 mL) under an atmosphere of N$_2$ was added H$_2$O (3 mL) followed by a solution of 1-chloroethyl sulfochloridate (100 mg, 0.560 mmol) in DCM (1 mL). The reaction mixture was stirred at r.t. for 16 hours. The organic phase was separated (phase separator) and the solvent evaporated in vacuo to yield 1-chloroethyl 5-((R)-1,2-dithiolan-3-yl)pentanoate as a pale-yellow gum (130 mg) which was purified no further.

Chemical Synthesis Example 20

1-(((S)-2-(2-(Benzofuran-6-carbonyl)-5,7-dichloro-1,2,3,4-tetrahydroisoquinoline-6-carboxamido)-3-(3-(methylsulfonyl)phenyl)propanoyl)oxy)ethyl 5-((R)-1,2-dithiolan-3-yl)pentanoate

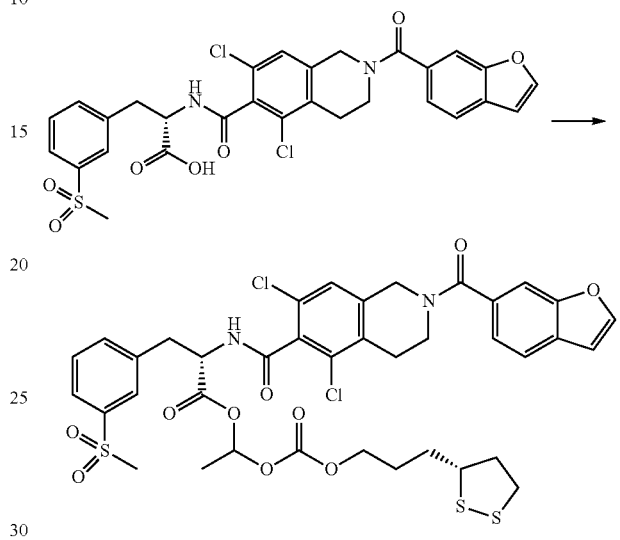

Crude 1-chloroethyl 5-((R)-1,2-dithiolan-3-yl)pentanoate (74 mg, 0.275 mmol) was dissolved in DMF (2.5 mL). Lifitegrast (178 mg, 0.275 mmol) and DIPEA (96 mL, 0.549 mmol) were added and the mixture stirred at 60° C. for 16 hours. The crude product was purified by preparative reversed-phase HPLC and desired fractions combined and the solvent volume reduced to 40 mL. The mixture was diluted with MeCN to produce a homogeneous mixture. The solution was frozen and the solvent evaporated in vacuo (lyophilisation) to yield 1-(((S)-2-(2-(benzofuran-6-carbonyl)-5,7-dichloro-1,2,3,4-tetrahydroisoquinoline-6-carboxamido)-3-(3-(methylsulfonyl)phenyl)propanoyl)oxy)ethyl 5-((R)-1,2-dithiolan-3-yl)pentanoate (9.1 mg, 4%) as a white solid. LCMS (Method C): Rt=7.97 min; [M+H]+=847.1. $^1$H-NMR (400 MHz, CDCl$_3$) δ 7.81-7.89 (2H, m), 7.71-7.72 (1H, m), 7.57-7.65 (3H, m), 7.47-7.52 (1H, m), 7.28-7.31 (1H, m), 6.88 (1H, td, J=10.8, 5.3 Hz), 6.81 (1H, m), 6.27 (1H, dd, J=10.8, 8.0 Hz), 5.19-5.27 (1H, m), 4.75 (1H, br s), 3.81 (1H, br s), 3.39-3.58 (2H, m), 3.05-3.29 (3H, m), 3.03 (3H, d, J=4.1 Hz), 2.87 (2H, br s), 2.31-2.48 (3H, m), 1.82-1.92 (1H, m), 1.38-1.74 (11H, m).

Chemical Synthesis Example 21

Methyl (R)-2-(trityloxy)propanoate

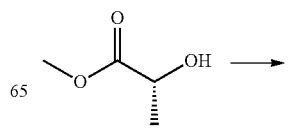

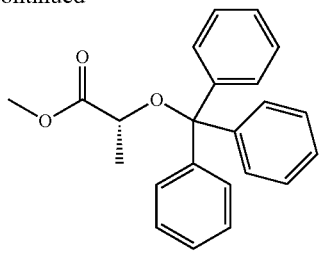

To a stirred solution of methyl (R)-2-hydroxypropanoate (0.91 mL, 11.1 mmol), 4-(dimethylamino)pyridine (210 mg, 1.74 mmol) and pyridine (0.70 mL) in MeCN (12 mL) was added triphenylmethyl chloride (2.38 g, 8.55 mmol) and the mixture stirred at reflux for 16 hours. The reaction mixture was cooled and allowed to stand at r.t. for 24 hours then partitioned between EtOAc and H₂O. The organic phase was washed successively with 1M NaHCO₃(aq), sat. NaHCO₃(aq), sat. Na₂CO₃(aq) and sat. brine solution. The organic phase was dried (MgSO₄), filtered and the solvent evaporated in vacuo to yield methyl (R)-2-(trityloxy)propanoate (2.98 g, 77%) as a pale yellow oil. H-NMR (400 MHz, CDCl₃) δ 7.41-7.52 (6H, m), 7.18-7.35 (13H, m), 4.20 (1H, q, J=6.7 Hz), 3.22 (3H, s), 1.37 (3H, d, J=6.9 Hz).

Chemical Synthesis Example 22

(R)-2-(Trityloxy)propanoic Acid

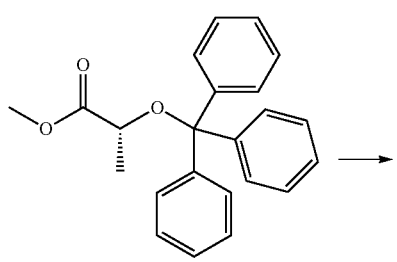

Methyl (2R)-2-trityloxypropanoate (2.98 g, 8.60 mmol) and sodium hydroxide (3.08 g, 77.0 mmol) were dissolved in MeOH (28 mL) and the mixture stirred at r.t. for 72 hours. The reaction mixture was filtered, and the filtrate diluted with H₂O (40 mL). The MeOH was evaporated in vacuo and the solution washed with tert-butyl methyl ether. The aqueous phase was acidified to pH3 by the addition of 5M HCl(aq) and extracted with tert-butyl methyl ether. The organic phase was washed with sat. brine solution, dried (MgSO₄), and the solution filtered. The solvent was evaporated in vacuo to yield (R)-2-(trityloxy)propanoic acid (1.53 g, 54%) as a pale yellow gum. LCMS (Method E): Rt=2.87 min, [M–H]–=331.2.

Chemical Synthesis Example 23

(R)-Chloroethyl (2R)-2-(trityloxy)propanoate

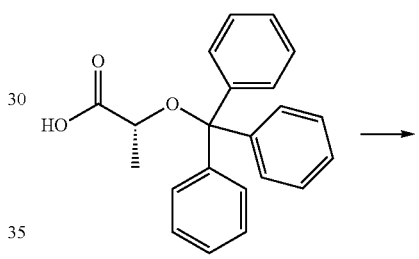

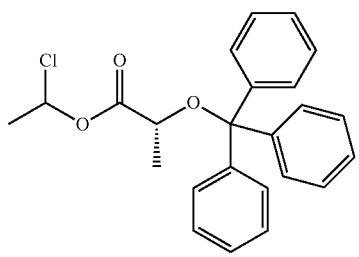

To a stirred mixture of (R)-2-(trityloxy)propanoic acid (100 mg, 0.301 mmol), tetrabutylammonium hydrogen sulfate (10 mg, 0.0301 mmol), and NaHCO₃ (101 mg, 1.20 mmol) in DCM (1.5 mL) and water (1.5 mL) under N₂ was added 1-chloroethyl sulfochloridate (75 mg, 0.421 mmol) in DCM (0.5 mL) and the mixture stirred at r.t. for 2 hours. The solution was passed through a phase separator, and the filtrate evaporated in vacuo to give crude 1-chloroethyl (2R)-2-(trityloxy)propanoate (130 mg) as a pale yellow solid. LCMS (Method E): Rt=3.53 min (no ionisation).

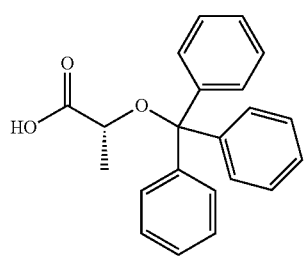

Chemical Synthesis Example 24

1-(((R)-2-(Trityloxy)propanoyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

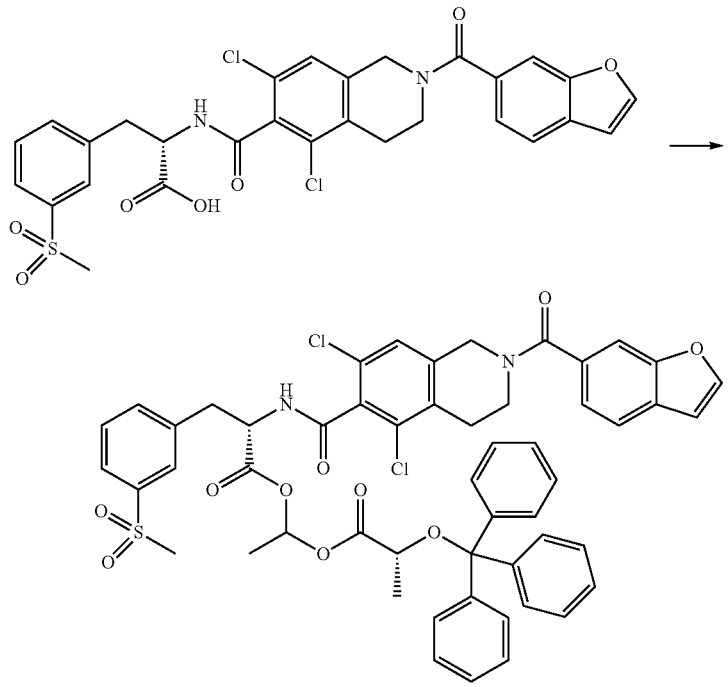

To a stirred solution of 1-chloroethyl (2R)-2-(trityloxy) propanoate (100 mg, 0.253 mmol) in anhydrous DMF (2 mL) was added DIPEA (88 mL, 0.506 mmol) and Lifitegrast (125 mg, 0.193 mmol) and the mixture stirred at 55° C. under $N_2$ for 16 h. The mixture was diluted with EtOAc (50 mL) and sat. $NaHCO_{3(aq)}$ (20 mL) and the layers separated. The organic phase was washed with sat. brine solution (20 mL), dried ($MgSO_4$), filtered and the solvent evaporated in vacuo. The crude product was purified by flash column chromatography (Biotage SP1; 10 g cartridge) eluting with isohexane→EtOAc to yield 1-(((R)-2-(trityloxy)propanoyl) oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (61 mg, 25%) as a white solid. LCMS (Method E): Rt=3.37 min; [M+H]+=973.2 (weak ionisation).

Chemical Synthesis Example 25

1-(((R)-2-Hydroxypropanoyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

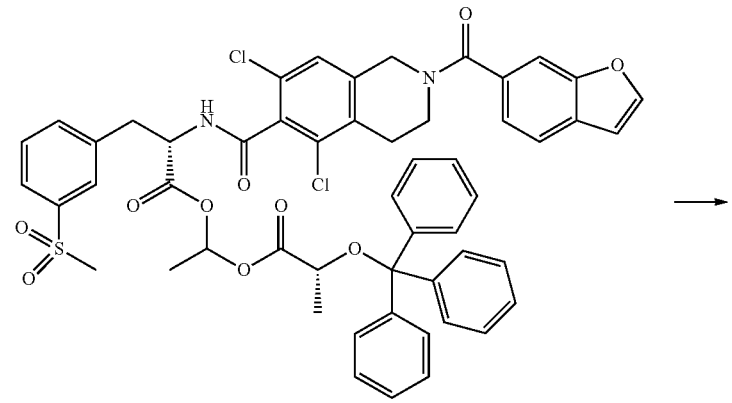

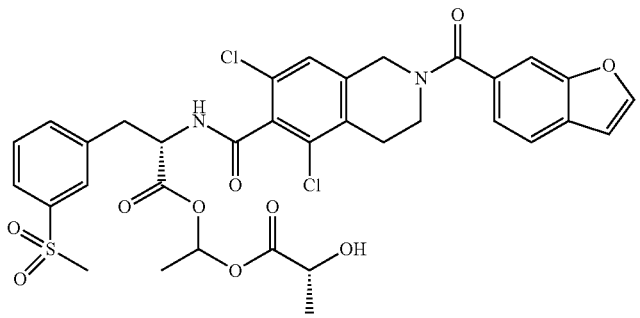

Method A

To a stirred solution of 1-(((R)-2-(trityloxy)propanoyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (14 mg, 0.0144 mmol) in anhydrous DCM (0.5 mL) at r.t. under $N_2$ was added triethylsilane (110 μL, 0.0719 mmol) followed by the dropwise addition of TFA (50 μL). The reaction was stirred at r.t. for 73 hours. Anhydrous DCM (1 mL), triethylsilane (110 μL, 0.0719 mmol) and TFA (50 μL) were added and the reaction stirred at r.t. for 1 hour.

Method B

To a stirred solution of 1-(((R)-2-(trityloxy)propanoyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (48 mg, 0.0493 mmol) in anhydrous DCM (1.5 mL) at r.t. under $N_2$ was added triethylsilane (79 μL, 0.493 mmol) followed by the dropwise addition of TFA (150 μL). The mixture was stirred at r.t. for 75 minutes.

Method C

The two reaction mixtures obtained from methods A & B were combined, diluted with DCM (30 mL) and sat. $NaHCO_{3(aq)}$ (30 mL) and the layers separated. The aqueous phase was extracted with DCM (20 mL) and the combined organics washed with sat. brine solution (10 mL), dried ($MgSO_4$), filtered and the solvent evaporated in vacuo. The crude product was purified by preparative reversed-phase HPLC. Desired fractions were combined and the solution frozen. The solvent was evaporated in vacuo (lyophilisation) and the residue dissolved in 1:1 MeCN—$H_2O$, frozen, and evaporated in vacuo (lyophilisation) to yield 1-(((R)-2-hydroxypropanoyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (15 mg, 42%) as a white solid. LCMS (Method C): Rt=6.49 min; [M+H]+=731.2. $^1$H-NMR (400 MHz, $CDCl_3$) δ 7.79-7.88 (2H, m), 7.72 (1H, d, J=2.3 Hz), 7.57-7.68 (3H, m), 7.51 (1H, td, J=7.9, 3.5 Hz), 7.31 (1H, d, J=7.8 Hz), 6.90-6.98 (1H, m), 6.80-6.86 (1H, m), 6.22-6.40 (1H, m), 5.24 (1H, dd, J=14.0, 6.2 Hz), 4.79 (2H, s), 4.24-4.37 (1H, m), 3.87 (2H, br s), 3.38-3.44 (1H, m), 3.21-3.32 (1H, m), 3.06 (3H, d, J=10.5 Hz), 2.88 (2H, s), 1.55 (3H, dd, J=12.4, 5.5 Hz), 1.42 (3H, dd, J=7.1, 5.7 Hz).

Chemical Synthesis Example 26

The following compound was made by analogous method to that described above for 1-(((R)-2-Hydroxypropanoyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate:

| Structure | Analytical Data |
|---|---|
| (structure shown) | LCMS (QC Method C): Rt = 6.34 mins; [M + H]+ = 717.0 |

Chemical Synthesis Example 27

1-(((S)-2-(2-(Benzofuran-6-carbonyl)-5,7-dichloro-1,2,3,4-tetrahydroisoquinoline-6-carboxamido)-3-(3-(methylsulfonyl)phenyl)propanoyl)oxy)ethyl Pivalate

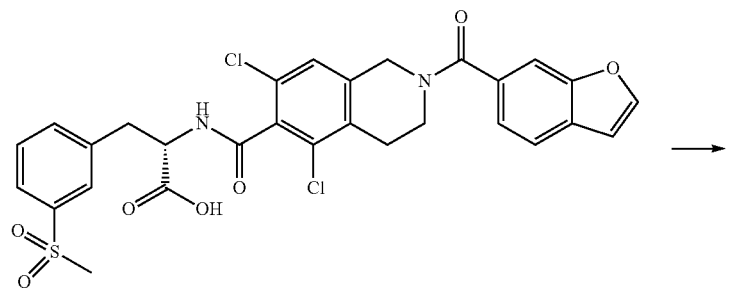

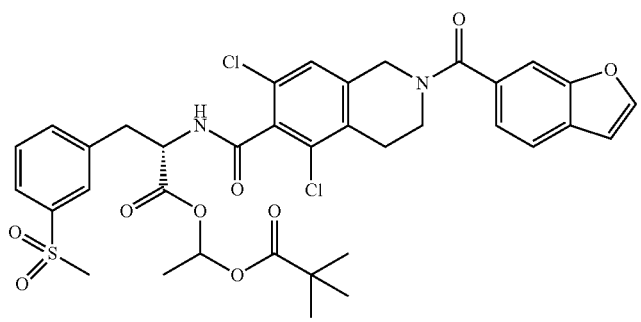

To a stirred solution of 1-chloroethyl pivalate (40 mg, 0.243 mmol) in anhydrous DMF (1.6 mL) was added DIPEA (85 mL, 0.486 mmol) and Lifitegrast (130 mg, 0.201 mmol). The mixture was stirred at 40° C. under $N_2$ for 72 h. The crude product was purified by preparative reversed-phase HPLC, desired fractions were combined and approximately half the solvent evaporated in vacuo. The solution was frozen and the solvent evaporated in vacuo (lyophilisation) to yield 1-(((S)-2-(2-(benzofuran-6-carbonyl)-5,7-dichloro-1,2,3,4-tetrahydroisoquinoline-6-carboxamido)-3-(3-(methylsulfonyl)phenyl)propanoyl)oxy)ethyl pivalate (40 mg, 22%) as an off-white solid. LCMS (Method C): Rt=7.66 min; [M+H]+=743.1. $^1$H-NMR (400 MHz, CDCl$_3$) δ 7.80-7.91 (2H, m), 7.71 (1H, d, J=1.8 Hz), 7.56-7.64 (3H, m), 7.49 (1H, td, J=7.7, 5.3 Hz), 7.29 (1H, d, J=6.4 Hz), 6.81-6.89 (2H, m), 6.32 (1H, q, J=7.8 Hz), 5.19-5.27 (1H, m), 4.74 (2H, br s), 3.78 (2H, br s), 3.41 (1H, dd, J=14.4, 5.7 Hz), 3.11-3.27 (1H, m), 3.03 (3H, d, J=6.9 Hz), 2.85-2.94 (2H, m), 1.50 (3H, dd, J=15.8, 5.3 Hz), 1.15-1.19 (9H, m).

Chemical Synthesis Example 28

1-((Methoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

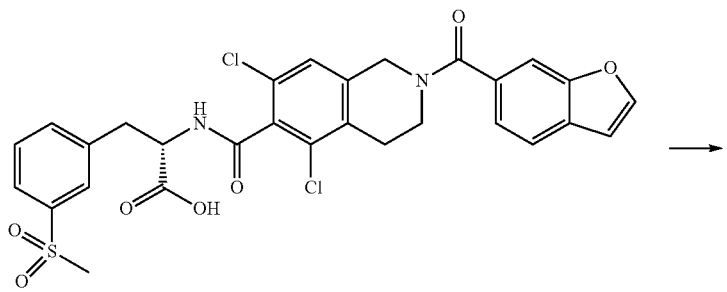

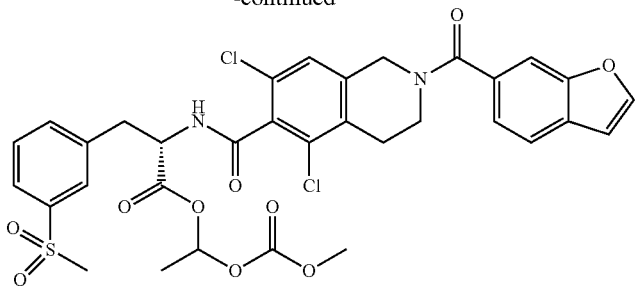

Lifitegrast (205 mg, 0.333 mmol) and DIPEA (90 mL, 0.517 mmol) were dissolved in anhydrous DMF (5 mL). 1-Chloroethyl methyl carbonate (40 mg, 0.289 mmol) was added and the mixture stirred at r.t. for 16 hours followed by stirring at 40° C. for 2 hours. DIPEA (50 mL, 0.287 mmol) was added and the mixture stirred at 50° C. for 20 hours. The solvent was evaporated in vacuo and the residue dissolved in DCM (20 mL). The solution was washed with sat. NaHCO$_{3(aq)}$ (20 mL) and the layers separated. The organic phase was evaporated in vacuo and the crude product purified by flash chromatography eluting with isohexane→8:2 EtOAc-isohexane to yield 1-((methoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (88 mg, 42%) as a white solid. LCMS (Method C): Rt=6.94 min; [M+H]+=717.1. $^1$H-NMR (400 MHz, CDCl$_3$) δ 7.79-7.86 (2H, m), 7.70 (1H, d, J=1.8 Hz), 7.57-7.64 (3H, m), 7.45-7.51 (1H, m), 7.28 (1H, d, J=7.8 Hz), 6.75-6.80 (2H, m), 6.43 (1H, t, J=8.5 Hz), 5.24 (1H, s), 4.72 (2H, br s), 3.59-4.00 (5H, m), 3.41 (1H, dd, J=14.7, 5.5 Hz), 3.21-3.29 (1H, m), 3.01 (3H, d, J=3.7 Hz), 2.85 (2H, s), 1.51-1.64 (4H, m).

Chemical Synthesis Example 29

1-((Ethoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

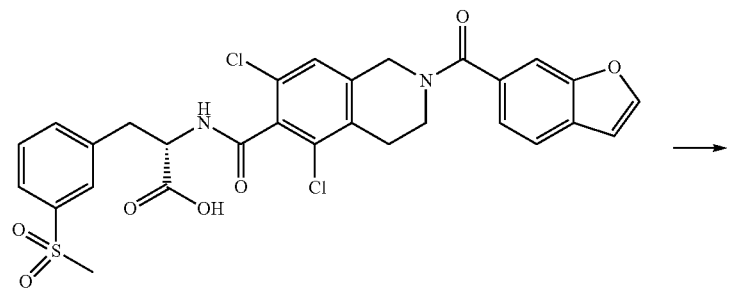

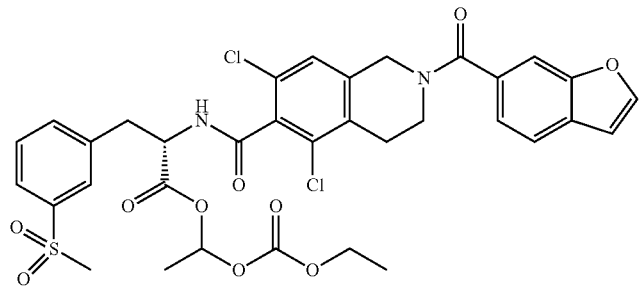

To a stirred solution of 1-chloroethyl ethyl carbonate (37 mg, 0.243 mmol) in DMF (1.6 mL) was added DIPEA (85 mL, 0.486 mmol) and Lifitegrast (120 mg, 0.185 mmol) and the mixture stirred at 40° C. under $N_2$ for 16 hours. DIPEA (85 mL, 0.486 mmol) and 1-chloroethyl ethyl carbonate (37 mg, 0.243 mmol) were added and the mixture stirred at 40° C. for 4 hours. The crude product was purified by preparative reversed-phase HPLC. Fractions containing desired product were combined, frozen and the solvent evaporated in vacuo (lyophilisation) to yield 1-((ethoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (6.0 mg, 3%) as an off-white solid. LCMS (Method C): Rt=7.15 min; [M+H]+=731.1.

Chemical Synthesis Example 30

1-Chloroethyl Propionate

Propionyl chloride (7.0 mL, 80.1 mmol) was placed under an atmosphere of $N_2$ and cooled to 0° C. Zinc chloride (0.7M in THF, 1.10 mL, 0.801 mmol) was added followed by chilled acetaldehyde (5.40 mL, 96.1 mmol). The reaction mixture was stirred at 0° C. for 2 hours. The mixture was filtered and the filtrate evaporated in vacuo. The residue was dissolved in isohexane (10 mL) and the solution washed successively with sat. $NaHCO_{3(aq)}$ (10 mL), $H_2O$ (10 mL) and sat. brine solution (10 mL). The organic phase was dried ($MgSO_4$), filtered and the solvent evaporated in vacuo to yield 1-chloroethyl propionate (4.54 g, 41%) as an orange oil *.

*The product contained a mixture of impurities and was purified no further—used subsequently in crude form.

Chemical Synthesis Example 31

1-((Ethoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate

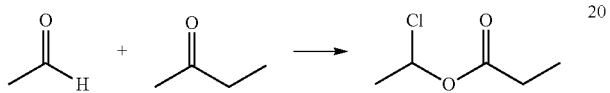

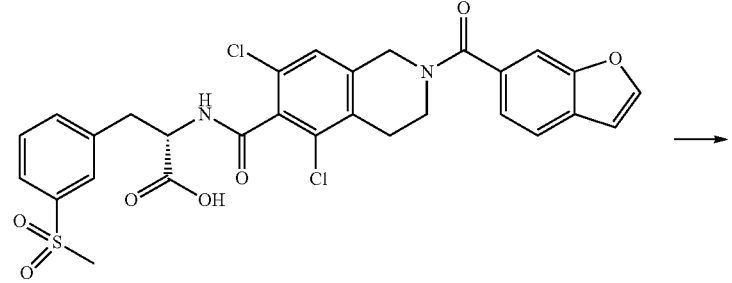

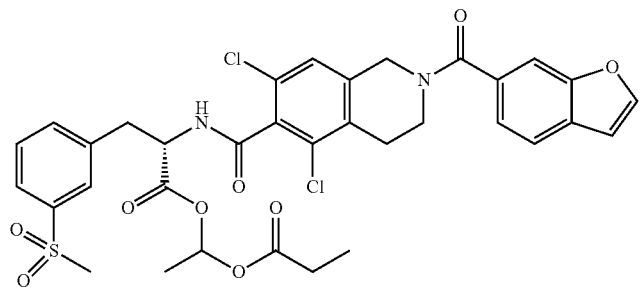

A mixture of Lifitegrast (100 mg, 0.162 mmol) and 1-chloroethyl propionate (111 mg, 0.812 mmol) were dissolved in DMF (1 mL). DIPEA (170 mL, 0.975 mmol) was added and the mixture stirred at 60° C. under $N_2$ for 18 hours. The crude product was purified by preparative reversed-phase HPLC and desired fractions combined, frozen and the solvent evaporated in vacuo (lyophilisation) to yield 1-((ethoxycarbonyl)oxy)ethyl (2S)-2-(2-(benzofuran-6-carbonyl)-5,7-dichloro-1,2,3,4-tetrahydroisoquinoline-6-carboxamido)-3-(3-(methylsulfonyl)phenyl)propanoate (41.1 mg, 35%) as an off-white solid. LCMS (Method B). Rt =3.08 min; [M+H]+=715.3. $^1$H-NMR (400 MHz, $CDCl_3$) δ 7.83-7.90 (2H, m), 7.73 (1H, d, J=2.7 Hz), 7.65 (1H, d, J=7.8 Hz), 7.59-7.61 (2H, m), 7.48-7.53 (1H, m), 7.31-7.33 (1H, m), 7.14 (1H, br s), 6.87-6.93 (1H, m), 6.82-6.83 (1H, m), 6.22-6.28 (1H, m), 5.21-5.28 (1H, m), 4.78 (2H, br s), 3.84 (2H, br s), 3.40-3.46 (1H, m), 3.20-3.31 (1H, m), 3.05 (1.5H, s), 3.04 (1.5H, s) 2.88 (2H, br s), 2.32-2.41 (2H, m), 1.53 (1.5H, d, J=5.2 Hz, partially obscured by $H_2O$ peak), 1.50 (1.5H, d, J=5.6 Hz), 1.11-1.17 (3H, m).

II. Biological Evaluation

Example 1: Rabbit Cornea Homogenate Stability Assay

Determining Rabbit Cornea Homogenate stability of the test compounds was performed using HPLC-MS. The assay was performed at two concentrations of Rabbit Cornea Homogenate (0.15 mg/ml and 0.45 mg/ml total protein) so that any hydrolysis observed could be assigned as esterase dependent or not.

Rabbit Cornea Homogenisation

Five rabbit corneas (e.g. New Zealand Whites) of approx. 50 mg each were sliced and scraped with a scalpel and tweezers until reduced to small (1-3 mm), thin pieces. These were transferred into a tared vial and accurately weighed, then diluted with 10 volumes aqueous PBS pH7.4

Sample was cooled intermittently on ice and shear homogenized for 3 minutes, then centrifuged for 3 min at 3000 rpm. The supernatant was pipetted off into a vial, and total protein concentration determined at 280 nm. Sample was stored at −78° C.

Rabbit Cornea Esterase Assay
Preparation of Stock Solutions:
10 mM Compound stocks were diluted to 100 μM in a 96 deep-well plate: 10 μl of 10 mM Compound stock was added to 990 μl 50 mM HEPES, pH7.5 buffer.
Compounds were further diluted to 10 μM: 100 μl of 100 μM compound was added to 900 μl 50 mM HEPES, pH7.5 buffer.
Esterase homogenate was diluted to 300 ng/μl and 900 ng/μl Assay Conditions:
A heater shaker was set to 37° C. Into a suitable 96 well plate (Run Plate), 75 μl of 300 or 900 ng/μl esterase homogenate was pipetted into each of the required wells (2 min, 5 min, 10 min, 20 min and 45 min). The plate was sealed and then warmed at 37° C. for 5 min.
Another 96 well PCR plate is put on ice (Kill Plate). To this was added 100 μl of MeCN to each well, labelled 0 min, 2 min, 5 min, 10 min, 20 min and 45 min. The plate was covered to minimise evaporation.
For the T=0 sample only, to the 100 μl cold MeCN stop solution was added 50 μl of 300 or 900 ng/μl esterase homogenate followed by 50 μl of 10 μM compound solution For the remaining time points, 75 μl of 10 μM compound solution was added to the Run Plate starting from T=45 min row and ending with T=2 min row.
At the appropriate time point, 100 μl of the assay mixture was added to the matching kill plate well containing 100 μl of cold MeCN.
Samples were analysed as soon as practicable by LCMS (Waters Xevo TQ-S or Micromass Ultima).
Parent conjugate and parent concentrations were determined against appropriate standard response curves and the half-life (T/2) of the parent conjugate was calculated using the peak area of the parent conjugate at each time point in the linear region of the log—linear plot.

Hydrolysis Rates of Example Compounds

TABLE 2

| Comp | Cornea Homogenate Conc (mg/mL) | Esterase % Lifitegrast formation at 45 min | API Formation rate (%/min) |
|---|---|---|---|
| 2 | 0.15 | B | b |
|   | 0.45 | C | c |
| 3 | 0.15 | B | d |
|   | 0.45 | C | b |
| 4 | 0.15 | B | b |
|   | 0.45 | C | c |
| 5 | 0.15 | B | b |
|   | 0.45 | D | d |
| 6 | 0.15 | A | a |
|   | 0.45 | B | b |
| 7 | 0.15 | B | b |
|   | 0.45 | C | c |
| 8 | 0.15 | B | b |
|   | 0.45 | C | d |
| 9 | 0.15 | B | b |
|   | 0.45 | C | d |
| 10 | 0.15 | A | b |
|   | 0.45 | B | b |
| 11 | 0.15 | B | b |
|   | 0.45 | B | c |
| 12 | 0.15 | A | a |
|   | 0.45 | A | a |
| 13 | 0.15 | A | a |
|   | 0.45 | A | a |
| 14 | 0.15 | C | c |
|   | 0.45 | D | d |
| 15 | 0.15 | C | d |
|   | 0.45 | D | d |
| 16 | 0.15 | D | d |
|   | 0.45 | D | d |
| 17 | 0.15 | B | b |
|   | 0.45 | C | c |
| 18 | 0.15 | C | c |
|   | 0.45 | D | d |
| 19 | 0.15 | B | b |
|   | 0.45 | B | b |
| 20 | 0.15 | A | a |
|   | 0.45 | B | b |

A: percent active pharmaceutical ingredient (API) formation <25%;
B: percent API formation 25% to 50%;
C: percent API formation 51% to 75%;
D: percent API formation >75%.
a: API formation rate <0.5%/min;
b: API formation rate 0.5-1.0%/min;
c: API formation rate 1.0-1.5%/min;
API formation rate >1.5%/min.

Example 2: Aqueous Hydrolysis Stability Assay

Determination of aqueous stability of the test compounds was performed using HPLC-MS. A test compound 10 mM stock solution was prepared in DMSO. 10 μl of the DMSO stock solution was dissolved in 990 μl of 50 mM HEPES pH 7.5 buffer or 1:1 (v/v) of Acetonitrile: Water to make a100 M solution. Final DMSO concentration was 10%. The solution was kept at room temperature and injected without delay into the LCMS (Waters Xevo TQ-S or Micromass Ultima). Additional injections were performed at appropriate time points. Half-life ($T_{1/2}$) of the parent conjugate was calculated using the peak area of the parent conjugate at each time point in the linear region of the log—linear plot.

TABLE 3

| Comp | Hydrolytic % Lifitegrast formation at [time] |
|---|---|
| 2 | A [192 min] |
| 3 | B [45 min] |
| 4 | B [45 min] |
| 5 | A [192 min] |
| 6 | C [142 min] |
| 7 | B [142 min] |
| 8 | A [45 min] |
| 9 | B [142 min] |
| 10 | C [142 min] |
| 11 | C [142 min] |
| 12 | B [142 min] |
| 13 | — |
| 14 | B [142 min] |
| 15 | B [45 min] |
| 16 | C [142 min] |
| 17 | A [45 min] |
| 18 | C [45 min] |
| 19 | B [45 min] |
| 20 | A [45 min] |

A: percent active pharmaceutical ingredient (API) formation <1.5%;
B: percent API formation 1.5-4%;
C: percent API formation >4%.

Example 3: Mouse Model of Experimental Dry Eye Disease

Female C57BL/6 mice (6-8 weeks old) or female HEL BCR Tg mice (6-8 weeks old) are commercially obtained. Experimental dry eye is induced as described by Niederkorn, et al. (J. Immunol. 2006,176:3950-3957) and Dursun et al. (Invest. Ophthalmol. Vis. Sci. 2002, 43:632-638). In brief, mice are exposed to desiccating stress in perforated cages with constant airflow from fans positioned on both sides and room humidity maintained at 30% to 35%. Injection of scopolamine hydrobromide (0.5 mg/0.2 mL; Sigma-Aldrich, St. Louis, Mo.) is administered subcutaneously, three times a day (8:00 AM, 12:00 noon, and 5:00 PM), on alternating hind-flanks to augment disease. Mice are exposed to desiccating stress for 3 weeks. Untreated control mice are maintained in a nonstressed environment at 50% to 75% relative humidity without exposure to forced air. Test animals are exposed to test compound and subsequently tear samples are obtained to determine stability of test compounds, and tissue samples are taken to determine presence of pro-inflammatory biomarkers.

III. Preparation of Pharmaceutical Dosage Forms

Example 1: Solution for Topical Ophthalmic Use

The active ingredient is a compound of Table 1, or a pharmaceutically acceptable salt thereof, and is formulated as a solution with a concentration of between 0.1-1.5% w/v.

We claim:

1. A compound, having the structure of Formula (Ia):

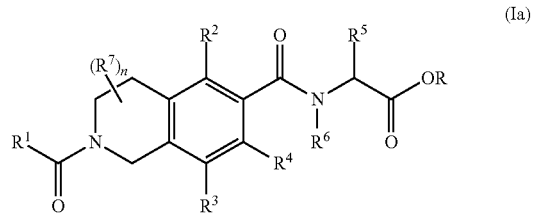

wherein
 $R^1$ is optionally substituted heteroaryl;
 $R^2$, $R^3$, and $R^4$ are each independently hydrogen, deuterium, cyano, halo, alkoxy, alkyl, haloalkyl, or cycloalkyl, wherein the alkoxy, alkyl, or cycloalkyl is optionally substituted;
 $R^5$ is -L-$R^{5a}$;
  L is alkylene;
  $R^{5a}$ is optionally substituted aryl;
 $R^6$ is hydrogen, deuterium, or alkyl;
 each $R^7$ is independently deuterium, halo, or alkyl;
 n is 0-6;
 R is -L'-D;
  D is a radical of a keratolytic agent; and
  L' is a linker,
or a pharmaceutically acceptable salt or solvate thereof.

* * * * *